(12) United States Patent
Fukuda et al.

(10) Patent No.: US 7,402,548 B2
(45) Date of Patent: Jul. 22, 2008

(54) BENZOXAZOLE COMPOUNDS, PROCESS FOR PRODUCING THE SAME AND HERBICIDES

(75) Inventors: Shohei Fukuda, Ube (JP); Akira Nakamura, Ube (JP); Motohisa Shimizu, Ube (JP); Tatsuo Okada, Ube (JP); Satoshi Oohida, Ube (JP); Takehiko Asahara, Ube (JP)

(73) Assignee: Kyoyu Agri Co., Ltd., Kanagawa (JP)

( * ) Notice: Subject to any disclaimer, the term of this patent is extended or adjusted under 35 U.S.C. 154(b) by 411 days.

(21) Appl. No.: 11/001,103

(22) Filed: Dec. 1, 2004

(65) Prior Publication Data
US 2005/0233909 A1      Oct. 20, 2005

Related U.S. Application Data

(62) Division of application No. 10/332,359, filed as application No. PCT/JP01/05793 on Jul. 4, 2001, now Pat. No. 6,844,295.

(30) Foreign Application Priority Data

| Jul. 4, 2000 | (JP) | ............................. 2000/202687 |
| Sep. 8, 2000 | (JP) | ............................. 2000/272759 |
| Sep. 13, 2000 | (JP) | ............................. 2000/277674 |

(51) Int. Cl.
*A01N 43/76* (2006.01)
*C07D 263/52* (2006.01)

(52) U.S. Cl. ...................................... 504/270; 548/216

(58) Field of Classification Search ................ 504/270; 548/216
See application file for complete search history.

(56) References Cited

U.S. PATENT DOCUMENTS 4,576,629 A    3/1986 Morland et al.

FOREIGN PATENT DOCUMENTS

| JP | 45001892 | * | 1/1970 |
| WO | WO-97/29095 | | 8/1997 |

OTHER PUBLICATIONS

May 20, 1977 "Addition of 2-ethylbenzazoles to Aromatic Aldehydes in the Presence of Aqueous Sodium Hydroxide" Dryanska, V. et al. Izvestiya PO Khimiya vol. 10, No. 4 pp. 547-553.

Jul. 6, 1983 "Reagents and Synthetic Methods" Palomo, C. et al. Bulletin de la Societe Chimique de France vol. 3-4, No. 2 pp. 142-144.
Jan. 28, 1993 "Novel Thioxopyrimidinedione Derivatives" Bhalla, M. et al. Eur. J. Med. Chem. vol. 28 pp. 643-646.
1995, Synthesis and pharmacological evaluation of 1,2,4-triazine and its congeners, M. Bhalla et al., Bollettino Chimico Farmaceutico, Societa Editoriale Farmaceutica, Milano, It, vol. 134, No. 1 pp. 9-15.
1994, Synthesis of 1,3,4-thiadiazole[3,2,-a]-s-triazine-5, 7-dithione derivatives and their pharmacological evaluation M. Bhalla, et al. Bollettino Chimico Farmaceutico vol. 133, No. 8 pp. 521-526.
1977, "Addition of 2-ethylbenzazoles to Aromatic Aldehydes in the Presence of Aqueous Sodium Hydroxide" Dryanska, V. et al. Izvestiya PO Khimiya vol. 10, No. 4 pp. 547-553.

* cited by examiner

*Primary Examiner*—Kamal A Saeed
(74) *Attorney, Agent, or Firm*—Jordan and Hamburg LLP

(57) ABSTRACT

The present invention relates to benzoxazole compounds represented by the following formula (I):

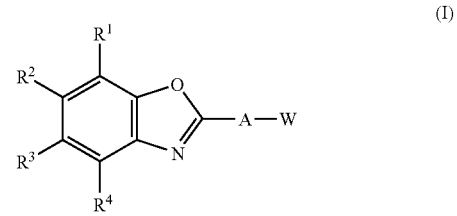

(I)

wherein $R^1$ to $R^4$ may be the same or different from each other, and each represent a hydrogen atom, alkyl group having 1 to 6 carbon atoms, alkoxy group having 1 to 4 carbon atoms, haloalkyl group having 1 to 4 carbon atoms, haloalkoxy group having 1 to 4 carbon atoms, halogen atom, nitro group, cyano group, $R^{12}S(O)_n$, alkoxycarbonyl group having 1 to 4 carbon atoms, amino group, —NHCOR$^{11}$ or carbonyl group, where $R^{11}$ and $R^{12}$ each represent an alkyl group having 1 to 6 carbon atoms, and n is an integer of 0 to 2, A represents a single bond, $CHR^5$—Y, $CR^5$=$CR^6$, $CR^5R^7$—$CHR^6$ or $CHR^5$, where $R^5$ represents a hydrogen atom, hydroxyl group, halogen atom or alkyl group, $R^6$ and $R^7$ each represent a hydrogen atom, hydroxyl group, alkyl group, halogen atom or substituted sulfonyloxy group, Y represents O, S or NH, and W represents a substituted or unsubstituted benzene ring or hetero ring, and processes for preparing the same.

7 Claims, No Drawings

BENZOXAZOLE COMPOUNDS, PROCESS FOR PRODUCING THE SAME AND HERBICIDES

This Application is a Divisional of U.S. application Ser. No. 10/332,359 filed on Jan. 06, 2003, now U.S. Pat. No. 6,844,295, which is a 371 of PCT/JP01/05793 filed on Jul. 04, 2001.

TECHNICAL FIELD

The present invention relates to a benzoxazolecompound, a process for producing the same and a herbicide which comprises containing the same as effective ingredients.

BACKGROUND ART

As a similar compound of that of the present invention, there may be mentioned an aniline compound described in Japanese Provisional Patent Publication No. 139767/1998.

However, the compound of the present invention is clearly different from the above compound of the reference at least the structure connecting from the benzoxazole portion and a phenyl portion, and in a part of the embodiment of the present invention, the point of the aniline portion being replaced by a hereto ring is different.

Accordingly, the compound of the present invention is a novel compound and the use thereof is also not yet known.

An object of the present invention is to provide a herbicide containing a benzoxazole compound as an effective ingredient.

SUMMARY OF THE INVENTION

The present inventors have studied to solve the above-mentioned problems, and as a result, they have found that a chemical comprising a novel benzoxazole compound as an effective ingredient has an excellent effect as a herbidice to accomplish the present invention.

That is, the present invention is as follows.

The first invention relates to a benzoxazolecompound represented by the following formula (I):

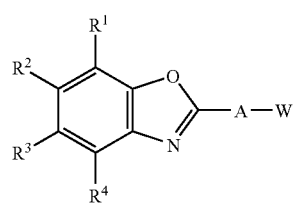

(I)

wherein $R^1$ to $R^4$ may be the same or different from each other, and each represent a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, $R^{12}S(O)_n$, an alkoxycarbonyl group having 1 to 4 carbon atoms, or a carbonyl group, where $R^{12}$ represents an alkyl group having 1 to 6 carbon atoms, n is an integer of 0 to 2, provided that the case where all are hydrogen atoms is excluded, A represents a single bond, $CHR^5$—Y, $CR^5$=$CR^6$, $CR^{5'}$=$CR^{6'}$, $CR^5R^7$—$CHR^6$, $CR^{5'}R^{7'}$—$CHR^{6'}$ or $CHR^5$, where $R^5$ represents a hydrogen atom, an alkyl group having 1 to 6 carbon atoms and a haloalkyl group having 1 to 4 carbon atoms, $R^6$ and $R^7$ each represent a hydrogen atom, a hydroxyl group, an alkyl group having 1 to 6 carbon atoms or a halogen atom, $R^{5'}$ represents an alkyl group having 1 to 6 carbon atoms, $R^{6'}$ represents a hydrogen atom, a hydroxyl group, a halogen atom or an alkyl group having 1 to 4 carbon atoms, $R^{7'}$ represents a hydrogen atom, a hydroxyl group, a halogen atom or a substituted sulfonyloxy group, Y represents O, S or NH, (1) when A is a single bond,
W represents a following formula (II):

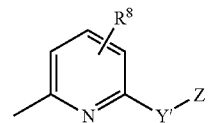

(II)

wherein $R^8$ represents a haloalkyl group having 1 to 4 carbon atoms, an alkylsulfonyl group having 1 to 4 carbon atoms, a cyano group a haloalkoxy group having 1 to 4 carbon atoms, a cyano group, a haloalkoxy group having 1 to 4 carbon atoms a hydrogen atom or a halogen atom, Y' represents O, $S(O)_n$ or $NR^{13}$, where n is an integer of 0 to 2, $R^{13}$ represents a hydrogen atom or an alkoxy group having 1 to 4 carbon atoms, Z represents a following formula (III-1):

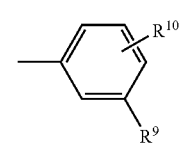

(III-1)

wherein $R^9$ represents a hydrogen atom, a cyano group, a haloalkyl group having 1 to 4 carbon atoms or a halogen atom, $R^{10}$ represents a hydrogen atom, a halogen atom, an alkyl group having 1 to 4 carbon atoms, an alkoxy group having 1 to 4 carbon atoms or a haloalkyl group having 1 to 4 carbon atoms, or a hetero ring, (2) when A is $CR^{5'}$=$CR^{6'}$ or $CR^{5'}R^{7'}$—$CHR^{6'}$,
W represents a benzene ring represented by the following formula (III-2):

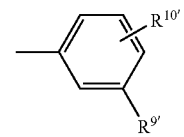

(III-2)

wherein $R^{9'}$ represents a hydrogen atom, a cyano group, a haloalkyl group having 1 to 4 carbon atoms, a haloalkoxy group having 1 to 4 carbon atoms, a nitro group or $R^{12}S(O)_n$, where $R^{12}$ and n have the same meanings as defined above, $R^{10'}$ represents a hydrogen atom, a halogen atom, a haloalkyl group having 1 to 4 carbon atoms or a cyano group, (3) when A is $CHR^5$—Y, $CR^5$=$CR^6$, $CR^5R^7$—$CHR^6$ or $CHR^5$, W represents a hetero ring other than a 1H-benzotriazol-1-yl group, a 1,3-dioxoisoindolynyl group or a 1,3,5-triazine group.

The second invention relates to a process for producing a compound (I-a) represented by the following formula (I-a);

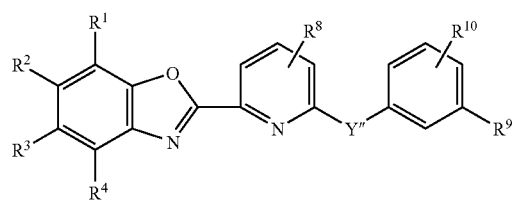

(I-a)

wherein $R^1$ to $R^4$ have the same meanings as defined above, $R^9$ represents a haloalkyl group having 1 to 4 carbon atoms, an alkylsulfonyl group having 1 to 4 carbon atoms, a cyano group, a haloalkoxy group having 1 to 4 carbon atoms, a hydrogen atom or a halogen atom, $R^8$ has the same meaning as defined above, $R^9$ represents a hydrogen atom, a cyano group, a haloalkyl group having 1 to 4 carbon atoms or a halogen atom, $R^{10}$ represents a hydrogen atom, a halogen atom, an alkyl group having 1 to 4 carbon atoms, an alkoxy group having 1 to 4 carbon atoms or a haloalkyl group having 1 to 4 carbon atoms, and Y" represents an oxygen atom or a sulfur atom, which comprises reacting a compound (IX) represented by the following formula (IX):

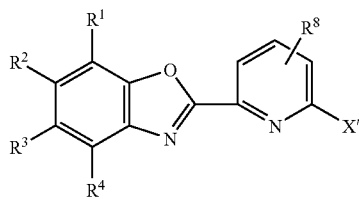

(IX)

wherein X' represents a halogen atom, a methanesulfonyloxy group or a p-toluenesulfonyloxy group, and a compound (X) represented by the following formula (X):

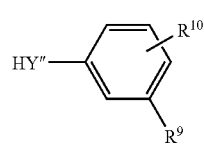

(X)

wherein $R^9$, $R^{10}$ and Y" have the same meanings as defined above, in a solvent in the presence of a base.

The third invention relates to a process for producing a compound represented by the formula (I-b):

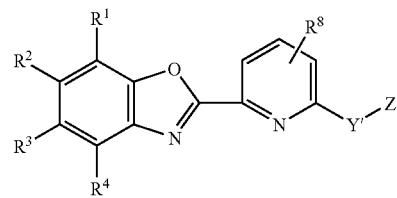

(I-b)

wherein $R^1$ to $R^4$, $R^8$, Y' and Z have the same meanings as defined above, which comprises reacting a compound (XII) represented by the following formula (XII):

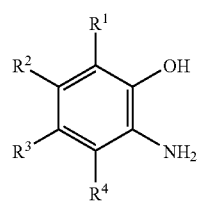

(XII)

wherein $R^1$ to $R^4$ have the same meanings as defined above, and a compound represented by the following formula (XIII):

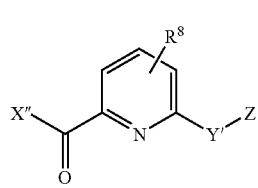

(XIII)

wherein $R^8$, Y' and Z have the same meanings as defined above, and

X" represents a halogen atom, a hydroxyl group or an alkoxy group having 1 to 4 carbon atoms, in a solvent in the presence of a base.

The fourth invention relates to a process for producing a compound (I-c) represented by the following formula (I-c):

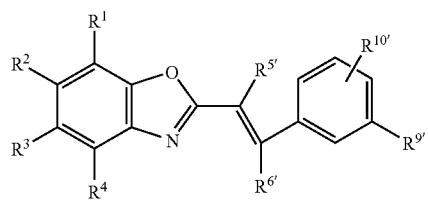

(I-c)

wherein $R^1$ to $R^4$ have the same meanings as defined above, $R^5$ represents an alkyl group having 1 to 6 carbon atoms, $R^{6'}$ represents a hydrogen atom, a hydroxyl group, a halogen atom or an alkyl group having 1 to 4 carbon atoms, $R^{9'}$ represents a hydrogen atom, a cyano group, a haloalkyl group having 1 to 4 carbon atoms, a haloalkoxy group having 1 to 4 carbon atoms, a nitro group or $R^{12}S(O)_n$, where $R^{12}$ and n have the same meanings as defined above, and $R^{10'}$ represents a hydrogen atom, a halogen atom, a haloalkyl group having 1 to 4 carbon atoms or a cyano group, or a compound (I-d) represented by the following formula (I-d):

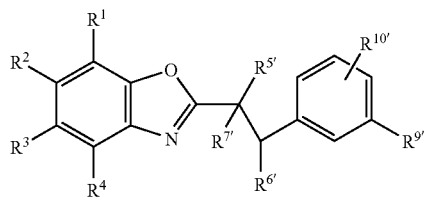

(I-d)

wherein $R^1$ to $R^4$, $R^{5'}$, $R^{6'}$, $R^{9'}$ and $R^{10'}$ have the same meanings as defined above, and $R^{7'}$ represents a hydrogen atom, a hydroxyl group, a halogen atom or a substituted sulfonyloxy group, which comprises reacting a compound (XII) represented by the following formula (XII):

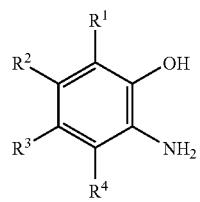

(XII)

wherein $R^1$ to $R^4$ have the same meanings as defined above, and a compound (XV-a) represented by the following formula (XV-a)

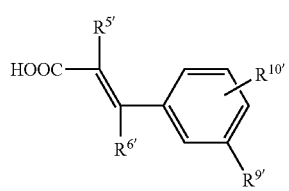

(XV-a)

wherein $R^{5'}$, $R^{6'}$, $R^{9'}$ and $R^{10'}$ have the same meanings as defined above, or a compound (XV-b) represented by the following formula (XV-b):

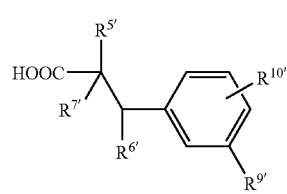

(XV-b)

wherein $R^{5'}$, $R^{6'}$, $R^{7'}$, $R^{9'}$ and $R^{10'}$ have the same meanings as defined above, in the presence of a base or an acid catalyst in a solvent.

The fifth invention relates to a process for producing the compound (I-c) which comprises dehydrating a compound represented by the following formula (I-d'):

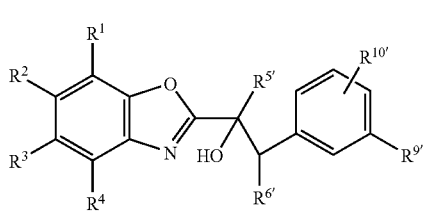

(I-d')

wherein $R^1$ to $R^4$, $R^{5'}$, $R^{6'}$, $R^{9'}$ and $R^{10'}$ have the same meanings as defined above.

The sixth invention relates to a process for producing the compound (I-c) which comprises reacting a compound (XVI) represented by the following formula (XVI):

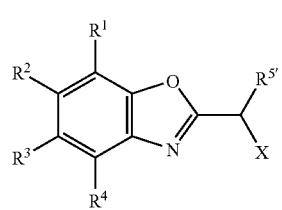

(XVI)

wherein $R^1$ to $R^4$ and $R^5$ have the same meanings as defined above, and

X represents a halogen atom, with triphenylphosphine in a solvent to produce a phosphonium salt, and then, reacting the resulting compound with a compound (XVII) represented by the following formula (XVII):

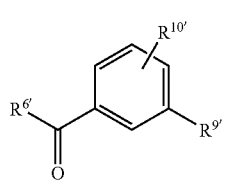

(XVII)

wherein $R^{6'}$, $R^{9'}$ and $R^{10'}$ have the same meanings as defined above, in the presence of a base.

The seventh invention relates to a process for producing a compound (I-e) represented by the following formula (I-e):

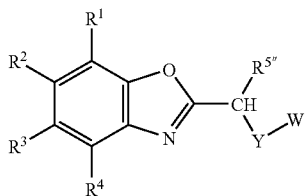
(I-e)

wherein $R^1$ to $R^4$, Y and W have the same meanings as defined above, and $R^{5'}$ represents an alkyl group having 1 to 6 carbon atoms, which is a compound where A is $CHR^{5'}$—Y in the above-mentioned formula (I), which comprises reacting a compound (IV) represented by the following formula (IV):

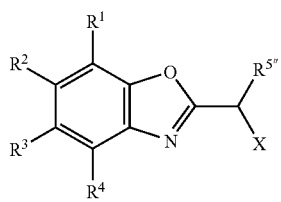
(IV)

wherein $R^1$ to $R^4$, $R^{5'}$ and X have the same meanings as defined above, with a compound (V) represented by the following formula (V):

HY—W (V)

wherein Y and W have the same meanings as defined above, in a solvent in the presence of a base.

The eighth invention relates to a process for producing the compound (I-e) which is a compound where A is $CHR^{5'}$—Y in the above-mentioned formula (I), which comprises reacting a compound (VI) represented by the following formula (VI):

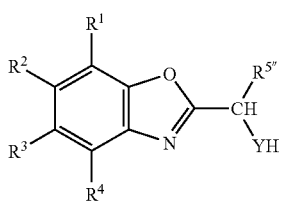
(VI)

wherein $R^1$ to $R^4$, $R^{5'}$ and Y have the same meanings as defined above, with a compound (VII) represented by the following formula (VII):

X—W (VII)

wherein W and X have the same meanings as defined above, in a solvent in the presence of a base.

The ninth invention relates to a process for producing a compound (I-f) represented by the following formula (I-f):

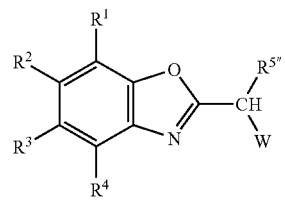
(I-f)

wherein $R^1$ to $R^4$, $R^{5'}$ and W have the same meanings as defined above, which is a compound where A is $CHR^{5'}$ in the above-mentioned formula (I), which comprises reacting the compound (IV) represented by the above-mentioned formula (IV) with a compound (VIII) represented the following formula (VIII):

H—W (VIII)

wherein W have the same meanings as defined above, in a solvent in the presence of a base.

The tenth invention relates to a herbicide containing the compound (I) represented by the above-mentioned formula (I) as an effective ingredient.

BEST MODE FOR CARRYING OUT THE INVENTION

In the following, the present invention is explained in detail.

The various kinds of substituents, etc. shown in the above-mentioned compound are as shown below.

Incidentally, in the explanation of the present invention, it is also shown as "a compound (numeral, symbol, etc)" with a numeral, symbol, etc. with parentheses attached to the chemical formula (for example, that shown by the formula (I) is also called to as a compound (I).). And as a compound (I), for example, in Tables 1 to 33 mentioned below, they are shown as a compound (1-a-1) to a compound (1-a-81) or a compound (1-d-1) to a compound (I-d-12) and the like.

In the above-mentioned formula (I), $R^1$ to $R^4$ may be the same or different from each other, and each represent a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, $R^{12}S(O)_n$, an alkoxycarbonyl group having 1 to 4 carbon atoms, or a carbonyl group, where $R^{11}$ and $R^{12}$ each represent an alkyl group having 1 to 6 carbon atoms, and n is an integer of 0 to 20, provided that the case where all are hydrogen atoms is excluded.

The alkyl group is a straight or branched one; preferably those having 1 to 4 carbon atoms; more preferably those having 1 to 3 carbon atoms. For example, there may be mentioned a methyl group, an ethyl group, and a propyl group.

The alkoxy group is a straight or branched one; preferably those having 1 to 4 carbon atoms; more preferably those having 1 to 3 carbon atoms. For example, there may be mentioned a methoxy group, an ethoxy group, a propyloxy group and an isopropyloxy group.

The haloalkyl group is a straight or branched one; preferably those having 1 to 4 carbon atoms; more preferably those having 1 to 3 carbon atoms. For example, there may be mentioned a chloromethyl group, a chloroethyl group and a trifluoromethyl group.

The haloalkoxy group is a straight or branched one; preferably those having 1 to 4 carbon atoms; more preferably those having 1 to 3 carbon atoms. For example, there may be mentioned a trifluoromethoxy group and a trifluoroethoxy group.

The halogen atom is a fluorine atom, a chlorine atom, a bromine atom and an iodine atom; preferably a chlorine atom.

$R^{12}$ in $R^{12}S(O)_n$ is a straight or branched alkyl group; preferably those having 1 to 4 carbon atoms; more preferably those having 1 to 3 carbon atoms. For example, there may be mentioned a methyl group and the like.

The alkoxy group in the alkoxycarbonyl group is a straight or branched one; preferably those having 1 to 3 carbon atoms; more preferably an ethoxy group.

n is an integer of 0 to 2; preferably 0 or 2.

In the above-mentioned formula (I), A represents a single bond, $CHR^5$—Y, $CR^5$=$CR^6$, $CR^{5'}$=$CR^{6'}$, $CR^5R^7$—$CHR^6$, $CR^{5'}R^{7'}$—$CHR^{6'}$ or $CHR^5$, where $R^5$ represents a hydrogen atom, an alkyl group having 1 to 6 carbon atoms and a haloalkyl group having 1 to 4 carbon atoms, $R^6$ and $R^7$ each represent a hydrogen atom, a hydroxyl group, an alkyl group having 1 to 6 carbon atoms or a halogen atom, $R^{5'}$ represents an alkyl group having 1 to 6 carbon atoms, $R^{6'}$ represents a hydrogen atom, a hydroxyl group, a halogen atom or an alkyl group having 1 to 4 carbon atoms, $R^{7'}$ represents a hydrogen atom, a hydroxyl group, a halogen atom or a substituted sulfonyloxy group, and Y represents O, S or NH.

As $R^5$, there may be mentioned a hydrogen atom, an alkyl group having 1 to 6 carbon atoms and a haloalkyl group having 1 to 4 carbon atoms.

The alkyl group is a straight or branched one, preferably those having 1 to 4 carbon atoms, more preferably those having 1 to 3 carbon atoms. For example, there may be mentioned a methyl group, an ethyl group and a propyl group.

The haloalkyl group is a straight or branched one, preferably those having 1 to 4 carbon atoms, more preferably those having 1 to 3 carbon atoms. For example, there may be mentioned a chloromethyl group, a chloroethyl group and a trifluoromethyl group.

$R^6$ and $R^7$ each represent a hydrogen atom, a hydroxyl group, an alkyl group having 1 to 6 carbon atoms or a halogen atom.

The alkyl group is a straight or branched one, preferably those having 1 to 4 carbon atoms, more preferably those having 1 to 3 carbon atoms. For example, there may be mentioned a methyl group, an ethyl group and a propyl group.

The halogen atom is a fluorine atom, a chlorine atom, a bromine atom or an iodine atom, preferably a chlorine atom.

$R^{5'}$ represents a hydrogen atom or an alkyl group having 1 to 6 carbon atoms. The alkyl group is a straight or branched one, and preferably those having 1 to 5 carbon atoms, more preferably those having 1 to 4 carbon atoms.

$R^{6'}$ represents a hydrogen atom, a hydroxyl group, a halogen atom or an alkyl group having 1 to 4 carbon atoms. The alkyl group is a straight or branched one, and preferably those having 1 to 3 carbon atoms.

$R^{7'}$ represents a hydrogen atom, a hydroxyl group, a halogen atom or a substituted sulfonyloxy group.

The halogen atom may be mentioned a fluorine atom, a chlorine atom, a bromine atom and an iodine atom, preferably a fluorine atom.

The substituent in the substituted sulfonyloxy group is an alkyl group having 1 to 4 carbon atoms or an unsubstituted phenyl group or a phenyl group substituted by an alkyl group having 1 to 4 carbon atoms. And, these alkyl groups are straight or branched ones, and preferably those having 1 to 3 carbon atoms, more preferably a methyl group.

(1) In the above-mentioned formula (I), when A is a single bond, $R^8$ in the formula (II) represents a haloalkyl group having 1 to 4 carbon atoms, an alkylsulfonyl group having 1 to 4 carbon atoms, a cyano group, a haloalkoxy group having 1 to 4 carbon atoms, a hydrogen atom or a halogen atom.

As the haloalkyl group having 1 to 4 carbon atoms, there may be mentioned a straight or branched one, preferably those having 1 to 3 carbon atoms. For example, there may be mentioned a chloromethyl group, a chloroethyl group and a trifluoromethyl group.

As the alkyl group in the alkylsulfonyl group having 1 to 4 carbon atoms, there may be mentioned a straight or branched one, preferably those having 1 to 3 carbon atoms. For example, there may be mentioned a methyl group, an ethyl group and a propyl group.

As the haloalkoxy group having 1 to 4 carbon atoms, there may be mentioned a straight or branched one, preferably those having 1 to 3 carbon atoms. For example, there may be mentioned a chloromethyl group, a chloroethyl group and a trifluoromethyl group.

Y' represents O, $S(O)_n$ or $NR^{13}$. In the formula, n is an integer of 0 to 2, $R^{13}$ represents a hydrogen atom or an alkoxy group having 1 to 4 carbon atoms.

As the alkoxy group having 1 to 4 carbon atoms, there may be mentioned a straight or branched one, preferably those having 1 to 3 carbon atoms. For example, there may be mentioned a methoxy group, an ethoxy group, a propyloxy group and an isopropyloxy group.

In the formula (X), Y" represents an oxygen atom or a sulfur atom.

Z in the formula (II) represents a substituent represented by the formula (III-1) or a hetero ring.

In the formula (III-1), $R^9$ represents a hydrogen atom, a halogen atom, a cyano group or a haloalkyl group having 1 to 4 carbon atoms.

As the halogen atom, there may be mentioned a fluorine atom, a chlorine atom, a bromine atom and an iodine atom, preferably a fluorine atom.

As the haloalkyl group having 1 to 4 carbon atoms, there may be mentioned a straight or branched one, preferably those having 1 to 3 carbon atoms, for example, there may be mentioned a chloromethyl group, a chloroethyl group and a trifluoromethyl group.

$R^{10}$ represents a hydrogen atom, an alkyl group having 1 to 4 carbon atoms, an alkoxy group having 1 to 4 carbon atoms, a halogen atom, or a haloalkyl group having 1 to 4 carbon atoms.

As the alkyl group having 1 to 4 carbon atoms, there may be mentioned a straight or branched one, preferably those having 1 to 3 carbon atoms. For example, there may be mentioned a methyl group, an ethyl group and a propyl group.

As the alkoxy group having 1 to 4 carbon atoms, there may be mentioned a straight or branched one, preferably those having 1 to 3 carbon atoms. For example, there may be mentioned a methoxy group, an ethoxy group, a propyloxy group and an isopropyloxy group.

As the halogen atom, there may be mentioned a fluorine atom, a chlorine atom, a bromine atom and an iodine atom, preferably a chlorine atom.

As the haloalkyl group having 1 to 4 carbon atoms, there may be mentioned a straight or branched one, preferably those having 1 to 3 carbon atoms. For example, there may be mentioned a chloromethyl group, a chloroethyl group and a trifluoromethyl group.

The hetero ring is a compound characterized in that it has an atom preferably selected from an oxygen atom, a sulfur atom and a nitrogen atom as a hetero ring atom, more preferably a furyl group, a thienyl group, a pyrazoly group, a pyrazolonyl group, an imidazoyl group, an oxazoyl group, an isoxazoyl group, a thiazoyl group, a 1,2,3-triazoyl group, a pyridyl group, a pyrinidinyl group, a pyrimidonyl group, a quinolyl group, a 3,4-methylenedioxyphenyl group, a benzoxazoyl group, a benzothiazoyl group, or a benzoimidazoyl group, more preferably an of W-1 to W-35 shown by the following formula:

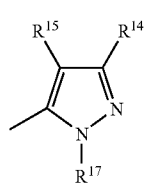
(W-1)

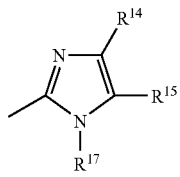
(W-2)

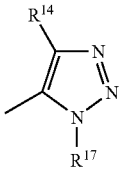
(W-3)

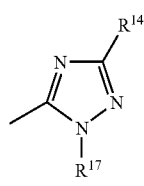
(W-4)

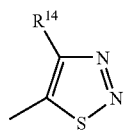
(W-5)

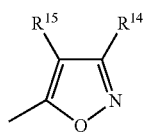
(W-6)

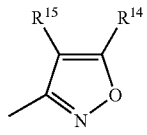
(W-7)

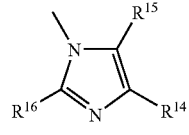
(W-8)

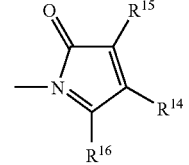
(W-9)

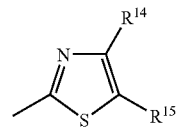
(W-10)

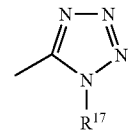
(W-11)

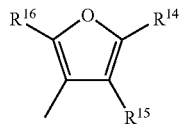
(W-12)

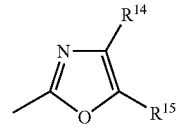
(W-13)

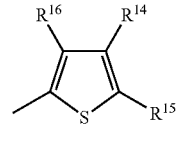
(W-14)

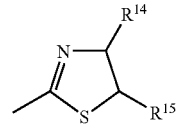
(W-15)

-continued
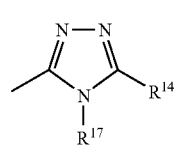 (W-16)
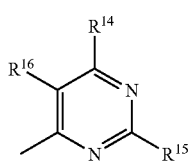 (W-17)
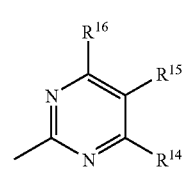 (W-18)
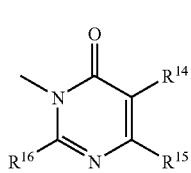 (W-19)
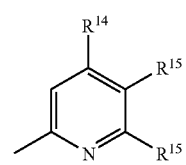 (W-20)
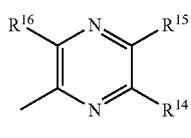 (W-21)
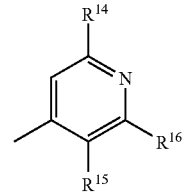 (W-22)
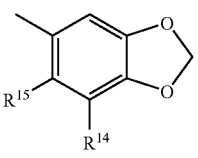 (W-23)
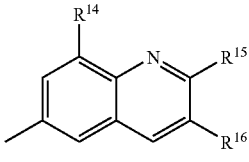 (W-24)
-continued
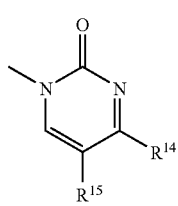 (W-26)
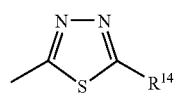 (W-27)
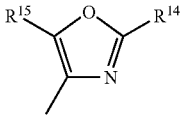 (W-28)
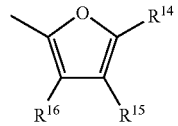 (W-29)
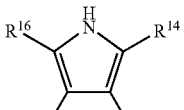 (W-30)
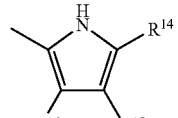 (W-31)
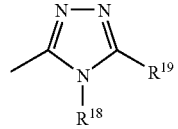 (W-32)
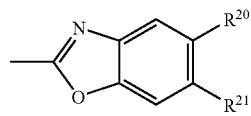 (W-33)
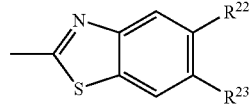 (W-34)
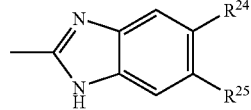 (W-35)

In the above-mentioned formulae of W-1 to W-35, $R^{14}$ represents a hydrogen atom, an alkyl group having 1 to 4 carbon atoms, a haloalkyl group having 1 to 4 carbon atoms, a nitro group, a cyano group or a halogen atom, preferably a haloalkyl group having 1 to 4 carbon atoms or a hydrogen atom, more preferably the haloalkyl group is a trifluoromethyl group.

$R^{15}$ and $R^{16}$ may be the same or different from each other, and each represent a hydrogen atom, an alkyl group having 1 to 4 carbon atoms, a haloalkyl group having 1 to 4 carbon atoms, a nitro group, a cyano group, an alkoxy group having 1 to 4 carbon atoms, having 1 to 4 carbon atoms a haloalkoxy group or an alkylthio group having 1 to 4 carbon atoms, preferably a haloalkyl group having 1 to 4 carbon atoms or a hydrogen atom, more preferably the haloalkyl group is a trifluoromethyl group.

$R^{17}$ represents a hydrogen atom, an alkyl group having 1 to 4 carbon atoms or a haloalkyl group having 1 to 4 carbon atoms, preferably a haloalkyl group having 1 to 4 carbon atoms. And, the alkyl group is preferably a methyl group.

$R^{18}$ represents an alkyl group having 1 to 4 carbon atoms or a hydrogen atom, $R^{19}$ represents a haloalkyl group having 1 to 4 carbon atoms, an alkyl group having 1 to 4 carbon atoms, a nitro group, a cyano group or a hydrogen atom, preferably a haloalkyl group having 1 to 4 carbon atoms. And, the alkyl group is preferably a methyl group, and the haloalkyl group is more preferably a trifluoromethyl group.

$R^{20}$ represents an alkyl group having 1 to 4 carbon atoms, a hydrogen atom, a haloalkyl group having 1 to 4 carbon atoms, a cyano group or a halogen atom, preferably a cyano group or a halogen atom, $R^{21}$ represents an alkyl group having 1 to 4 carbon atoms, a hydrogen atom, a haloalkyl group having 1 to 4 carbon atoms, a cyano group or a halogen atom, preferably an alkyl group having 1 to 4 carbon atoms or a hydrogen atom. And, the halogen atom is preferably a chlorine atom, and the alkyl group is preferably a methyl group.

$R^{22}$ represents an alkyl group having 1 to 4 carbon atoms, a hydrogen atom, a haloalkyl group having 1 to 4 carbon atoms, a cyano group or a halogen atom, preferably a cyano group or a halogen atom, $R^{23}$ represents an alkyl group having 1 to 4 carbon atoms, a hydrogen atom, a haloalkyl group having 1 to 4 carbon atoms or a cyano group, preferably an alkyl group having 1 to 4 carbon atoms or a hydrogen atom. And, the halogen atom is preferably a chlorine atom, and the alkyl group is preferably a methyl group.

$R^{24}$ represents an alkyl group having 1 to 4 carbon atoms, a hydrogen atom, a haloalkyl group having 1 to 4 carbon atoms, a cyano group or a halogen atom, preferably a cyano group or a halogen atom, $R^{25}$ represents an alkyl group having 1 to 4 carbon atoms, a hydrogen atom, a haloalkyl group having 1 to 4 carbon atoms, a cyano group or a halogen atom, preferably an alkyl group having 1 to 4 carbon atoms or a hydrogen atom. And, this halogen atom is preferably a chlorine atom, and the alkyl group is preferably a methyl group.

In the formula (I), as a compound (I) wherein A is a single bond, there may be mentioned those in which the above-mentioned various kinds of substituents are combined, and further preferred are as follows.

(i) In a compound represented by the following formula (I-a):

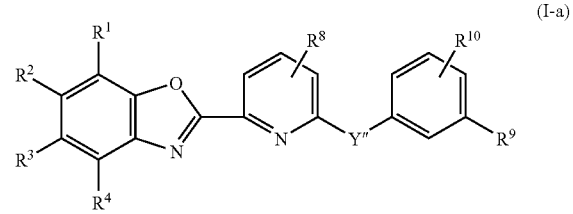

(I-a)

a compound (I-a) wherein $R^1$ to $R^4$, $R^8$ and $R^{10}$ are hydrogen atoms, $R^9$ is a haloalkyl group having 1 to 4 carbon atoms, and Y" is an oxygen atom. For example, there may be mentioned a compound I-a-1 shown in Table 1 and the like.

(ii) A compound (I-a) wherein $R^1$, $R^2$, $R^4$, $R^8$ and $R^{10}$ are hydrogen atoms, $R^3$ is a halogen atom, $R^9$ is a haloalkyl group having 1 to 4 carbon atoms, and Y" is an oxygen atom. For example, there may be mentioned compounds I-a-2, I-a-3 and the like shown in Table 1.

(iii) A compound (I-a) wherein $R^1$, $R^2$, $R^4$, $R^8$ and $R^{10}$ are hydrogen atoms, $R^3$ is an alkoxy group having 1 to 4 carbon atoms, $R^9$ is a haloalkyl group having 1 to 4 carbon atoms, and Y" is an oxygen atom. For example, there may be mentioned a compound I-a-4 and the like shown in Table 1.

(iv) A compound (I-a) wherein $R^2$ is a halogen atom, $R^1$, $R^3$, $R^4$, $R^8$ and $R^{10}$ are hydrogen atoms, $R^9$ is a haloalkyl group having 1 to 4 carbon atoms, and Y" is an oxygen atom. For example, there may be mentioned a compound I-a-6 and the like shown in Table 1.

(v) A compound (I-a) wherein $R^2$ and $R^{10}$ are halogen atoms, $R^1$, $R^3$, $R^4$ and $R^8$ are hydrogen atoms, $R^9$ is a haloalkyl group having 1 to 4 carbon atoms, and Y" is an oxygen atom. For example, there may be mentioned a compound I-a-7 and the like shown in Table 1.

(vi) A compound (I-a) wherein $R^1$, $R^2$, $R^4$, $R^8$ and $R^{10}$ are hydrogen atoms, $R^3$ and $R^9$ are haloalkyl groups having 1 to 4 carbon atoms, and Y" is an oxygen atom. For example, there may be mentioned a compound I-a-13 and the like shown in Table 1.

(vii) A compound (I-a) wherein $R^1$, $R^2$, $R^4$, $R^8$ and $R^{10}$ are hydrogen atoms, $R^3$ is a cyano group, $R^9$ is a haloalkyl group having 1 to 4 carbon atoms, and Y" is an oxygen atom. For example, there may be mentioned a compound I-a-18 shown in Table 1.

(2) In the formula (I), when A is $CR^{5'}=CR^{6'}$ or $CR^{5'}R^{7'}$—$CHR^{6'}$, W represents a benzene ring shown by the following formula (III-2).

(III-2)

$R^{9'}$ is a haloalkyl group having 1 to 4 carbon atoms, a cyano group, a hydrogen atom, $R^{12}S(O)_n$, a nitro group or having 1 to 4 carbon atoms a haloalkoxy group.

The haloalkyl group is a straight or branched one, and preferably those having 1 to 3 carbon atoms, more preferably a trifluoromethyl group.

$R^{12}$ and n in $R^{12}(O)_n$ have the same meanings as defined above.

The haloalkoxy group is a straight or branched one, and preferably those having 1 to 3 carbon atoms, more preferably a trifluoromethoxy group.

$R^{10'}$ is a hydrogen atom, a halogen atom, a cyano group or a haloalkyl group having 1 to 4 carbon atoms.

The halogen atom may be mentioned a fluorine atom, a chlorine atom, a bromine atom and an iodine atom, and preferably a fluorine atom or a chlorine atom.

The haloalkyl group is a straight or branched one, and preferably those having 1 to 3 carbon atoms, more preferably a trifluoromethyl group.

A represents $CR^{5'}=CR^{6'}$ or $CR^{5'}R^{7'}-CHR^{6'}$, where as X in the compound represented by the formula (XVII) to be used in the preparation of the compound represented by the formula (I-c), there may be mentioned a halogen atom, and preferably a chlorine atom or a bromine atoms.

In the above-mentioned formula (I), as a compound (I) represented by the formula (I-c):

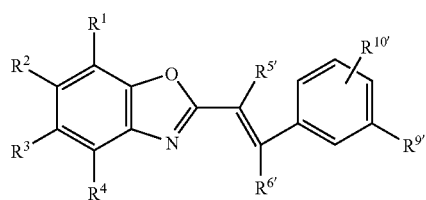

(I-c)

wherein $R^1$ to $R^4$ and $R^{5'}$ to $R^{6'}$ and $R^{9'}$ to $R^{10'}$ have the same meanings as defined above, where A is $CR^{5'}=CR^{6'}$, those in which the above-mentioned various kinds of substituents are combined are mentioned, and those preferred in medical effects are the following.

(i) A compound (I-c) wherein $R^1$ to $R^4$, $R^{5'}$, $R^{6'}$, $R^{10'}$ are a hydrogen atom, and $R^{9'}$ is a haloalkyl group having 1 to 4 carbon atoms. For example, there may be mentioned a compound I-c-1 mentioned in Table 24 shown below and the like.

(ii) A compound (I-c) wherein $R^1$, $R^3$, $R^4$, $R^{6'}$ and $R^{10'}$ area hydrogen atoms, $R^2$ is a nitro group, $R^{9'}$ is a haloalkyl group having 1 to 4 carbon atoms, and $R^{5'}$ is an alkyl group having 1 to 6 carbon atoms. For example, there may be mentioned a compound I-c-15 mentioned in Table 24 shown below and the like.

(iii) A compound (I-c) wherein $R^1$, $R^2$, $R^4$, $R^{6'}$ and $R^{10'}$ are hydrogen atoms, $R^3$ is a halogen atom, $R^{9'}$ is a haloalkyl group having 1 to 4 carbon atoms, and $R^{5'}$ is an alkyl group having 1 to 6 carbon atoms. For example, there may be mentioned compounds I-c-40, I-c-42, I-c-44, I-c-53, I-c-55, I-c-57, I-c-67 mentioned in Table 24 shown below and the like.

(iv) A compound (I-c) wherein $R^1$, $R^2$, $R^4$ and $R^{6'}$ are hydrogen atoms, $R^3$ is a halogen atom, $R^{9'}$ is a haloalkyl group having 1 to 4 carbon atoms, $R^{10'}$ is a halogen atom, and $R^{5'}$ is an alkyl group having 1 to 6 carbon atoms. For example, there may be mentioned a compound I-c-4 mentioned in Table 24 shown below and the like.

(v) A compound (I-c) wherein $R^1$, $R^2$, $R^4$, $R^{6'}$ and $R^{10'}$ are hydrogen atoms, $R^3$ is a nitro group, $R^{9'}$ is a haloalkyl group having 1 to 4 carbon atoms, and $R^{5'}$ is an alkyl group having 1 to 6 carbon atoms. For example, there may be mentioned compounds I-c-72, I-c-74 mentioned in Table 24 shown below and the like.

(vi) A compound (I-c) wherein $R^1$, $R^2$, $R^4$, $R^{6'}$ and $R^{10'}$ are hydrogen atoms, $R^3$ is an alkyl group having 1 to 4 carbon atoms, $R^{9'}$ is a haloalkyl group having 1 to 4 carbon atoms, and $R^{5'}$ is an alkyl group having 1 to 6 carbon atoms. For example, there may be mentioned a compound I-c-76 mentioned in Table 24 shown below and the like.

(vii) A compound (I-c) wherein $R^1$, $R^2$, $R^4$, $R^{6'}$ and $R^{10'}$ are hydrogen atoms, $R^3$ is a cyano group, $R^{9'}$ is a haloalkyl group having 1 to 4 carbon atoms, $R^{5'}$ is an alkyl group having 1 to 6 carbon atoms. For example, there may be mentioned compounds I-c-81, I-c-83 mentioned in Table 24 shown below and the like.

(viii) A compound (I-c) wherein $R^1$, $R^2$, $R^4$, $R^{6'}$ and $R^{10'}$ are hydrogen atoms, $R^3$ is a haloalkyl group having 1 to 4 carbon atoms, $R^{9'}$ is a haloalkyl group having 1 to 4 carbon atoms, and $R^{5'}$ is an alkyl group having 1 to 6 carbon atoms. For example, there may be mentioned compounds I-c-86, I-c-88 mentioned in Table 24 shown below and the like.

(ix) A compound (I-c) wherein $R^1$, $R^4$, $R^{6'}$ and $R^{10'}$ are hydrogen atoms, $R^2$ and $R^3$ are halogen atoms, $R^{9'}$ is a haloalkyl group having 1 to 4 carbon atoms, $R^{5'}$ is an alkyl group having 1 to 6 carbon atoms. For example, there may be mentioned compounds I-c-111, I-c-113 mentioned in Table 24 shown below and the like.

(x) A compound (I-c) wherein $R^1$, $R^4$, $R^{6'}$ and $R^{10'}$ are hydrogen atoms, $R^2$ is an alkyl group having 1 to 4 carbon atoms, $R^3$ is a halogen atom, $R^{9'}$ is a haloalkyl group having 1 to 4 carbon atoms, and $R^{5'}$ is an alkyl group having 1 to 6 carbon atoms. For example, there may be mentioned a compound I-c-131 mentioned in Table 24 shown below and the like.

(xi) A compound (I-c) wherein $R^1$, $R^4$, $R^{6'}$ and $R^{10'}$ are hydrogen atoms, $R^2$ is a halogen atom, $R^3$ is a cyano group, $R^{9'}$ is a haloalkyl group having 1 to 4 carbon atoms, and $R^{5'}$ is an alkyl group having 1 to 6 carbon atoms. For example, there may be mentioned compounds I-c-135, I-c-137, I-c-139, I-c-141, I-c-143, I-c-145 mentioned in Table 24 shown below and the like.

Moreover, in the above-mentioned formula (I), as a compound (I) represented by the formula (I-d):

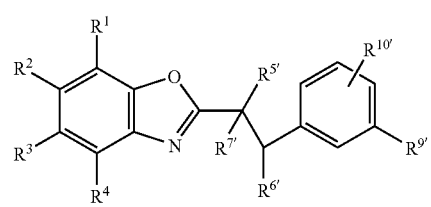

(I-d)

wherein $R^1$ to $R^4$ and $R^{5'}$ to $R^{7'}$ and $R^{9'}$ to $R^{10'}$ have the same meanings as defined above, where A is $CR^{5'}R^{7'}-CHR^{6'}$, those in which the above-mentioned various kinds of substituents are combined are mentioned, and those preferred in medical effects are the following.

(xii) A compound (I-d) wherein $R^1$, $R^2$, $R^4$ and $R^{6'}$ are hydrogen atoms, $R^3$, $R^{10'}$ and $R^{7'}$ are halogen atoms, $R^{9'}$ is a haloalkyl group having 1 to 4 carbon atoms, and $R^{5'}$ is an alkyl group having 1 to 6 carbon atoms. For example, there may be mentioned a compound I-d-13 mentioned in Table 25 shown below and the like.

(3) In the formula (I), when A is $CHR^5$—Y, $CR^5$=$CR^6$, $CR^5R^7$—$CHR^6$ or $CHR^5$, W represents a hetero ring.

W represents a hetero ring having the same meaning as defined above.

In the formula (I), as a compound (I) represented by the formula (I-e) where A represents $CHR^5$—Y, $CR^5$=$CR^6$, $CR^5R^7$—$CHR^6$ or $CHR^5$, and as the compound (I) wherein W is a hetero ring, those in which the above-mentioned various kinds of substituents are combined are mentioned, and those preferred in medical effects are the following.

(i) In a compound represented by the following formula (I-e):

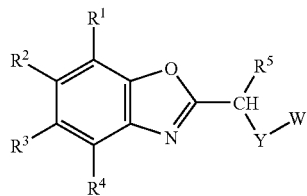

wherein $R^1$ to $R^4$, $R^5$, Y and W have the same meanings as defined above, a compound (I-e) wherein $R^1$, $R^2$ and $R^4$ are hydrogen atoms, $R^3$ is a halogen atom, $R^5$ is an alkyl group having 1 to 6 carbon atoms, Y is an oxygen atom, and a hetero ring W is shown by W-1. For example, there may be mentioned a compound (I-e-2) mentioned in Table 28 shown below and the like.

(ii) A compound (I-e) wherein $R^1$ and $R^4$ are hydrogen atoms, $R^2$ is a halogen atom, $R^3$ is a cyano group, $R^5$ is an alkyl group having 1 to 6 carbon atoms, Y is an oxygen atom, and a hetero ring W is shown by W-1. For example, there may be mentioned compounds (I-e-10), (I-e-11) mentioned in Table 28 shown below and the like.

(iii) A compound (I-e) wherein $R^1$, $R^2$ and $R^4$ are hydrogen atoms, $R^3$ is a halogen atom, $R^5$ is an alkyl group having 1 to 6 carbon atoms, Y is a sulfur atom, and a hetero ring W is shown by W-1. For example, there may be mentioned a compound (I-e-12) mentioned in Table 28 shown below and the like.

(iv) A compound (I-e) wherein $R^1$ and $R^4$ are hydrogen atoms, $R^2$ is a halogen atom, $R^3$ is a cyano group, $R^5$ is an alkyl group having 1 to 6 carbon atoms, Y is an oxygen atom, and a hetero ring W is shown by W-6. For example, there may be mentioned a compound (I-e-28) mentioned in Table 28 shown below and the like.

(v) A compound (I-e) wherein $R^1$ and $R^4$ are hydrogen atoms, $R^2$ is a halogen atom, $R^3$ is a cyano group, $R^5$ is an alkyl group having 1 to 6 carbon atoms, Y is an oxygen atom, and a hetero ring W is shown by W-7. For example, there may be mentioned a compound (I-e-40) mentioned in Table 28 shown below and the like.

(vi) A compound (I-e) wherein $R^1$, $R^2$ and $R^4$ are hydrogen atoms, $R^3$ is a halogen atom, $R^5$ is an alkyl group having 1 to 6 carbon atoms, Y is an oxygen atom, and a hetero ring W is shown by W-17. For example, there may be mentioned compounds (I-e-64), (I-e-66) mentioned in Table 28 shown below and the like.

(vii) A compound (I-e) wherein $R^1$ and $R^4$ are hydrogen atoms, $R^2$ is a halogen atom, $R^3$ is a cyano group, $R^5$ is an alkyl group having 1 to 6 carbon atoms, Y is an oxygen atom, and a hetero ring W is shown by W-17. For example, there may be mentioned a compound (I-e-65) mentioned in Table 28 shown below and the like.

(viii) A compound (I-e) wherein $R^1$, $R^2$ and $R^4$ are hydrogen atoms, $R^3$ is a cyano group, $R^5$ is an alkyl group having 1 to 6 carbon atoms, Y is an oxygen atom, and a hetero ring W is shown by W-17. For example, there may be mentioned a compound (I-e-70) mentioned in Table 28 shown below and the like.

(ix) In a compound represented by the formula (I-f):

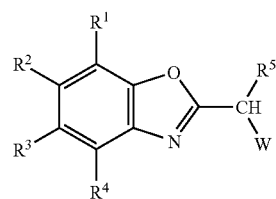

wherein $R^1$ to $R^4$, $R^5$ and W have the same meanings as defined above, a compound wherein $R^1$, $R^2$ and $R^4$ are hydrogen atoms, $R^3$ is a halogen atom, $R^5$ is an alkyl group having 1 to 6 carbon atoms, and a hetero ring W is a compound (I-f) shown by W-19. For example, there may be mentioned a compound (I-f-9) mentioned in Table 29 shown below and the like.

Next, Synthetic methods of the compound (I) according to the present invention are explained in more detail by classifying (1) the case where A is a single bond, (2) the case where A is $CR^{5'}$=$CR^{6'}$ or $CR^{5'}R^{7'}$—$CHR^{6'}$, and (3) the case where A is $CHR^5$—Y, $CR^5$=$CR^6$, $CR^5R^7$—$CHR^6$ or $CHR^5$.

(1) The Case where a is a Single Bond

The compound (I) can be synthesized according to either of the methods of Synthetic method 1-1, 1-2 or 1-3 shown below.

(Synthetic Method 1-1)

The compound (I-a) can be produced by reacting a compound (IX) and a compound (X) as shown below in a solvent.

And the reaction is preferably carried out in the presence of a base.

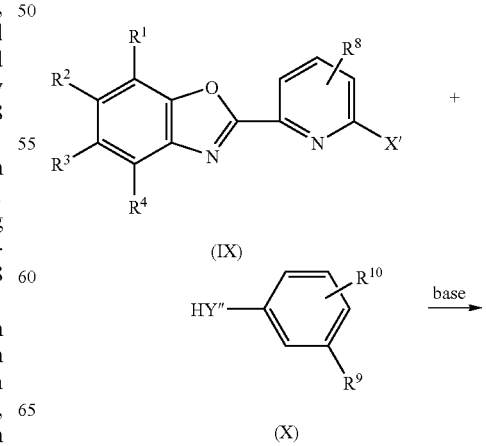

-continued

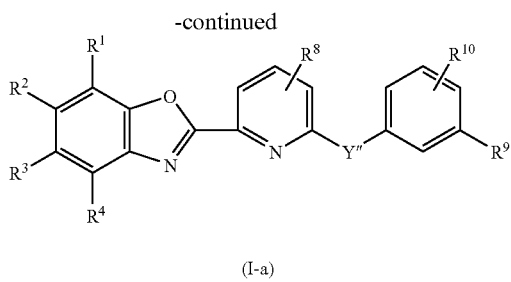

(I-a)

wherein $R^1$ to $R^4$, $R^8$ to $R^{10}$, X' and Y" have the same meanings as defined above.

The compound (IX) can be easily produced by reacting 2-aminophenol which is produced by the method as disclosed in Japanese Provisional Patent Publication No. 45735/1998, Heterocycle, vol. 41, pp. 477-485 (1995), Synthetic Communication, vol. 19, pp. 2921-2924 (1989), Journal of Medicinal Chemistry, vol. 30, pp. 400-405 (1987), Journal of Medicinal Chemistry, pp. 1480-1498 (1956) and the like, with 2-halopicolinic acids.

As a solvent to be used for the synthesis of the compound (I-a), it is not specifically limited so long as it does not pertain the present reaction, and there may be mentioned, for example, ethers such as diethylether, tetrahydrofuran, dioxane, etc.; Dipolar aprotic solvents such as N,N-dimethylformamide dimethylsulfoxide, etc.; aromatic hydrocarbons such as benzene, toluene, xylene, etc.; nitrites such as acetonitrile, etc.; ketones such as acetone, methyl ethyl ketone, etc.; and a mixed solvent of the above solvents, etc.

As a kind of the base to be used for the production of the compound (I-a), there may be mentioned, for example, organic bases such as triethylamine, pyridine, 4-N,N-dimethylaminopyridine, N,N-dimethylaniline, 1,4-diazabicyclo[2.2.2]octane, 1,8-diazabicyclo[5.4.0]undeca-7-ene, etc.; alkali metal alkoxides; alkoxides such as sodium methoxide, sodium ethoxide, potassium-t-butoxide, etc.; inorganic bases such as sodium hydride, potassium hydride, sodium amide, sodium hydroxide, potassium hydroxide, potassium carbonate, sodium carbonate, potassium hydrogen carbonate, sodium hydrogen carbonate, etc.; lithium diisopropylamide, and bistrimethylsilyl lithium amide.

As a kind of the acid catalyst, there may be mentioned, for example, mineral acids such as hydrochloric acid, sulfuric acid, nitric acid, etc.; organic acids such as formic acid, acetic acid, propionic acid, methanesulfonic acid, benzenesulfonic acid, p-toluenesulfonic acid, etc.; acid addition salts of amine such as pyridine hydrochloride, triethylamine hydrochloride, etc.; metal halides such as titanium tetrachloride, zinc chloride, ferrous chloride, ferric chloride, etc.; Lewis acids such as boron trifluoride.etherate, etc.

An amount of the acid catalyst to be used is 0.001 to 1 mole per mole of the compound (IX-1).

In the production of the compound (I), it is carried out with a reaction concentration of 5 to 80%.

In the production method, a ratio of the base to be used may be 0.5 to 2 moles per mole of the compound (IX-1), preferably 1 to 1.2 mole.

The reaction temperature is not specifically limited so long as it is carried out at a boiling point of the solvent to be used or lower, and usually carried out at 0 to 110° C.

The reaction time may vary depending on the above-mentioned density and temperature, and it is usually carried out for 0.5 to 24 hours.

(Synthetic Method 1-2)

The compound (I-b) can be produced as shown below by reacting a compound (XII) and a compound (XIII) or its reactive compound, in a solvent, by using a base or an acid catalyst if necessary.

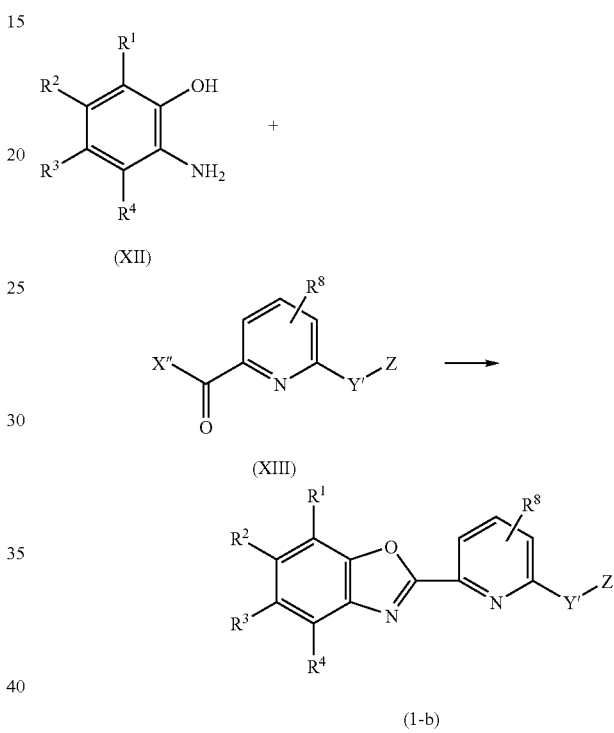

wherein $R^1$ to $R^4$, $R^8$, Y' and Z have the same meanings as defined above, X" represents a halogen atom, a hydroxyl group or an alkoxy group having 1 to 4 carbon atoms.

The compound (XIII) can be easily produced by reacting 2-halopicolines and phenols, thiphenols according to the conventional manner.

As a solvent to be used for the synthesis of the compound (I-b), it is not specifically limited so long as it does not pertain the present reaction, for example, ethers such as diethyl ether, tetrahydrofuran, dioxane, etc.; Dipolar aprotic solvents such as N,N-dimethylformamide, dimethylsulfoxide, etc.; aromatic hydrocarbons such as benzene, toluene, xylene, etc.; nitriles such as acetonitrile, etc.; ketones such as acetone, methyl ethyl ketone, etc.; and a mixed solvent of the above solvents, etc.

As a kind of the base to be used for the production of the compound (I-b), there may be mentioned, for example, organic bases such as triethylamine, pyridine, 4-N,N-dimethylaminopyridine, N,N-dimethylaniline, 1,4-diazabicyclo[2.2.2]octane, 1,8-diazabicyclo[5.4.0]undeca-7-ene, etc.; alkali metal alkoxides; alkoxides such as sodium methoxide, sodium ethoxide, potassium-t-butoxide, etc.; inorganic bases such as sodium hydride, potassium hydride, sodium amide, sodium hydroxide, potassium hydroxide, potassium carbonate, sodium carbonate, potassium hydrogen carbonate, sodium hydrogen carbonate, etc.; lithium diisopropylamide, bistrimethylsilyl lithium amide.

As a kind of the acid catalyst, there may be mentioned, for example, mineral acids such as hydrochloric acid, sulfuric acid, nitric acid, etc.; organic acids such as formic acid, acetic acid, propionic acid, methanesulfonic acid, benzenesulfonic acid, p-toluenesulfonic acid, etc.; acid addition salts of amines such as pyridine hydrochloride, triethylamine hydrochloride, etc.; metal halides such as titanium tetrachloride, zinc chloride, ferrous chloride, ferric chloride, etc.; Lewis acids such as boron trifluoride.etherate, etc.

An amount of the acid catalyst to be used is 0.001 to 1 mol per mol of the compound (XII).

In the production of the compound (I), it is carried out with a reaction concentration of 5 to 80%.

In the production method, a ratio of the base to be used may be 0.5 to 2 moles per mole of the compound (XII), preferably 1 to 1.2 mole.

The reaction temperature is not specifically limited so long as it is carried out at a boiling point of the solvent to be used or lower, and usually carried out at 0 to 110° C.

The reaction time may vary depending on the above-mentioned density and temperature, and it is usually carried out for 0.5 to 24 hours.

(Synthetic Method 1-3)

The compound (I-a) can be further produced as shown below by reacting a compound (XIV) and a compound (X) or its reactive compound, in a solvent by using a base.

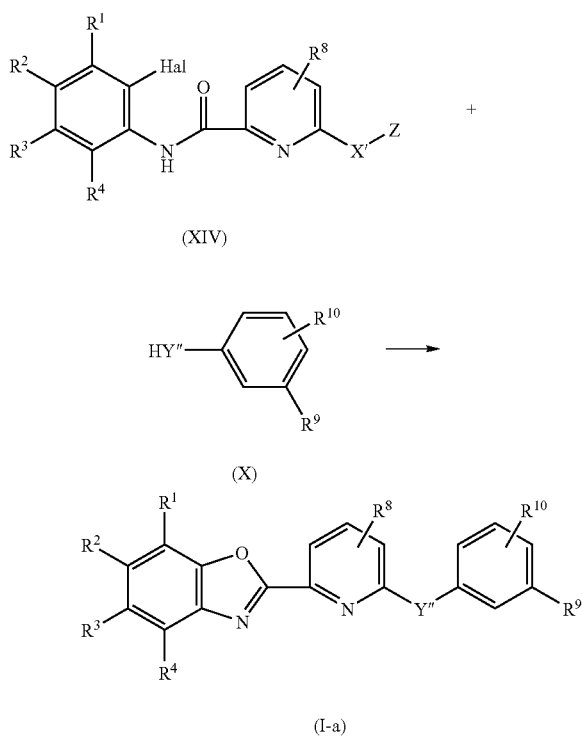

wherein $R^1$ to $R^4$, $R^8$ to $R^{10}$, X' and Y" have the same meanings as defined above; and Hal is a halogen atom.

As the solvent to be used for the synthesis of the compound (I-a), it is not specifically limited so long as it does not pertain the present reaction, for example, ethers such as diethyl ether, tetrahydrofuran, dioxane, etc.; dipolar aprotic solvents such as N,N-dimethylformamide, dimethylsulfoxide, etc.; aromatic hydrocarbons such as benzene, toluene, xylene, etc.; nitrites such as acetonitrile, etc.; ketones such as acetone, methyl ethyl ketone, etc.; and a mixed solvent of the above solvents, etc.

As a kind of the base to be used for the production of the compound (I-a), there may be mentioned, for example, organic bases such as triethylamine, pyridine, 4-N,N-dimethylaminopyridine, N,N-dimethylaniline, 1,4-diazabicyclo[2.2.2]octane, 1,8-diazabicyclo[5.4.0]undeca-y-ene, etc.; alkali metal alkoxides; alkoxides such as sodium methoxide, sodium ethoxide, potassium-t-butoxide, etc.; inorganic bases such as sodium hydride, potassium hydride, sodium amide, sodium hydroxide, potassium hydroxide, potassium carbonate, sodium carbonate, potassium hydrogen carbonate, sodium hydrogen carbonate, etc.; lithium diisopropylamide, bistrimethylsilyl lithium amide.

In the production of the compound (I), it is carried out with a reaction concentration of 5 to 80%.

In the production method, a ratio of the base to be used may be 0.5 to 2 moles per mole of the compound (XIV), preferably 1 to 1.2 mole.

The reaction temperature is not specifically limited so long as it is carried out at a boiling point of the solvent to be used or lower, and usually carried out at 0 to 110° C.

The reaction time may vary depending on the above-mentioned density and temperature, and it is usually carried out for 0.5 to 24 hours.

Thus, as the compound (I) obtained by Synthetic methods 1-1 to 1-3, there may be mentioned a compound (I-a) as shown compounds I-a-1 to I-a-84 and the like in Table 1 mentioned below, and a compound (I-b) as shown compounds W-1 to W-35 in Tables 2 to 21 mentioned below.

In a compound shown by compounds W-3-1 to W-35-1, as shown in Tables 2 to 21, as a compound W-1, there may be mentioned, for example, a compound (W-1-1) and the like; and as a compound W-2, there may be mentioned a compound (W-2-1) and the like. (2) In the formula (I), when A is $CR^{5'}=CR^{6'}$ or $CR^{5'}R^{7'}—CHR^{6'}$, the compound (I-c) or (I-d) can be synthesized according to either of the methods of Synthetic method 2-1, 2-2 or 2-3 shown below. (Synthetic method 2-1)

The compound (I-c) and the compound (I-d) among the compound (I) can be synthesized as shown below by reacting a compound (XII) and a compound (XV-a) or its carboxylic acid compound, or a compound (XV-b) or its carboxylic acid compound in the presence of a base or an acid catalyst in a solvent.

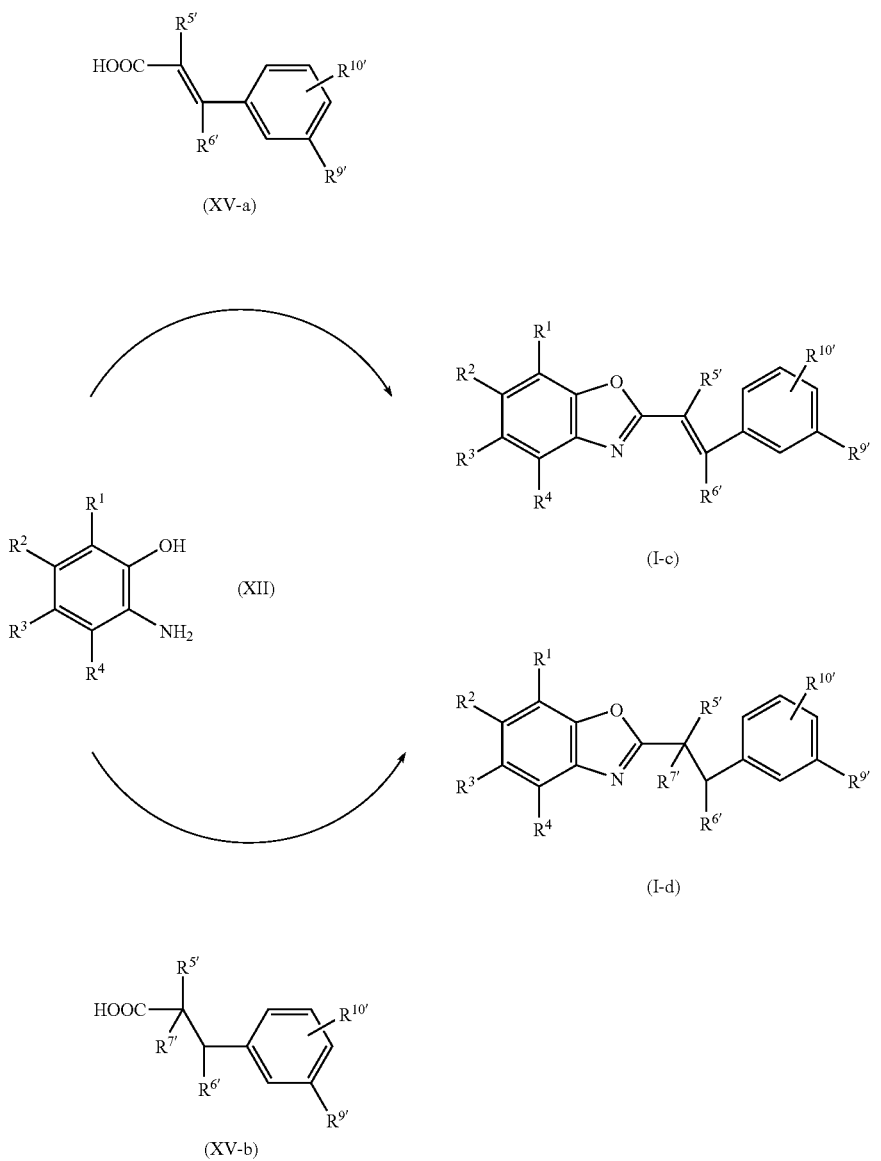

wherein $R^1$ to $R^4$, $R^{5'}$, $R^{6'}$, $R^{7'}$, $R^{9'}$ and $R^{10'}$ have the same meanings as defined above.

The compound (XV-a) and the compound (XV-b) can be easily produced as shown below by using α-halo-substituted alkanoic acid ester (a compound (XVIII)) as a starting material, subjecting to Arbusow reaction or Horner reaction using triethyl phosphite to obtain a compound (XV-a') through a compound (XIX), and the compound (XV-a) can be obtained by hydrolysis of the above and the compound (XV-b') can be easily produced with a reducing agent.

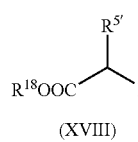

-continued

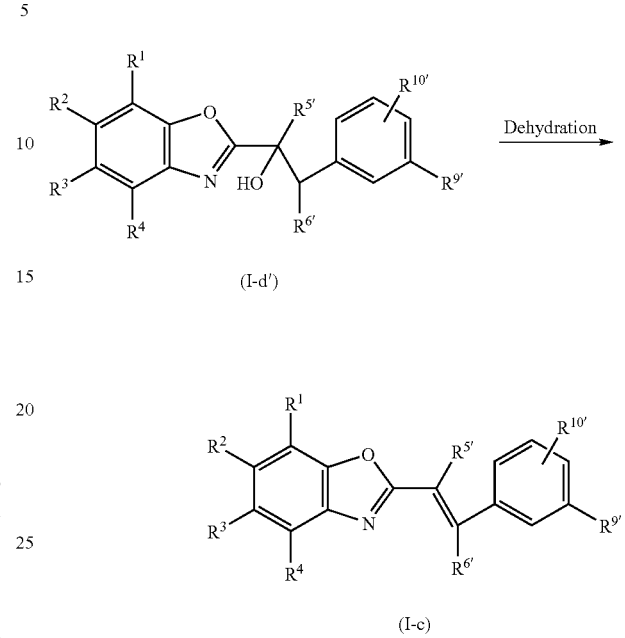

(XV-a)

(XV-b')

wherein $R^{5'}$, $R^{6'}$, $R^{9'}$ and $R^{10'}$ have the same meanings as defined above, $R^{18}$ represents the alkyl group or a phenyl group, and Hal represents a halogen atom.

As a kind of the base to be used, there may be mentioned, for example, organic bases such as triethylamine, pyridine, 4-N,N-dimethylaminopyridine, N,N-dimethylaniline, 1,4-diazabicyclo[2.2.2]octane, 1,8-diazabicyclo[5.4.0]undeca-7-ene, etc.; alkali metal alkoxides; alkoxides such as sodium methoxide, sodium ethoxide, potassium-t-butoxide, etc.; inorganic bases such as sodium hydride, potassium hydride, sodium amide, sodium hydroxide, potassium hydroxide, potassium carbonate, sodium carbonate, potassium hydrogen carbonate, sodium hydrogen carbonate, etc.; lithium diisopropylamide, and bistrimethylsilyl lithium amide.

As a kind of the base to be used for the production of the compound (I-a), there may be mentioned, for example, organic bases such as triethylamine, pyridine, 4-N,N-dimethylaminopyridine, N,N-dimethylaniline, 1,4-diazabicyclo[2.2.2]octane, 1,8-diazabicyclo[5.4.0]undeca-7-ene, etc.; alkali metal alkoxides; alkoxides such as sodium methoxide, sodium ethoxide, potassium-t-butoxide, etc.; inorganic bases such as sodium hydride, potassium hydride, sodium amide, sodium hydroxide, potassium hydroxide, potassium carbonate, sodium carbonate, potassium hydrogen carbonate, sodium hydrogen carbonate, etc.; lithium diisopropylamide, bistrimethylsilyl lithium amide.

As a kind of the acid catalyst, there may be mentioned, for example, mineral acids such as hydrochloric acid, sulfuric acid, nitric acid, etc.; oganic acids such as formic acid, acetic acid, propionic acid, methanesulfonic acid, benzenesulfonic acid, p-toluenesulfonic acid, etc.; acid addition salts of amines such as pyridine hydrochloride, triethylamine hydrochloride, etc.; metal halides such as titanium tetrachloride, zinc chloride, ferrous chloride, ferric chloride, etc.; Lewis acids such as boron trifluoride.etherate, etc.

An amount of the base catalyst or the acid catalyst to be used is 0.001 to 1 mole per mole of a compound (XII).

(Synthetic Method 2-2)

The compound (I-c) can be synthesized by dehydrating the compound (I-d').

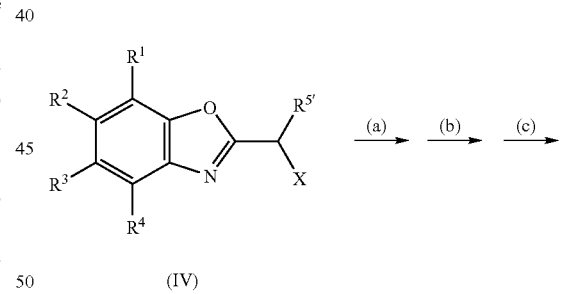

(I-d')

(I-c)

wherein $R^1$ to $R^4$, $R^{5'}$, $R^{6'}$, $R^{9'}$ and $R^{10'}$ have the same meanings as defined above.

The compound (I-d') can be produced by, for example, as shown below, subjecting the compound (IV) to successively (a) acetylation, (b) hydrolysis, and (c) oxidation of a hydroxyl group to obtain a compound (XX), and then, reacting it with a compound (XXI).

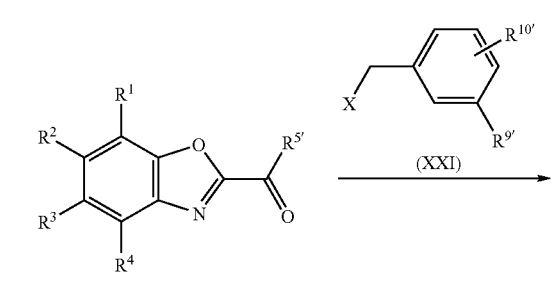

(IV)

(XX)

-continued

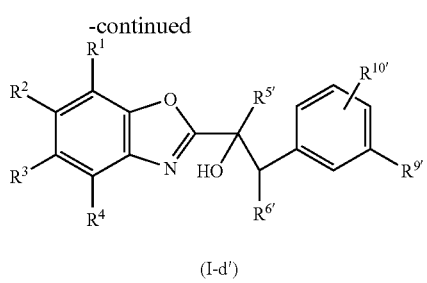

(I-d')

wherein $R^1$ to $R^4$, $R^{5'}$, $R^{6'}$, $R^{7'}$, $R^{9'}$, $R^{10'}$ and X have the same meanings as defined above.

The compound (IV) can be easily produced by reacting 2-aminophenol which is produced by the method as disclosed in Japanese Provisional Patent Publication No. 45735/1998, Heterocycle, vol. 41, pp. 477-485 (1995), Synthetic Communication, vol. 19, pp. 2921-2924 (1989), Journal of Medicinal Chemistry, vol. 30, pp. 400-405 (1987), Journal of Medicinal Chemistry, pp. 1480-1498 (1956) and the like, with 2-halocarboxylic acids.

The compound (XXI) can be obtained as a commercially available product, or can be obtained by halogenating a substituted alkylbenzene or a substituted benzyl alcohol.

Synthetic Procedure of the Compound (I-c) from a Compound (I-d')

As shown below, the compound (I-c) can be produced by directly subjecting a compound (I-d') to dehydration reaction by using an acid or a base catalyst.

Or else, the compound (I-c) can be produced, after obtaining a compound (I-d") in which the hydroxyl group of the compound (I-d') is converted to a suitable eliminatable group, by subjecting to elimination reaction of the group.

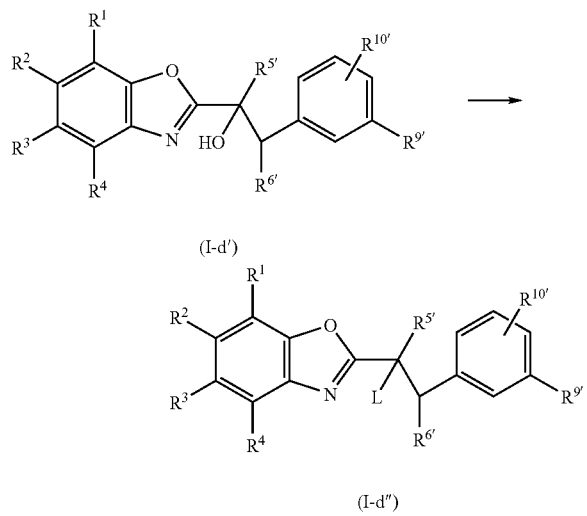

wherein $R^1$ to $R^4$, $R^{5'}$, $R^{6'}$, $R^{9'}$ and $R^{10'}$ have the same meanings as defined above, and L represents a halogen atom, an alkylsulfonyloxy group, an alkylcarbonyloxy group, a phenylcarbonyloxy group, an alkylcarbonyloxy group, a phenylcarbonyloxy group or alkoxy group.

As the solvent to be used for the synthesis of the compound (I-d"), it is not specifically limited so long as it does not pertain the present reaction, for example, ethers such as diethyl ether, tetrahydrofuran, dioxane, etc.; dipolar aprotic solvents such as N,N-dimethylformamide, dimethylsulfoxide, etc.; aromatic hydrocarbons such as benzene, toluene, xylene, etc.; nitriles such as acetonitrile, etc.; ketones such as acetone, methyl ethyl ketone, etc.; and a mixed solvent of the above solvents, etc.

As a kind of the eliminatable group, there may be mentioned, for example, a halogen atom such as a chlorine atom, a bromine atom, a fluorine atom, an iodine atom and the like; a sulfonyloxy group such as a methanesulfonyloxy group, a p-toluenesulfonyloxy group, trifluoromethanesulfonyloxy group and the like, a carbonyloxy group such as a trifluoroacetyloxy group, an acetyloxy group, a p-nitrobenzoyloxy group and the like; an alkoxy group such as a methoxy group, an ethoxy group and the like.

As a kind of the base, there may be mentioned, for example, organic bases such as triethylamine, pyridine, 4-N,N-dimethylaminopyridine, N,N-dimethylaniline, 1,4-diazabicyclo[2.2.2]octane, 1,8-diazabicyclo[5.4.0]undeca-7-ene, etc.; alkali metal alkoxides; alkoxides such as sodium methoxide, sodium ethoxide, potassium-t-butoxide, etc.; inorganic bases such as sodium hydride, potassium hydride, sodium amide, sodium hydroxide, potassium hydroxide, potassium carbonate, sodium carbonate, potassium hydrogen carbonate, sodium hydrogen carbonate, etc.; lithium diisopropylamide, bistrimethylsilyl lithium amide.

As a kind of the acid catalyst, there may be mentioned, for example, mineral acids such as hydrochloric acid, sulfuric acid, nitric acid, etc.; organic acids such as formic acid, acetic acid, propionic acid, methanesulfonic acid, benzenesulfonic acid, p-toluenesulfonic acid, etc.; acid addition salts of amines such as pyridine hydrochloride, triethylamine hydrochloride, etc.; metal halides such as titanium tetrachloride, zinc chloride, ferrous chloride, ferric chloride, etc.; Lewis acids such as boron trifluoride.etherate, etc.

An amount of the acid catalyst to be used is 0.001 to 1 mole per mole of the compound (I-d').

In the production of the compound (I-c), it is carried out with a reaction concentration of 5 to 80%.

In the production method, a ratio of the base to be used may be 0.5 to 2 moles per mole of the compound (I-d'), preferably 1 to 1.2 mole.

The reaction temperature is not specifically limited so long as it is carried out at a boiling point of the solvent to be used or lower, and usually carried out at 0 to 110° C.

The reaction time may vary depending on the above-mentioned density and temperature, and it is usually carried out for 0.5 to 24 hours.

(Synthetic Method 2-3)

The compound (I-c') (in the formula (I-c), a compound wherein $R^{6'}$ is $R^{6''}$ ($R^{6''}$ represents a hydrogen atom or an alkyl group having 1 to 4 carbon atoms)) can be synthesized, as shown below, by reacting a compound (IV) with triphenylphosphine in a solvent to prepare a phosphonium salt, and reacting it with a compound (XVII') in the presence of a base.

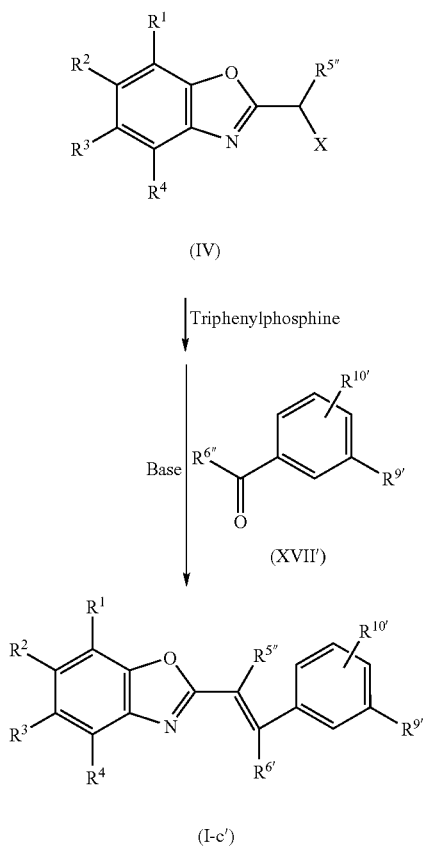

wherein $R^{6''}$ represents a hydrogen atom or an alkyl group having 1 to 4 carbon atoms, $R^1$ to $R^4$, $R^{5'}$, $R^{9'}$, $R^{10'}$ and X have the same meanings as defined above.

The compound (IV) can be obtained by the method as mentioned above.

As the solvent, it is not specifically limited so long as it does not pertain the present reaction, and there may be mentioned, for example, ethers such as diethyl ether, tetrahydrofuran, dioxane, etc.; dipolar aprotic solvents such as N,N-dimethylformamide, dimethylsulfoxide, etc.; aromatic hydrocarbons such as benzene, toluene, xylene, etc.; nitriles such as acetonitrile, etc.; ketones such as acetone, methyl ethyl ketone, etc.; and a mixed solvent of the above solvents, etc.

Triphenylphosphine can be obtained as a commercially available product.

As a kind of the base, there may be mentioned, for example, triethylamine, organic bases such as pyridine, 4-N,N-dimethylaminopyridine, N,N-dimethylaniline, 1,4-diazabicyclo-[2.2.2]octane, 1,8-diazabicyclo[5.4.0]undeca-7-ene, etc.; alkali metal alkoxides; alkoxides such as sodium methoxide, sodium ethoxide, potassium-t-butoxide, etc.; inorganic bases such as sodium hydride, potassium hydride, sodium amide, sodium hydroxide, potassium hydroxide, potassium carbonate, sodium carbonate, potassium hydrogen carbonate, sodium hydrogen carbonate, etc.; lithium diisopropylamide, and bistrimethylsilyl lithium amide.

The compound (XVII') can be obtained as a commercially available product or can be obtained by oxidizing a substituted benzyl alcohol.

In the production of the compound (I-c'), it is carried out with a reaction concentration of 5 to 80%.

In the production method, a ratio of the base to be used may be 0.5 to 2 moles per mole of the compound (VI), preferably 1 to 1.2 mole.

The reaction temperature is not specifically limited so long as it is carried out at a boiling point of the solvent to be used or lower, and usually carried out at 0 to 110° C.

The reaction time may vary depending on the above-mentioned density and temperature, and it is usually carried out for 0.5 to 24 hours.

As the compound (I) thus produced, there may be mentioned, for example, the compound (I-c) such as compounds I-c-1 to I-c-183 shown in Table 24 mentioned below, and the compound (I-d) such as compounds I-d-1 to I-d-65 shown in table 25 mentioned below. For example, there may be mentioned a compound I-c-1 means that $R^1$ to $R^4$, $R^{6'}$ and $R^{10'}$ are hydrogen atoms, and $R^{9'}$ is a trifluoromethyl group in the compound (I-c).

(3) In the formula (I), when A is $CHR^5$—Y, $CR^5$=$CR^6$, $CR^5R^7$—$CHR^6$ or $CHR^5$, the compound (I) can be synthesized by either of the method of the Synthetic method 3-1, 3-2 or 3-3 shown below.

(Synthetic Method 3-1)

(a) The compound (I-e) (a compound wherein A is $CHR^5$—Y in the compound (I)) can be produced, as shown below, by reacting, the compound (IV) and the compound (V) in a solvent.

And the reaction is preferably carried out in the presence of a base.

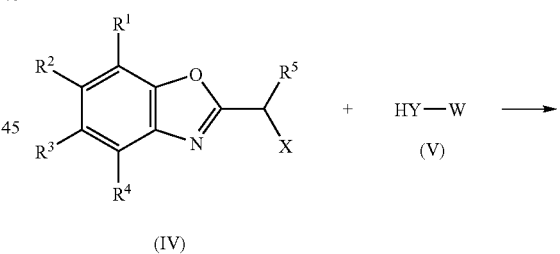

wherein $R^1$ to $R^4$, $R^5$, W and Y have the same meanings as defined above, and X is a halogen atom.

The compound (IV) can be synthesized according to the same manner as mentioned above.

The compound (V) can be obtained as a commercially available product or can be obtained as a product by the methods as described in U.S. Pat. No. 37,800,054, EP 255047, EP 220025, Journal of Medicinal Chemistry, pp. 601-606 (1985) and the like.

As the solvent to be used, it is not specifically limited so long as it does not pertain the present reaction, and there may be mentioned, for example, ethers such as diethyl ether, tetrahydrofuran, dioxane, etc.; Dipolar aprotic solvents such as N,N-dimethylformamide, dimethylsulfoxide, etc.; aromatic hydrocarbons such as benzene, toluene, xylene, etc.; nitriles such as acetonitrile, etc.; ketones such as acetone, methyl ethyl ketone, etc.; and a mixed solvent of the above solvents, etc., As a kind of the base to be used for the production of the compound (I), there may be mentioned, for example, organic bases such as triethylamine, pyridine, 4-N,N-dimethylaminopyridine, N,N-dimethylaniline, 1,4-diazabicyclo[2.2.2]octane, 1,8-diazabicyclo[5.4.0]undeca-7-ene, etc., alkali metal alkoxides, alkoxides such as sodium methoxide, sodium ethoxide, potassium-t-butoxide, etc., inorganic bases such as sodium hydride, potassium hydride, sodium amide, sodium hydroxide, potassium hydroxide, potassium carbonate, sodium carbonate, potassium hydrogen carbonate, sodium hydrogencarbonate, etc., lithium diisopropylamide, and bistrimethylsilyl lithium amide.

An amount of the base to be used is 0.5 to 2 moles per mole of the compound (IV).

(b) The compound (I-e) can be produced, as shown below, by reacting the compound (VI) and the compound (VII) in a solvent.

And the reaction is preferably carried out in the presence of a base.

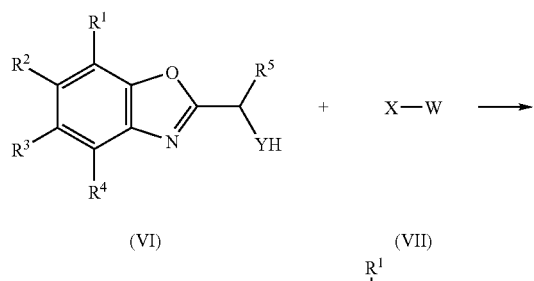

(VI)          (VII)

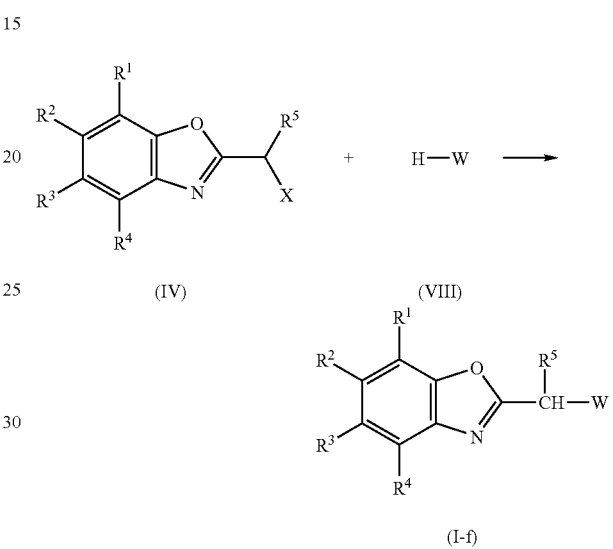

(I-e)

wherein $R^1$ to $R^4$, $R^5$, X, Y and W have the same meanings as defined above.

The compound (VI) can be produced by esterifying the compound (IV), and then, hydrolyzing the resulting compound, or reacting the compound (IV) with sodium hydrosulfide or aqueous ammonia.

The compound (VII) can be obtained as a commercially available product or obtained by halogenating the compound (V) with a halogenating agent such as phosphorus oxychloride, etc.

As the solvent and the base, those mentioned in (a) of Synthetic method 3-1 of the compound (I-e) as mentioned above may be mentioned.

An amount of the base to be used is 0.5 to 2 moles per mole of the compound (VI).

(Synthetic Method 3-2)

(a) The compound (I-f) (a compound wherein A is $CHR^5$ in the compound (I)) can be produced, as shown below, by reacting the compound (IV) and the compound (VIII) in a solvent.

And the reaction is preferably carried out in the presence of a base.

(IV)          (VIII)

(I-f)

wherein $R^1$ to $R^4$, $R^5$, X and W have the same meanings as defined above.

As the solvent and the base, those mentioned in (1) of synthetic method 1 of the compound (I-e) as mentioned above may be mentioned.

In the production of the compound (I-f), it is carried out with a reaction concentration of 5 to 80%.

In the production method, a ratio of the base to be used may be 0.5 to 2 moles per mole of the compound (IV), preferably 1 to 1.2 mole.

The reaction temperature is not specifically limited so long as it is carried out at a boiling point of the solvent to be used or lower, and usually carried out at 0 to 110° C.

The reaction time may vary depending on the above-mentioned density and temperature, and it is usually carried out for 0.5 to 24 hours.

As the compound (I) thus synthesized, there may be mentioned, for example, compounds (I-e-1) to (I-e-81) shown in Table 28, and compounds (I-f-1), (I-f-12) shown in Table 29, and the like.

For example, the compound (I-e-20) means that $R^1$, $R^2$ and $R^4$ in the compound (I-e) are hydrogen atoms, $R^3$ is a chlorine atom, $R^5$ is an ethyl group, Y is an oxygen atom, and W is a 1,2,3-thiadiazole group shown by (W-5-1).

(b) The compound (I-g) (a compound where A is $CR^5 = CR^6$ in the compound (I)) can be also produced, as shown below, by reacting the compound (XII) and the compound (XI) in a solvent.

And the reaction can be carried out by using a base or, an acid catalyst, if necessary.

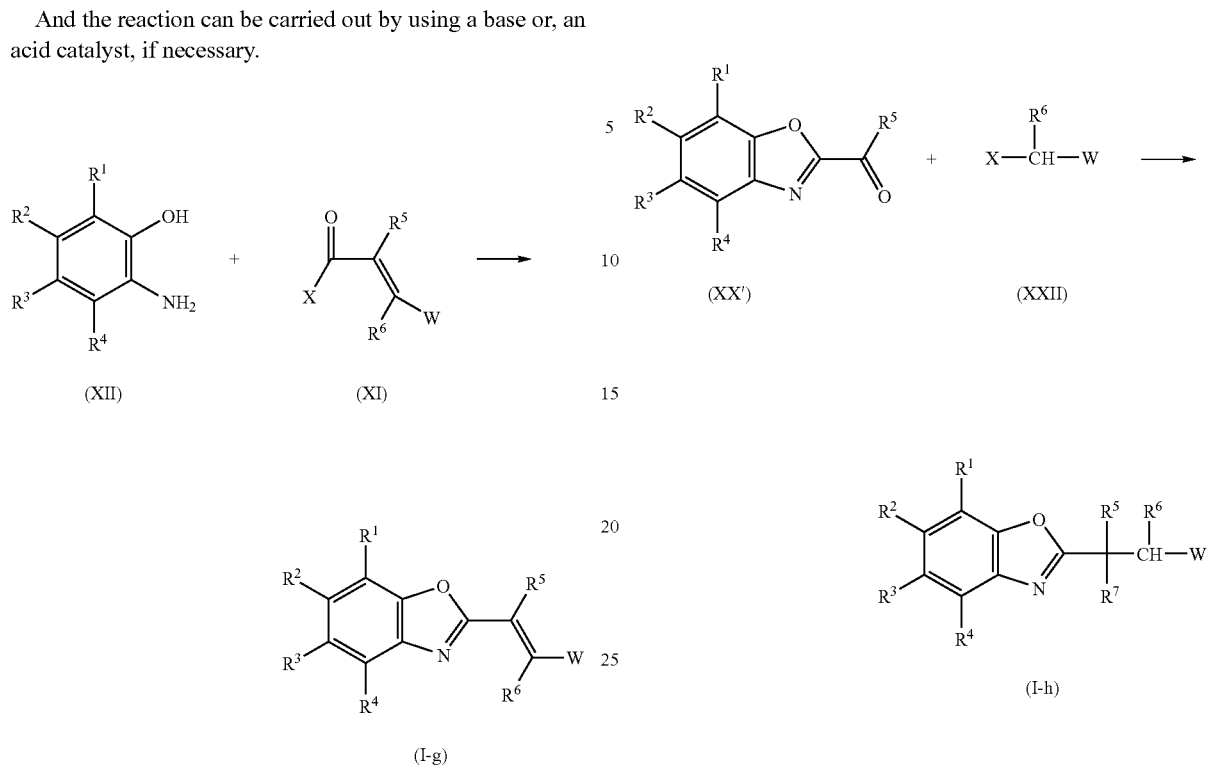

wherein $R^1$ to $R^4$, $R^5$, $R^6$, X and W have the same meanings as defined above.

The compound (XI) can be obtained as a commercially available product or produced by the method as described in Journal of Medicinal Chemistry, pp. 1147-1156 (1989), DE2558117, EP 419410 and the like.

As the solvent and the base, those mentioned in (1) of Synthetic method 1 of the compound (I-e) as mentioned above may be mentioned.

As a kind of the acid catalyst, there may be mentioned, for example, mineral acids such as hydrochloric acid, sulfuric acid, nitric acid, etc., organic acids such as formic acid, acetic acid, propionic acid, methanesulfonic acid, benzenesulfonic acid, p-toluenesulfonic acid, etc., acid addition salts of amines such as pyridine hydrochloride, triethylamine hydrochloride, etc.; metal halides such as titanium tetrachloride, zinc chloride, ferrous chloride, ferric chloride, etc.;. Lewis acids such as boron trifluoride.etherate, etc.

An amount of the base catalyst or the acid catalyst to be used is 0.001 to 1 mole per mole of the compound (XII).

(Synthetic Method 3-3)

The compound (I-h) (a compound wherein A is $CR^5R^7$—$CHR^6$ in the compound (I)), when $R^7$ is, for example, a hydroxyl group, as shown below, it can be produced by reacting the compound (XX') and the compound (XXII) in a solvent.

And the reaction is preferably carried out in the presence of a catalyst.

wherein $R^1$ to $R^4$, $R^5$ to $R^7$, X and W have the same meanings as defined above.

The compound (XX') can be obtained by oxidating the compound (VI) as shown in Reference example 3 as mentioned below.

The compound (XXII) can be obtained as a commercially available product, or can be produced by haloalkylation or halogenation as described in DE 2123705, EP 241053, WO 9323402 and the like.

As the solvent and the base, those mentioned in (a) of Synthetic method 3-1 of the compound (I-e) as mentioned above may be mentioned.

As the catalyst, there may be mentioned, for example, organometals such as magnesium, zinc, aluminum, lithium, titanium and the like.

The herbicide of the present invention has remarkable herbidical effects and contains at least one of the compound (I) as an effective ingredient.

The compound (I) of the present invention is effective for, for example, monocotyledonus weeds and dicotyledonus weeds, and can be used as a herbicide for paddy fields and upland fields.

As the monocotyledonus weeds, there may be mentioned paddy field weeds such as barnyard grass (*Eschinochloa crusgalli*), bulrush (*Scrips juncoides*), flat sedge (*Cyperus serotinus* Rottb.), smallflower umbrellaplant (*Cyperus difformis*), narrowleaf water plantain (*Alisma canaliculatum*), Monochoria (*Monochoria vaginalis*), arrowhead (*Sagittaria pygmaea*), etc.; and upland fieldweeds such as crabgrass (*Digitaria adscendens*) goosegrass (*Eleusine indica*), green foxtail (*Setaria viridis*) blackgrass (*Alopecurus aequalis*), annual bluegrass (*Poa annua*) etc.

As the dicotyledonus weeds, there may be mentioned paddy field weeds such as False pimpernel (*Lindernia pyxidaria*), Toothcup (*Rotala indica*), Dropwort (*Oenanthe javanica*), etc.; and upland field weeds such as common lambsquarters (*Chenopodium album*), livid amaranth (*Amaranthus lividus*), velvetcaf (*Abutilon theophrasti*), morning glory (*Ipomoea spps.*), common cocklebur (*Xanthium pensylvanicum*), *Cassia obtusifolia*, Chickweed (*Stellaria media*), etc.

The active compound of the present invention can be applied either before germination or after germination of plants, and may be mixed with soil before seeding.

An amount of the active compound of the present invention to be applied can be changed with a wide range depending on a kind of the compound, a kind of plants to be applied, a time to be applied, a place to be applied, qualities of effects to be desired, and the like, and as a general standard, it can be exemplified by a range of about 0.001 to 10 kg, preferably about 0.01 to 1 kg per hectare (ha) of the active compound.

The compound (I) can be used alone, but usually used by formulating a diluent, a surfactant, a dispersant, an auxiliary, etc., according to the conventional manner, and for example, it is preferably prepared as a composition such as a dust, an emulsion, fine granule, granule, wettable powder, granular wettable powder, an aqueous suspension, an oily suspension, an emulsified dispersion, a soluble preparation, an oily agent, a microcapsule, etc.

As a solid diluent, there may be mentioned, for example, talc, bentonite, montmorillonite, clay, kaolin, calcium carbonate, diatomaceous earth, white carbon, vermiculite, slaked lime, siliceous sand, ammonium sulfate, urea, etc.

As a liquid diluent, there may be mentioned, for example, hydrocarbons (for example, kerosene, mineral oil, etc.); aromatic hydrocarbons (for example, benzene, toluene, xylene, dimethylnaphthalene, phenylxylylethane, etc.); halogenated hydrocarbons (for example, chloroform, carbon tetrachloride, etc.); ethers (for example, dioxane, tetrahydrofuran, etc.); ketones (for example, acetone, cyclohexanone, isophorone, etc.); esters (for example, ethyl acetate, ethylene glycol acetate, dibutylmaleate, etc.); alcohols (for example, methanol, n-hexanole, ethylene glycol, etc.); polar solvents (for example, dimethylformamide, dimethylsulfoxide, N-methylpyrrolidone, etc.); and water.

As a sticking agent and a dispersant, there may be mentioned, for example, casein, polyvinyl alcohol, carboxymethyl cellulose, bentonite, xanthene gum, gum arabic, etc.

As an aerosol propellant, there may be mentioned, for example, air, nitrogen, carbon dioxide gas, propane, halogenated hydrocarbons, etc.

As a stabilizer, there may be mentioned, for example, PAP, BHT, etc.

As a surfactant, there may be mentioned, for example, an alkylsulfate, an alkylsulfonate, an alkylbenzenesulfonate, a ligninesulfonate, a dialkylsulfosuccinate, a naphthalenesulfonate condensate, a polyoxyethylene alkyl ether, a polyoxyethylenealkyl allyl ether, apolyoxyethylenealkyl ester, an alkyl sorbitan ester, a polyoxyethylene sorbitan ester, a polyoxyethylene alkylamine, etc.

As the surfactant, there may be mentioned, for example, an alkylsulfate, an alkylsulfonate, an alkylbenzenesulfonate, a ligninesulfonate, a dialkylsulfosuccinate, a naphthalenesulfonate condensate, a polyoxyethylene alkyl ether, a polyoxyethylene alkyl allyl ether, a polyoxyethylene alkyl ester, an alkyl sorbitan ester, a polyoxyethylene sorbitan ester, a polyoxyethylene alkylamine, etc.

In the preparation of the present preparation, the above-mentioned diluent, surfactant, dispersant and auxiliary may be used each singly or in a suitable combination of two or more depending on the respective purposes.

A concentration of an effective ingredient when the compound (I) of the present invention is made into preparations is generally 1 to 50% by weight in an emulsion, generally 0.3 to 25% by weight in a dust, generally 1 to 90% by weight in a wettable powder or a granular wettable powder, generally 0.5 to 10% by weight in a granule, generally 0.5 to 40% by weight in a dispersion, generally 1 to 30% by weight in an emulsified dispersion, generally 0.5 to 20% by weight in a soluble preparation, and generally 0.1 to 5% by weight in an aerosol.

These preparations can be provided for various uses by diluting them to have a suitable concentration and spraying them to stems and/or leaves of plants, soil and paddy field surface, or by applying them directly thereto, depending on the respective purposes.

EXAMPLE

In the following, the present invention will be explained in more detail by referring to Examples and Reference examples. Incidentally, these Examples are not intended to limit the scope of the present invention.

Example 1-1

Synthesis of Compound (I) wherein A is a Single Bond ($R^1$=$R^4$=H) in the Formula (I)

(1) Synthesis of 6-(5-chlorobenzoxazol-2-yl)-2-(3-trifluoromethylphenoxy)pyridine (Compound I-a-3)

First step: Synthesis of: 2-chloro-6-(5-chlorobenzoxazol-2-yl)pyridine

In 60 ml of xylene were dissolved 2.0 g (11.4 mmol) of 6-chloropicolinic chloride, 1.6 g (11.4 mmol) of 2-amino-4-chlorophenol and 0.1 g of p-toluenesulfonate monohydrate, and the resulting mixture was refluxed for 8 hours.

After cooling to room temperature, a residue obtained by removing xylene under reduced pressure was isolated by column chromatography (Wakogel C-300 available from Wako Junyaku, eluted by toluene), to obtain 0.38 g (an yield was 13%) of the desired compound.

Second step: Synthesis of 6-(5-chlorobenzoxazol-2-yl)-2-(3-trifluoromethylphenoxy)pyridine.

In 30 ml of N,N-dimethylformamide were dissolved 0.3 g (1.43 mmol) of 2-chloro-6-(5-chloro-benzoxazol-2-yl)pyridine, 0.28 g (1.72 mmol) of 3-trifluoromethylphenol and 0.3 g (2.15 mmol) of potassium carbonate, and the mixture was refluxed for 8 hours.

After cooling the reaction mixture to room temperature, toluene was added and it was washed with 2N aqueous sodium hydroxide solution, the organic layer was dried over sodium sulfate, and the residue obtained by removing toluene under reduced pressure was applied to column chromatography (Wakogel C-300 available from Wako Junyaku Co., Ltd., eluted by n-hexane:ethyl acetate=10:1) to obtain 0.10 g (an yield was 18%) of the desired compound (I-a-3).

(2) Synthesis of 6-(6-fluorobenzoxazol-2-yl)-2-(3-trifluoromethylphenoxy)pyridine (Compound I-a-6)

First Step: Synthesis of 6-chloropicolinic chloride.

To 20 g (144 mmol) of 6-hydroxypicolinic acid were added 50.6 g (330 mmol) of phosphorus oxychloride and 99.8 g (479 mmol) of phosphorus pentachloride, and the mixture was stirred at 90° C. for 8 hours.

After cooling, 8.6 g of formic acid was added to the mixture, and the resulting mixture was concentrated by an evaporator to obtain the desired compound 6-chloropicolinic chloride quantitatively.

Second step: Synthesis of N-(2,4-difluorophenyl)-6-chloropicolinic anilide

To 100 ml of toluene were added 5.8 g (45 mmol) of 2,4-difluoroaniline and 5.5 g (54 mmol) of triethylamine, then, 20 ml of a toluene solution containing 7.9 g (45 mmol) of 6-chloropicolinic chloride was gradually added to the mixture, and the resulting mixture was stirred under room temperature for 5 hours.

Toluene was added to the resulting mixture, the organic layer was washed with water and a saturated saline solution, and dried over anhydrous sodium sulfate.

After concentration by an evaporator, the resulting crystalline was washed with hexane to obtain 6.56 g (an yield was 54%) of the desired compound.

Third step: Synthesis of 6-(6-fluorobenzoxazol-2'-yl)-2-(3-trifluoromethylphenoxy)pyridine.

To 50 ml of N,N-dimethylformamide were added 1.8 g (11.2 mmol) of 3-trifluoromethylphenol, 2.0 g (7.4 mmol) of N-(2,4-difluorophenyl)-6-chloropicolinic anilide and 4.1 g (29.6 mmol) of potassium carbonate, and the mixture was refluxed for 12 hours.

After cooling to room temperature, toluene was added to the mixture, the organic layer was washed with water and a saturated saline solution, and dried over anhydrous sodium sulfate.

After concentrating the extract by an evaporator, the resulting residue was applied to column chromatography (Wakogel C-300 available from Wako Junyaku Co., Ltd., an elute was toluene) to obtain 0.85 g (an yield was 31%) the compound 6 which is a desired compound.

(3) Synthesis of 2-(1-methyl-3-trifluoromethylpyrazol-5-yloxy)-6-(5-chlorobenzoxazo-2yl)pyridine (Compound (W-3-1) of the compound (W-3))

To an N,N-dimethylformamide solution containing 0.10 g of 60% sodium hydride was added 0.34 g (2.04 mmol) of 1-methyl-5-hydroxy-3-trifluoromethylpyrazol, and the mixture was stirred at room temperature for 15 minutes.

To the mixture was added 0.36 g (1.36 mmol) of 2-chloro-6-(5-chlorobenzoxazo-2-yl pyridine, and the resulting mixture was stirred at 110° C. for 24 hours.

After cooling the reaction mixture to room temperature, toluene was added and it was washed with 2N aqueous sodium hydroxide solution, the organic layer was dried over sodium sulfate, and the residue obtained by removing toluene under reduced pressure was applied to column chromatography (Wakogel C-300 available from Wako Junyaku Co., Ltd., eluted by n-hexane:ethyl acetate=10:1) to obtain 0.06 g (an yield was 11%) of the desired compound.

(4) Synthesis of the Compound (I) in Tables 1 to 24

According to the methods mentioned in the above (1) to (3), other compounds (I) shown in Tables 1 to 24 were synthesized.

Among the compounds (I) synthesized as mentioned above, the compound (I-a') (in the formula (I-a), a compound wherein Y" is Y') is shown in Table 1, the compounds (I-b) are shown in Tables 2 to 21 as compounds (W-1) to (W-35), and intermediates are shown in Tables 22 and 23 with their physical properties.

TABLE 1

(I-a')

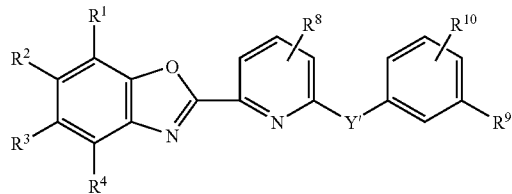

| Compound | R$^1$ | R$^2$ | R$^3$ | R$^4$ | R$^8$ | R$^9$ | R$^{10}$ | Y' | Physical property |
|---|---|---|---|---|---|---|---|---|---|
| I-a-1 | H | H | H | H | H | CF$_3$ | H | O | m.p. 99-101° C. |
| I-a-2 | H | H | F | H | H | CF$_3$ | H | O | m.p. 130-132° C. |
| I-a-3 | H | H | Cl | H | H | CF$_3$ | H | O | m.p. 127-129° C. |
| I-a-4 | H | H | OCH$_3$ | H | H | CF$_3$ | H | O | m.p. 109-111° C. |
| I-a-5 | H | H | NO$_2$ | H | H | CF$_3$ | H | O | |
| I-a-6 | H | F | H | H | H | CF$_3$ | H | O | m.p. 118-119° C. |

TABLE 1-continued (I-a')

| Compound | R¹ | R² | R³ | R⁴ | R⁸ | R⁹ | R¹⁰ | Y' | Physical property |
|---|---|---|---|---|---|---|---|---|---|
| I-a-7 | H | F | H | H | H | $CF_3$ | 4-F | O | m.p. 142-148° C. |
| I-a-8 | H | H | Cl | H | H | $CF_3$ | H | S | |
| I-a-9 | H | H | Cl | H | H | $CF_3$ | H | S | |
| I-a-10 | H | H | Cl | H | H | $CF_3$ | H | $SO_2$ | |
| I-a-11 | H | H | CN | H | H | $CF_3$ | H | $SO_2$ | |
| I-a-12 | H | H | CN | H | H | $CF_3$ | 4-F | O | |
| I-a-13 | H | H | $CF_3$ | H | H | $CF_3$ | H | O | m.p. 96-98° C. |
| I-a-14 | H | H | $C_2H_5OCO$ | H | H | $CF_3$ | 4-F | O | |
| I-a-15 | H | H | $C_2H_5OCO$ | H | H | $CF_3$ | H | O | |
| I-a-16 | H | H | CN | H | H | $CF_3$ | H | O | |
| I-a-17 | H | H | $CF_3$ | H | H | $CF_3$ | H | O | |
| I-a-18 | H | H | CN | H | H | $CF_3$ | H | O | m.p. 190-192° C. |
| I-a-19 | H | H | $CF_3$ | H | H | $CF_3$ | H | O | |
| I-a-20 | H | F | F | H | H | $CF_3$ | H | O | |
| I-a-21 | H | F | F | H | H | $CF_3$ | 4-F | O | |
| I-a-22 | H | F | F | H | H | $CF_3$ | H | O | |
| I-a-23 | H | F | F | H | H | $CF_3$ | 4-F | O | |
| I-a-24 | H | F | Cl | H | H | $CF_3$ | H | O | |
| I-a-25 | H | F | Cl | H | H | $CF_3$ | 4-F | O | |
| I-a-26 | H | F | Cl | H | H | $CF_3$ | H | O | |
| I-a-27 | H | F | Cl | H | H | $CF_3$ | 4-F | O | |
| I-a-28 | H | F | CN | H | H | $CF_3$ | H | O | |
| I-a-29 | H | F | CN | H | H | $CF_3$ | 4-F | O | |
| I-a-30 | H | F | CN | H | H | $CF_3$ | H | O | |
| I-a-31 | H | F | CN | H | H | $CF_3$ | 4-F | O | |
| I-a-32 | H | H | Cl | H | H | $CH_3SO_2$ | H | O | |
| I-a-33 | H | H | Cl | H | H | $CH_3SO_2$ | H | O | |
| I-a-34 | H | H | Cl | H | H | CN | CN | O | |
| I-a-35 | H | H | Cl | H | H | CN | CN | O | |
| I-a-36 | H | H | Cl | H | H | CN | H | O | |
| I-a-37 | H | H | Cl | H | H | CN | CN | O | |
| I-a-38 | H | H | Cl | H | H | $CH_3SO_2$ | H | O | |
| I-a-39 | H | H | $CF_3$ | H | H | CN | H | O | |
| I-a-40 | H | H | $CF_3$ | H | H | CN | H | O | |
| I-a-41 | H | H | $CF_3$ | H | H | CN | H | O | |
| I-a-42 | H | H | $CF_3$ | H | H | CN | H | O | |
| I-a-43 | H | H | $CF_3$ | H | H | CN | CN | O | |
| I-a-44 | H | H | $CF_3$ | H | H | CN | CN | O | |
| I-a-45 | H | H | $CF_3$ | H | H | CN | CN | O | |
| I-a-46 | H | H | CN | H | H | CN | H | O | |
| I-a-47 | H | H | CN | H | H | CN | H | O | |
| I-a-48 | H | H | CN | H | H | CN | H | O | |
| I-a-49 | H | H | CN | H | H | CN | H | O | |
| I-a-50 | H | H | CN | H | H | $CF_3O$ | H | O | |
| I-a-51 | H | H | CN | H | H | CN | CN | O | |
| I-a-52 | H | H | CN | H | H | CN | CN | O | |
| I-a-53 | H | H | CN | H | H | $CH_3SO_2$ | H | O | |
| I-a-54 | H | H | CN | H | H | $CH_3SO_2$ | H | O | |
| I-a-55 | H | H | CN | H | H | $CH_3SO_2$ | H | O | |
| I-a-56 | H | H | $CF_3$ | H | H | $CH_3SO_2$ | H | O | |
| I-a-57 | H | H | $CF_3$ | H | H | $CH_3SO_2$ | H | O | |
| I-a-58 | H | F | F | H | H | CN | H | O | |
| I-a-59 | H | F | F | H | H | CN | H | O | |
| I-a-60 | H | F | Cl | H | H | CN | H | O | |
| I-a-61 | H | F | Cl | H | H | CN | H | O | |
| I-a-62 | H | F | Cl | H | H | CN | CN | O | |
| I-a-63 | H | F | Cl | H | H | CN | CN | O | |
| I-a-64 | H | F | Cl | H | H | $CH_3SO_2$ | H | O | |
| I-a-65 | H | F | Cl | H | H | $CH_3SO_2$ | H | O | |
| I-a-66 | H | F | CN | H | H | CN | H | O | |
| I-a-67 | H | F | CN | H | H | CN | H | O | |

TABLE 1-continued (I-a')

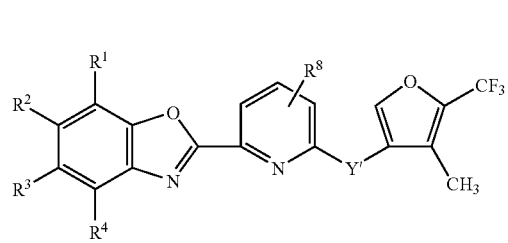

| Compound | R¹ | R² | R³ | R⁴ | R⁸ | R⁹ | R¹⁰ | Y' | Physical property |
|---|---|---|---|---|---|---|---|---|---|
| I-a-68 | H | H | Cl | H | H | H | CF₃ | O | |
| I-a-69 | H | F | CF₃ | H | H | H | CN | O | |
| I-a-70 | H | H | Cl | H | H | CN | H | O | |
| I-a-71 | H | F | F | H | H | CN | CN | O | |
| I-a-72 | H | F | F | H | H | CN | CN | O | |
| I-a-73 | H | F | F | H | H | CH₃SO₂ | H | O | |
| I-a-74 | H | F | F | H | H | CH₃SO₂ | H | O | |
| I-a-75 | H | F | CN | H | H | CN | CN | O | |
| I-a-76 | H | F | CN | H | H | CH₃SO₂ | H | O | |
| I-a-77 | H | H | CN | H | 3-CH₃ | CF₃ | H | O | |
| I-a-78 | H | H | CN | H | 3-OCH₃ | CF₃ | H | O | |
| I-a-79 | H | H | CN | H | 3-Cl | CF₃ | H | O | |
| I-a-80 | H | H | CN | H | 4-CF₃ | CF₃ | H | O | |
| I-a-81 | H | H | CN | H | 3-CH₃ | CF₃ | H | NH | |
| I-a-82 | H | H | CN | H | 3-OCH₃ | CF₃ | H | NCH₃ | |
| I-a-83 | H | H | CN | H | 3-Cl | CF₃ | H | S | |
| I-a-84 | H | H | CN | H | 4-CF₃ | CF₃ | H | SO₂ | |

TABLE 2

(W-29)

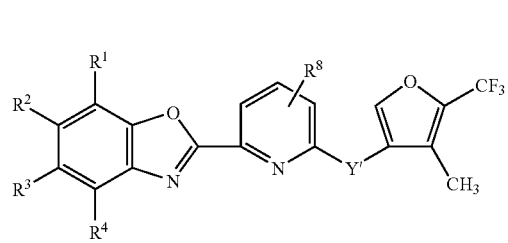

| Compound | R¹ | R² | R³ | R⁴ | R⁸ | Y' | Physical properties |
|---|---|---|---|---|---|---|---|
| W-29-1 | H | H | CF₃ | H | H | SO₂ | m.p. 127-129° C. |

TABLE 3

(W-14)

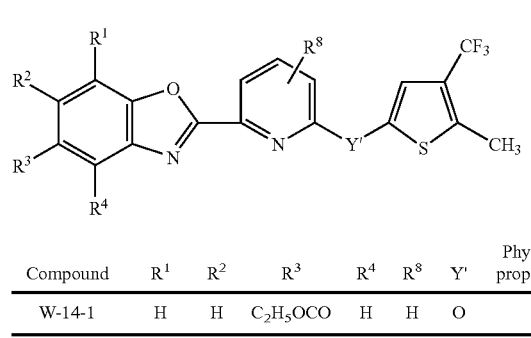

| Compound | R¹ | R² | R³ | R⁴ | R⁸ | Y' | Physical properties |
|---|---|---|---|---|---|---|---|
| W-14-1 | H | H | C₂H₅OCO | H | H | O | |

TABLE 4

(W-1)

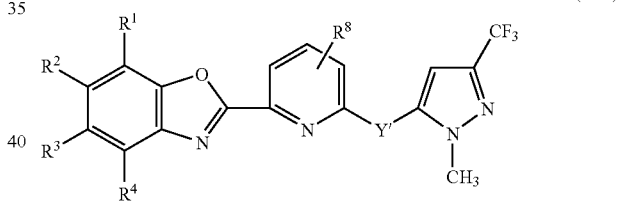

| Compound | R¹ | R² | R³ | R⁴ | R⁸ | Y' | Physical properties |
|---|---|---|---|---|---|---|---|
| W-1-1 | H | H | Cl | H | H | O | |
| W-1-2 | H | H | Cl | H | H | S | |
| W-1-3 | H | H | Cl | H | H | SO₂ | |
| W-1-4 | H | H | Cl | H | H | NH | |
| W-1-5 | H | H | Cl | H | H | N(CH₃) | |
| W-1-6 | H | H | OCH₃ | H | H | O | |
| W-1-7 | H | H | CF₃ | H | H | O | |
| W-1-8 | H | H | C₂H₅OCO | H | H | O | |
| W-1-9 | H | H | F | H | H | O | |
| W-1-10 | H | H | Br | H | H | O | |
| W-1-11 | H | H | NO₂ | H | H | O | |
| W-1-12 | H | H | CN | H | H | O | |
| W-1-13 | H | F | Cl | H | H | O | |
| W-1-14 | H | F | CN | H | H | O | |
| W-1-15 | H | F | F | H | H | O | |
| W-1-16 | H | F | NO₂ | H | H | O | |

TABLE 5

(W-2)

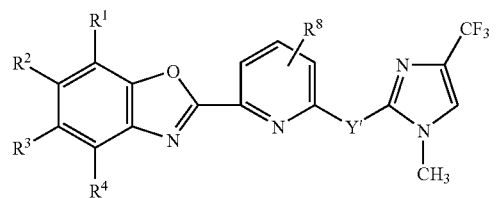

| Compound | R¹ | R² | R³ | R⁴ | R⁸ | Y' | Physical properties |
|---|---|---|---|---|---|---|---|
| W-2-1 | H | H | CF₃ | H | H | S | |

TABLE 6

(W-13)

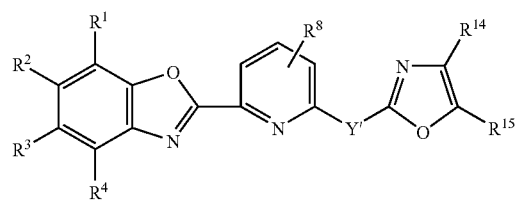

| Compound | R¹ | R² | R³ | R⁴ | R⁸ | R¹⁴ | R¹⁵ | Y' | Physical properties |
|---|---|---|---|---|---|---|---|---|---|
| W-13-1 | H | H | Br | H | H | CF₃ | H | O | |
| W-13-2 | H | H | Br | H | H | H | CF₃ | O | |

TABLE 7

(W-10)

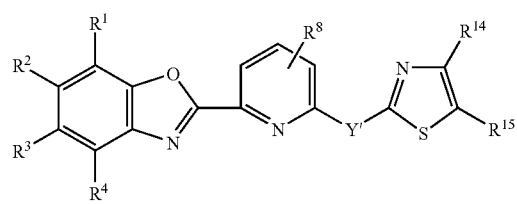

| Compound | R¹ | R² | R³ | R⁴ | R⁸ | R¹⁴ | R¹⁵ | Y' | Physical properties |
|---|---|---|---|---|---|---|---|---|---|
| W-10-1 | H | H | NO₂ | H | H | CF₃ | H | O | |
| W-10-2 | H | H | NO₂ | H | H | H | CF₃ | O | |

TABLE 8

(W-3)

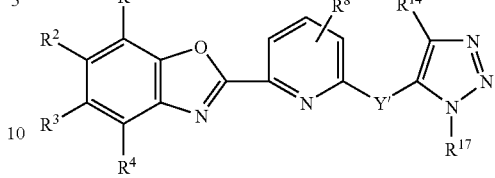

| Compound | R¹ | R² | R³ | R⁴ | R⁸ | R¹⁴ | R¹⁷ | Y' | Physical properties |
|---|---|---|---|---|---|---|---|---|---|
| W-3-1 | H | H | CN | H | H | CH₃ | CF₃ | O | |
| W-3-2 | H | H | CN | H | H | H | CF₃ | O | |

TABLE 9

(W-4)

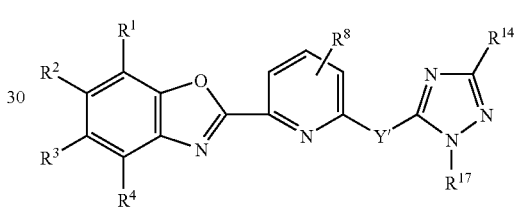

| Compound | R¹ | R² | R³ | R⁴ | R⁸ | R¹⁴ | R¹⁷ | Y' | Physical properties |
|---|---|---|---|---|---|---|---|---|---|
| W-4-1 | H | H | CH₃ | H | H | CH₃ | CF₃ | O | |
| W-4-2 | H | H | CH₃ | H | H | H | CF₃ | O | |

TABLE 10

(W-32)

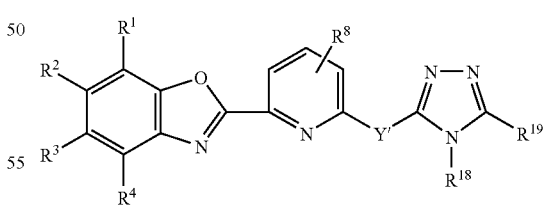

| Compound | R¹ | R² | R³ | R⁴ | R⁸ | R¹⁸ | R¹⁹ | Y' | Physical properties |
|---|---|---|---|---|---|---|---|---|---|
| W-32-1 | H | F | Cl | H | H | CH₃ | CF₃ | O | |
| W-32-2 | H | F | Cl | H | H | H | CF₃ | O | |

TABLE 11

(W-5)

| Compound | R¹ | R² | R³ | R⁴ | R⁸ | R¹⁴ | Y' | Physical properties |
|---|---|---|---|---|---|---|---|---|
| W-5-1 | H | F | CN | H | H | CF₃ | O | |
| W-5-2 | H | F | CN | H | H | H | O | |

TABLE 12

(W-11)

| Compound | R¹ | R² | R³ | R⁴ | R⁸ | R¹⁷ | Y' | Physical properties |
|---|---|---|---|---|---|---|---|---|
| W-11-1 | H | F | CF₃ | H | H | H | O | |
| W-11-2 | H | F | CF₃ | H | H | CH₃ | O | |

TABLE 13

(W-20)

| Compound | R¹ | R² | R³ | R⁴ | R⁸ | R¹⁴ | R¹⁵ | R¹⁶ | Y' | Physical properties |
|---|---|---|---|---|---|---|---|---|---|---|
| W-20-1 | H | F | F | H | H | Cl | CF₃ | H | O | |
| W-20-2 | H | F | F | H | H | CF₃ | Cl | H | O | |
| W-20-3 | H | F | C₂H₅OCO | H | H | CH₃ | CF₃ | H | O | |
| W-20-4 | H | F | C₂H₅OCO | H | H | CF₃ | CH₃ | H | O | |
| W-20-5 | H | F | C₂H₅OCO | H | H | CH₃ | CH₃ | CF₃ | O | |

TABLE 14

(W-22)

| Compound | R¹ | R² | R³ | R⁴ | R⁸ | R¹⁴ | R¹⁵ | R¹⁶ | Y' | Physical properties |
|---|---|---|---|---|---|---|---|---|---|---|
| Z-13-1 | H | F | F | H | H | H | H | CF₃ | O | |
| Z-13-2 | H | F | F | H | H | H | H | Cl | O | |

TABLE 15

(W-18)

| Compound | R¹ | R² | R³ | R⁴ | R⁸ | R¹⁴ | R¹⁵ | R¹⁶ | Y' | Physical properties |
|---|---|---|---|---|---|---|---|---|---|---|
| W-18-1 | H | F | Br | H | H | CF₃ | H | CH₃ | O | |
| W-18-2 | H | F | Br | H | H | CF₃ | H | Cl | O | |

TABLE 16

(W-17)

| Compound | R¹ | R² | R³ | R⁴ | R⁸ | R¹⁴ | R¹⁵ | R¹⁶ | Y' | Physical properties |
|---|---|---|---|---|---|---|---|---|---|---|
| W-17-1 | H | H | Cl | H | H | CF₃ | Cl | H | O | |
| W-17-2 | H | F | NH₂ | H | H | CF₃ | H | CH₃ | O | |
| W-17-3 | H | F | NH₂ | H | H | H | H | CF₃ | O | |

TABLE 17

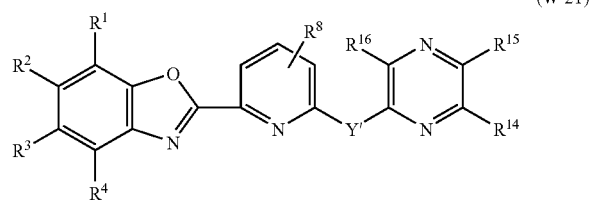

(W-21)

| Compound | R¹ | R² | R³ | R⁴ | R⁸ | R¹⁴ | R¹⁵ | R¹⁶ | Y' | Physical properties |
|---|---|---|---|---|---|---|---|---|---|---|
| W-21-1 | H | F | OCH₃ | H | H | CF₃ | H | H | O | |

TABLE 18

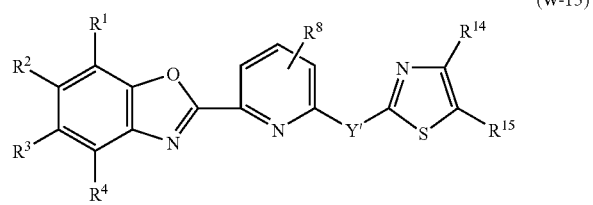

(W-15)

| Compound | R¹ | R² | R³ | R⁴ | R⁸ | R¹⁴ | R¹⁵ | Y' | Physical properties |
|---|---|---|---|---|---|---|---|---|---|
| W-15-1 | H | F | OCH₃ | H | H | H | OCH₃ | O | |
| W-15-2 | H | F | CH₃ | H | H | CF₃ | Cl | O | |

TABLE 19

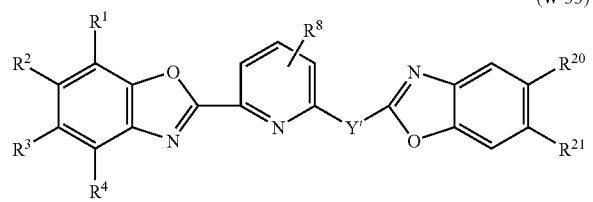

(W-33)

| Compound | R¹ | R² | R³ | R⁴ | R⁸ | R²⁰ | R²¹ | Y' | Physical properties |
|---|---|---|---|---|---|---|---|---|---|
| W-33-1 | H | F | CH₃ | H | H | CN | CH₃ | O | |
| W-33-2 | H | F | CH₃ | H | H | Cl | H | O | |

TABLE 20

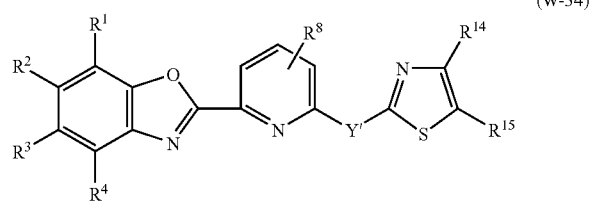

(W-34)

| Compound | R¹ | R² | R³ | R⁴ | R⁸ | R²² | R²³ | Y' | Physical properties |
|---|---|---|---|---|---|---|---|---|---|
| W-34-1 | H | F | CH₃ | H | H | CN | CH₃ | O | |
| W-34-2 | H | F | OCH₃ | H | H | Cl | H | O | |

TABLE 21

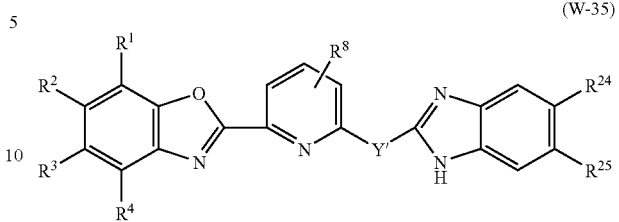

(W-35)

| Compound | R¹ | R² | R³ | R⁴ | R⁸ | R²⁴ | R²⁵ | Y' | Physical properties |
|---|---|---|---|---|---|---|---|---|---|
| W-35-1 | H | H | CH₃ | H | H | CN | CH₃ | O | |
| W-35-2 | H | H | CF₃ | H | H | Cl | H | O | |

TABLE 22

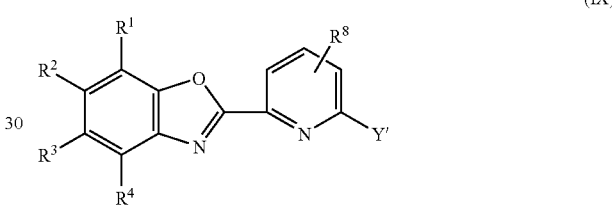

(IX)

| Compound | R¹ | R² | R³ | R⁴ | R⁸ | Y' | Physical properties |
|---|---|---|---|---|---|---|---|
| IX-1 | H | H | Cl | H | H | Cl | m.p. 213–217° C. |
| IX-2 | H | H | OCH₃ | H | H | Cl | m.p. 152–156° C. |
| IX-3 | H | H | H | H | H | Cl | m.p. 188–190° C. |
| IX-4 | H | H | F | H | H | Cl | m.p. 216–219° C. |
| IX-5 | H | H | CF₃ | H | H | Cl | m.p. 161–163° C. |

TABLE 23

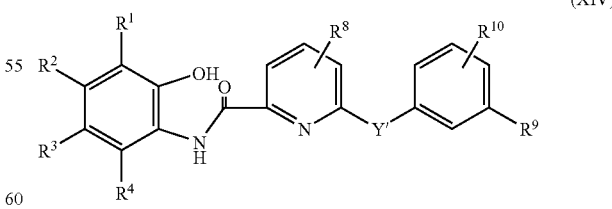

(XIV)

| Compound | R¹ | R² | R³ | R⁴ | R⁸ | R⁹ | R¹⁰ | Y' | Physical properties |
|---|---|---|---|---|---|---|---|---|---|
| XIV-1 | H | H | CN | H | H | H | H | O | m.p. 244–246° C. |

Example 1-2

Synthesis of Compound (I) wherein A is $CR^{5'}=CR^{6'}$ or $CR^{5'}R^{7'}$—$CHR^{6'}$ in the formula (I)

(5) Syntheses of Compound (I-c-54) shown in Table 24 and Compound (I-d-11) shown in Table 25

First step: Synthesis of 1-(5-chlorobenzoxazol-2-yl)-1-acetoxypropane

In 200 ml of DMF was dissolved 40 g (145.7 mmol) of 1-(5-chlorobenzoxazol-2-yl)-1-bromopropane, and to the solution were added 42.9 g (437.2 mmol) of potassium acetate and 30.2 g (218.6 mmol) of potassium carbonate, and the resulting mixture was stirred at 60° C. for 10 hours.

After cooling to room temperature, toluene was added to the reaction mixture and the organic layer was washed with water and a saturated saline solution, and dried over anhydrous sodium sulfate.

The resulting extract was, after concentration by an evaporator, isolated by column chromatography (Wakogel C-300 available from Wako Junyaku Co., Ltd., eluted by n-hexane:ethyl acetate=20:1) to obtain 23.5 g (an yield was 64%) of the desired compound as orange oily product.

Second step: Synthesis of 1-(5-chlorobenzoxazol-2-yl)propanol (Intermediate 301)

In 200 ml of methanol was dissolved 23 g (90.7 mmol) of 1-(5-chlorobenzoxazol-2-yl)-1-acetoxypropane, to the solution was added 20 g (103.7 mmol) of a methanol solution containing 28% sodium methoxide, and the mixture was stirred at 50 to 60° C. for one hour.

After cooling to room temperature, toluene was added to the reaction mixture, and the organic layer was washed with water and a saturated saline solution, and dried over anhydrous sodium sulfate.

The resulting extract was, after concentration by an evaporator, isolated by column chromatography (Wakogel C-300 available from Wako Junyaku Co., Ltd., eluted by n-hexane:ethyl acetate=10:1) to obtain 13.8 g (an yield was 72%) of the desired compound, Intermediate 301, as a pale reddish oily product. $^1$H-NMR (300 MHz), $CDCl_3$, δ (ppm)

7.70 (1H, s), 7.30 to 7.69 (2H, m), 4.91 (1H, q), 2.70 to 3.10 (1H, br), 1.91 to 2.17 (2H, m), 1.05 (3H, t)

Third step: Synthesis of 1-(5-chlorobenzoxazol-2-yl)-1-propanone (Intermediate 302)

In 100 ml of dichloromethane was dissolved 9.6 g (75.6 mmol) of oxalyl chloride, and the solution was stirred at −78° C.

To the solution was gradually added dropwise a mixed solution comprising 26.4 ml of dichloromethane and 7.1 ml of DMSO and the mixture was stirred for 10 minutes.

Further, to the mixture was gradually added 50 ml of a dichloromethane solution containing 8 g (38.7 mmol) of 1-(5-chlorobenzoxazol-2-yl)-1-hydroxypropane, and the resulting mixture was stirred at −78° C. for 15 minutes.

Then, the mixture was stirred at −45° C. for one hour, and 40 ml of triethylamine was gradually added dropwise to the mixture and the resulting mixture was stirred at 0° C. for 20 minutes.

After completion of stirring, 120 ml of a saturated aqueous ammonium chloride solution was added to the mixture, and the organic layer was extracted with ethyl acetate.

The resulting extract was dried over anhydrous sodium sulfate, and after concentration by an evaporator, it was isolated by column chromatography (Wakogel C-300 available from Wako Junyaku Co., Ltd., eluted by n-hexane:ethyl acetate=10:1) to obtain 2.9 g (an yield was 37%) of the desired compound, Intermediate 302, as orange crystal.

Fourth step: Synthesis of 1-(5-chlorobenzoxazol-2-yl)-1-(4-fluoro-3-trifluoromethylbenzyl)propanol (Compound (1-d-11))

Under nitrogen stream, into 50 ml of diethyl ether were added 0.45 g (18.5 mmol) of magnesium and 0.01 g of iodine, and the mixture was stirred for 5 minutes under ice-cooling.

To the mixture was gradually added dropwise 10 ml of a diethyl ether solution containing 3 g (11.7 mmol) of 4-fluoro-3-trifluoromethylbenzyl bromide, and the resulting mixture was thoroughly stirred for 30 minutes.

To the mixture was gradually added dropwise 10 ml of a diethyl ether solution containing 2.46 g (11.7 mmol) of 1-(5-chlorobenzoxazol-2-yl)-1-propanone, and stitted at room temperature for one hour.

To the reaction mixture was added 50 ml of a saturated aqueous ammonium chloride solution, and the organic layer was dried over anhydrous sodium sulfate.

The resulting extract was, after concentration by an evaporator, isolated by column chromatography (Wakogel C-300 available from Wako Junyaku Co., Ltd., eluted by n-hexane:ethyl acetate=20:1) to obtain 2.3 g (an yield was 51%) of a white powder state solid.

Fifth Step: Synthesis of (Compound (I-c-54))

To a dichloromethane (50 ml) solution containing 2.25 g (5.8 mmol) of 1-(5-chlorobenzoxazol-2-yl)-1-(4-fluoro-3-trifluoromethylbenzyl)propanol was added 4.11 g (40.6 mmol) of triethylamine, and further to the mixture was gradually added dropwise 2.0 g (17.4 mmol) of methanesulfonyl chloride dissolved in 20 ml of dichloromethane at 0° C., and the resulting mixture was stitted at room temperature for 30 minutes.

Moreover, to the mixture was added 1.76 g (11.6 mmol) of DBU, and the resulting mixture was refluxed for one hour.

After cooling to room temperature, the organic layer was washed with water and a saturated saline solution, and dried over anhydrous sodium sulfate.

The resulting extract was, after concentration by an evaporator, isolated by column chromatography (Wakogel C-300 available from Wako Junyaku Co., Ltd., eluted by n-hexane:ethyl acetate=10:1), and further recrystallized from hexane to obtain 1.95 g (an yield was 91%) the title compound (E)-2-(5-chlorobenzoxazol-2-yl)-1-(4-fluoro-3-trifluoromethylphenyl)butene (Compound (I-c-54)) as colorless needle crystal.

(6) Synthesis of (E)-2-(5-chlorobenzoxazol-2-yl)-1-(3-trifluoromethylphenyl)butene (Compound (I-c-0.55)).

In toluene, 2.0 g (7.3 mmol) of 1-(5-chlorobenzoxazol-2-yl)-1-bromopropane and 2.1 g (8.0 mmol) of triphenylphosphine were refluxed for 12 hours.

The reaction solution was cooled to −78° C., and to the solution was added dropwise 4.5 ml of 1.6M butyl lithium/hexane solution and the resulting mixture was stirred for 15 minutes.

To the resulting mixture was gradually added dropwise m-trifluoromethylbenzaldehyde, and the resulting mixture was stitted at room temperature for 2 hours.

To the reaction mixture were added water and toluene, the organic layer was dried over ahydrous sodium sulfate, and after concentration by an evaporator, it was separated by column chromatography (Wakogel C-300 available from Wako Junyaku Co., Ltd., eluted by n-hexane:ethyl acetate=12.0:1) to obtain 0.33 g (an yield was 13%) of the desired Compound (I-c-55) as needle crystals.

(7) Synthesis of Compound (I-c-55)

First step: Synthesis of methyl 2-(diethyl phosphonate)butanoate (an intermediate 303)

To 266.2 g (1.60 mol) of triethyl phosphite was added 290 g (1.60 mol) of methyl α-bromobutanoate, and the mixture was refluxed for 2 hours.

After cooling the reaction mixture to room temperature, distillation was carried out by using a vacuum pump to obtain 275.722 g (an yield was 72%) of the desired product, Intermediate 303.

Second step: Synthesis of (E)-2-ethyl-3-(m-trifluoro-methylphenyl)acrylic acid (Intermediate 304)

To 700 ml of tetrahydrofuran were added under ice-cooling, 55.13 g (1.38 mol) of sodium hydride (60% in oil) and 273.63 g (1.15 mol) of methyl 2-(diethyl phosphonate)butanoate, and after stirring for 20 minutes, m-trifluoromethylbenzaldehyde was added to the mixture, and the resulting mixture was stitted at room temperature for 2 hours.

To the reaction solution was added 2N aqueous sodium hydroxide solution, and the resulting mixture was refluxed for 3 hours.

After cooling to room temperature, water and toluene were added to the mixture, and the aqueous layer was collected by separation.

Subsequently, toluene and 2N hydrochloric acid were added to the mixture, and the organic layer was dried over ahydrous sodium sulfate, and after concentration by an evaporator, recrystallization was carried out by using hexane.

As a result, 220 g (an yield was 78%) of the desired product, Intermediate 304, was obtained as colorless needle crystal.

Third step: Synthesis of (E)-2-ethyl-3-(m-trifluoromethylphenyl)acrylic acid chloride To 150 g (0.61 mol) of (E)-2-ethyl-3-(m-trifluoromethylphenyl)acrylic acid was added 109.6 g (0.92 mol) of thionyl chloride, and the resulting mixture was refluxed for 3 hours.

Thionyl chloride was removed by an evaporator to obtain 155 g of (E)-2-ethyl-3-(m-trifluoromethylphenyl)acrylic acid chloride as colorless liquid.

Fourth step: Synthesis of (E)-2-(5-chlorobenzoxazol-2-yl)-1-(3-trifluoromethylphenyl)-1-butene To 700 ml of xylene were added 32.8 g (228 mmol) of 2-amino-4-chlorophenol, 60.0 g (228 mmol) of (E)-2-ethyl-3-(m-trifluoromethylphenyl)acrylic acid chloride, and 13 g of p-toluenesulfonic acid monohydrate, and the resulting mixture was refluxed for 8 hours.

After cooling to room temperature, xylene was removed under reduced pressure and the residue thus obtained was isolated by column chromatography (Wakogel C-300 available from Wako Junyaku Co., Ltd., eluted by n-hexane:ethyl acetate=15:1) to obtain 56 g (an yield was 70%) of the desired product, Compound (I-c-55) as needle crystal.

(8) Synthesis of 2-(5-cyano-6-fluorobenzoxazol-2-yl)-1-(m-trifluoromethylphenyl)-1-butane (Compound (1-d-56))

First step: Synthesis of 2-(m-trifluoromethylbenzyl)butanoic acid

In 20 ml of ethanol was dissolved 1.0 g (4.1 mmol) of (E)-2-ethyl-3-(m-trifluoromethylphenyl)acrylic acid, then, 0.3 g of 5% Pd/C was added to the solution, and the mixture was stirred at room temperature for 3 hours while blowing therein a hydrogen gas.

The reaction mixture was filtered and the filtrate was concentrated to obtain 2-(m-trifluoromethylbenzyl)butanoic acid which is colorless transparent crystal quantitatively.

Second step: Synthesis of 2-(m-trifluoromethylbenzyl)butanoic acid chloride

To 1.0 g (4.1 mmol) of 2-(m-trifluoromethylbenzyl)butanoic acid was added 0.98 g (8.2 mol) of thionyl chloride, and the resulting mixture was refluxed for 3 hours. Thionyl chloride was removed by an evaporator to obtain 1.0 g of 2-(m-trifluoromethylbenzyl)butanoic acid chloride as a colorless liquid.

Third step: Synthesis of Compound (I-d-56)

2-Amino-4-cyano-5-fluorophenol (0.29 g, 1.9 mmol), 0.50 g (1.9 mmol) of 2-(m-trifluoromethylbenzyl)butanoic acid chloride and 0.1 g of p-toluenesulfonic acid monohydrate were added and the mixture was refluxed for 8 hours.

After cooling to room temperature, xylene was removed under reduced pressure and the resulting residue was isolated by column chromatography (Wakogel C-300 available from Wako Junyaku Co., Ltd., eluted by n-hexane:ethyl acetate=15:1) to obtain 0.072 g (an yield was 10%) of the desired Compound I-d-56 as pale yellowish crystal.

(9) Synthesis of 1-(5-chlorobenzoxazol-2-yl)-1-(4-fluoro-3-trifluoromethylbenzyl)propyl fluoride (Compound I-d-13)

In 20 ml of dichloromethane was dissolved 0.53 g (1.6 mmol) of 1-(5-chlorobenzoxazol-2-yl)-1-(4-fluoro-3-trifluoromethylbenzyl)propanol, and 0.32 g (2.0 mmol) of diethylaminosulfur trifluoride was added to the solution and the resulting mixture was stirred at 5° C. for 15 minutes.

After thoroughly stirring by addition of water, the organic layer was washed with water and a saturated saline solution, and dried over anhydrous sodium sulfate.

The resulting extract was, after concentration by an evaporator, isolated by column chromatography (Wakogel C-300 available from Wako Junyaku Co., Ltd., eluted by n-hexane: ethyl acetate=10:1) to obtain 0.47 g (an yield was 88%) of the desired product, Compound I-d-13 as pale yellowish oily product.

(10) Synthesis of Compounds (I) Shown in Tables 24 and 25

According to the methods as described in the above-mentioned (5) to (8), other Compounds (I) shown in Tables 24 and 25 were synthesized.

Among Compounds (I) synthesized as mentioned above, Compound (I-c) is shown in Table 24, Compound (I-d) is shown in Table 25, Intermediate is shown in Table 26, and their physical properties are shown in Table 27.

TABLE 24

(I-c)

| Compound | $R^1$ | $R^2$ | $R^3$ | $R^4$ | $R^{9'}$ | $R^{10'}$ | $R^{5'}$ | $R^{6'}$ |
|---|---|---|---|---|---|---|---|---|
| I-c-1 | H | H | H | H | $CF_3$ | H | H | H |
| I-c-2 | H | H | H | H | $CF_3$ | 4-F | H | H |
| I-c-3 | H | Cl | H | H | $CF_3$ | H | H | $CH_3$ |
| I-c-4 | H | Cl | H | H | $CF_3$ | H | $C_2H_5$ | H |
| I-c-5 | H | Cl | H | H | $CF_3$ | H | $C_3H_7$-n | H |
| I-c-6 | H | Cl | H | H | $CF_3$ | H | $C_3H_7$-i | H |
| I-c-7 | H | Cl | H | H | $CF_3$ | H | $C_4H_9$-n | H |
| I-c-8 | H | Cl | H | H | $CF_3$ | H | $C_4H_9$-i | H |
| I-c-9 | H | Cl | H | H | $CF_3$ | H | $C_4H_9$-s | H |
| I-c-10 | H | Cl | H | H | $CF_3$ | H | $C_4H_9$-t | H |
| I-c-11 | H | F | H | H | $CF_3$ | H | $C_2H_5$ | H |
| I-c-12 | H | F | H | H | $CF_3$ | 4-F | $C_3H_7$-n | H |
| I-c-13 | H | Br | H | H | $CF_3$ | H | $C_2H_5$ | H |
| I-c-14 | H | Br | H | H | $CF_3$ | H | $C_3H_7$-n | H |
| I-c-15 | H | $NO_2$ | H | H | $CF_3$ | H | $C_2H_5$ | H |
| I-c-16 | H | $NO_2$ | H | H | $CF_3$ | 4-F | $C_3H_7$-n | H |
| I-c-17 | H | CN | H | H | $CF_3$ | H | $C_2H_5$ | H |
| I-c-18 | H | CN | H | H | $CF_3$ | H | $C_3H_7$-n | H |
| I-c-19 | H | H | H | $CH_3$ | $CF_3$ | H | $C_2H_5$ | H |
| I-c-20 | H | H | H | $CH_3$ | $CF_3$ | H | $C_3H_7$-n | H |
| I-c-21 | $NH_2$ | H | H | H | $CF_3$ | H | $C_2H_5$ | H |
| I-c-22 | $NH_2$ | H | H | H | $CF_3$ | H | $C_3H_7$-n | H |
| I-c-23 | $CH_3CONH$ | H | H | H | $CF_3$ | H | $C_2H_5$ | H |
| I-c-24 | $CH_3CONH$ | H | H | H | $CF_3$ | H | $C_3H_7$-n | H |
| I-c-25 | Cl | H | $CF_3$ | H | $CF_3$ | H | $C_2H_5$ | H |
| I-c-26 | Cl | H | $CF_3$ | H | $CF_3$ | 4-F | $C_3H_7$-n | H |
| I-c-27 | H | $CF_3$ | H | H | $CF_3$ | H | $C_2H_5$ | H |
| I-c-28 | H | $CF_3$ | H | H | $CF_3$ | H | $C_3H_7$-n | H |
| I-c-29 | H | CN | H | H | $CF_3$ | H | $C_2H_5$ | H |
| I-c-30 | H | CN | H | H | $CF_3$ | 4-F | $C_3H_7$-n | H |
| I-c-31 | H | H | F | H | $CF_3$ | 4-F | H | H |
| I-c-32 | H | H | F | H | $CF_3$ | H | H | H |
| I-c-33 | H | H | F | H | $CF_3$ | 4-F | H | $C_2H_5$ |
| I-c-34 | H | H | F | H | $CF_3$ | H | H | $C_2H_5$ |
| I-c-35 | H | H | F | H | $CF_3$ | 4-F | $CH_3$ | H |
| I-c-36 | H | H | F | H | $CF_3$ | H | $CH_3$ | H |
| I-c-37 | H | H | F | H | $CF_3$ | 4-F | H | $CH_3$ |
| I-c-38 | H | H | F | H | $CF_3$ | H | H | $CH_3$ |
| I-c-39 | H | H | F | H | $CF_3$ | 4-F | CH3 | H |
| I-c-40 | H | H | F | H | $CF_3$ | H | CH3 | H |
| I-c-41 | H | H | F | H | $CF_3$ | 4-F | $C_2H_5$ | H |
| I-c-42 | H | H | F | H | $CF_3$ | H | $C_2H_5$ | H |
| I-c-43 | H | H | F | H | $CF_3$ | 4-F | $C_3H_7$-n | H |
| I-c-44 | H | H | F | H | $CF_3$ | H | $C_3H_7$-n | H |
| I-c-45 | H | H | F | H | $CF_3$ | H | $C_3H_7$-i | H |
| I-c-46 | H | H | F | H | $CF_3$ | H | $C_4H_9$-n | H |
| I-c-47 | H | H | F | H | $CF_3$ | H | $C_4H_9$-i | H |
| I-c-48 | H | H | F | H | $CF_3$ | H | $C_4H_9$-i | H |
| I-c-49 | H | H | F | H | $CF_3$ | H | $C_4H_9$-s | H |
| I-c-50 | H | H | F | H | $CF_3$ | H | $C_4H_9$-t | H |
| I-c-51 | H | H | Cl | H | $CF_3$ | H | H | H |
| I-c-52 | H | H | Cl | H | $CF_3$ | 4-F | $CH_3$ | H |
| I-c-53 | H | H | Cl | H | $CF_3$ | H | $CH_3$ | H |
| I-c-54 | H | H | Cl | H | $CF_3$ | 4-F | $C_2H_5$ | H |
| I-c-55 | H | H | Cl | H | $CF_3$ | H | $C_2H_5$ | H |
| I-c-56 | H | H | Cl | H | $CF_3$ | 4-F | $C_3H_7$-n | H |
| I-c-57 | H | H | Cl | H | $CF_3$ | H | $C_3H_7$-n | H |
| I-c-58 | H | H | Cl | H | $CF_3$ | H | $C_4H_9$-i | H |
| I-c-59 | H | H | Cl | H | $CF_3$ | H | $C_4H_9$-i | H |
| I-c-60 | H | H | Cl | H | $CF_3$ | H | $C_4H_9$-s | H |
| I-c-61 | H | H | Cl | H | $CF_3$ | H | $C_4H_9$-t | H |
| I-c-62 | H | H | Cl | H | $CF_3$ | H | $C_2H_5$ | $CH_3$ |
| I-c-63 | H | H | Cl | H | $CF_3$ | H | $C_3H_7$-n | $CH_3$ |
| I-c-64 | H | H | Cl | H | $CF_3$ | H | $CH_3$ | $C_2H_5$ |
| I-c-65 | H | H | Cl | H | $CF_3$ | H | $C_2H_5$ | $C_2H_5$ |

TABLE 24-continued (I-c)

| Compound | R¹ | R² | R³ | R⁴ | R⁹' | R¹⁰' | R⁵' | R⁶' |
|---|---|---|---|---|---|---|---|---|
| I-c-66 | H | H | Cl | H | CF₃ | H | C₃H₇-n | C₂H₅ |
| I-c-67 | H | H | Br | H | CF₃ | H | C₂H₅ | H |
| I-c-68 | H | H | Br | H | CF₃ | H | C₃H₇-n | H |
| I-c-69 | H | H | I | H | CF₃ | H | C₂H₅ | H |
| I-c-70 | H | H | I | H | CF₃ | H | C₃H₇-n | H |
| I-c-71 | H | H | NO₂ | H | CF₃ | 4-F | C₂H₅ | H |
| I-c-72 | H | H | NO₂ | H | CF₃ | H | C₂H₅ | H |
| I-c-73 | H | H | NO2 | H | CF₃ | 4-F | C₃H₇-n | H |
| I-c-74 | H | H | NO2 | H | CF₃ | H | C3H7-n | H |
| I-c-75 | H | H | CH₃ | H | CF₃ | 4-F | C₂H₅ | H |
| I-c-76 | H | H | CH₃ | H | CF₃ | H | C₂H₅ | H |
| I-c-77 | H | H | CH₃ | H | CF₃ | 4-F | C₃H₇-n | H |
| I-c-78 | H | H | CH₃ | H | CF₃ | H | C₃H₇-n | H |
| I-c-79 | H | H | CN | H | CF₃ | H | CH₃ | H |
| I-c-80 | H | H | CN | H | CF₃ | 4-F | C₂H₅ | H |
| I-c-81 | H | H | CN | H | CF₃ | H | C₂H₅ | H |
| I-c-82 | H | H | CN | H | CF₃ | 4-F | C₃H₇-n | H |
| I-c-83 | H | H | CN | H | CF₃ | H | C₃H₇-n | H |
| I-c-84 | H | H | CN | H | CF₃ | H | C₃H₇-i | H |
| I-c-85 | H | H | CF₃ | H | CF₃ | H | CH₃ | H |
| I-c-86 | H | H | CF₃ | H | CF₃ | H | C₂H₅ | H |
| I-c-87 | H | H | CF₃ | H | CF₃ | 4-F | C₃H₇-n | H |
| I-c-88 | H | H | CF₃ | H | CF₃ | H | C₃H₇-n | H |
| I-c-89 | H | H | CF₃ | H | CF₃ | 4-F | C₂H₅ | CH₃ |
| I-c-90 | H | H | CF₃ | H | CF₃ | H | C₂H₅ | CH₃ |
| I-c-91 | H | H | CF₃ | H | CF₃ | H | C₃H₇-n | CH₃ |
| I-c-92 | H | H | CF₃ | H | CF₃ | H | CH₃ | C₂H₅ |
| I-c-93 | H | H | CF₃ | H | CF₃ | H | C₂H₅ | C₂H₅ |
| I-c-94 | H | H | CF₃ | H | CF₃ | H | C₃H₇-n | C₃H₇-n |
| I-c-95 | H | H | CF₃ | H | CF₃ | H | CH₃ | C₃H₇-n |
| I-c-96 | H | H | CF₃ | H | CF₃ | H | C₂H₅ | C₃H₇-n |
| I-c-97 | H | H | CH₃S | H | CF₃ | H | C₂H₅ | H |
| I-c-98 | H | H | CH₃SO | H | CF₃ | H | C₂H₅ | H |
| I-c-99 | H | H | CH₃SO₂ | H | CF₃ | H | C₂H₅ | H |
| I-c-100 | H | H | C₂H₅SO₂ | H | CF₃ | H | C₂H₅ | H |
| I-c-101 | H | H | CF₃O | H | CF₃ | H | C₃H₇-n | H |
| I-c-102 | H | H | C₂H₅OCO | H | CF₃ | H | C₃H₇-n | H |
| I-c-103 | H | H | COOH | H | CF₃ | H | C₂H₅ | H |
| I-c-104 | H | H | CH₃CONH | H | CF₃ | H | C₂H₅ | H |
| I-c-105 | H | H | CN | H | CF₃ | H | C₂H₅ | CH₃ |
| I-c-106 | H | H | CN | H | CF₃ | H | C₂H₅ | C₂H₅ |
| I-c-107 | H | F | F | H | CF₃ | H | H | H |
| I-c-108 | H | F | F | H | CF₃ | H | CH₃ | CH₃ |
| I-c-109 | H | F | F | H | CF₃ | H | CH₃ | H |
| I-c-110 | H | F | F | H | CF₃ | H | C₂H₅ | CH₃ |
| I-c-111 | H | F | F | H | CF₃ | H | C₂H₅ | H |
| I-c-112 | H | F | F | H | CF₃ | 4-F | C₂H₅ | H |
| I-c-113 | H | F | F | H | CF₃ | H | C₃H₇-n | H |
| I-c-114 | H | F | F | H | CF₃ | 4-F | C₃H₇-n | H |
| I-c-115 | H | F | Cl | H | CF₃ | H | C₂H₅ | H |
| I-c-116 | H | F | Cl | H | CF₃ | H | C₃H₇-n | H |
| I-c-117 | H | Cl | Cl | H | CF₃ | H | C₃H₇-n | H |
| I-c-118 | H | CN | Cl | H | CF₃ | H | C₂H₅ | H |
| I-c-119 | H | CN | Cl | H | CF₃ | H | C₃H₇-n | H |
| I-c-120 | H | CN | F | H | CF₃ | H | C₃H₇-n | H |
| I-c-121 | H | CN | F | H | CF₃ | H | C₃H₇-n | H |
| I-c-122 | H | CN | CN | H | CF₃ | H | C₂H₅ | H |
| I-c-123 | H | CN | CN | H | CF₃ | 4-F | C₂H₅ | H |
| I-c-124 | H | CN | CN | H | CF₃ | H | C₃H₇-n | H |
| I-c-125 | H | F | CF₃ | H | CF₃ | H | C₂H₅ | H |
| I-c-126 | H | F | CF₃ | H | CF₃ | H | C₃H₇-n | H |
| I-c-127 | H | NO₂ | CF₃ | H | CF₃ | H | C₂H₅ | H |
| I-c-128 | H | NO₂ | CF₃ | H | CF₃ | H | C₃H₇-n | H |
| I-c-129 | H | NO₂ | Cl | H | CF₃ | H | C₂H₅ | H |
| I-c-130 | H | NO₂ | Cl | H | CF₃ | H | C₃H₇-n | H |

TABLE 24-continued

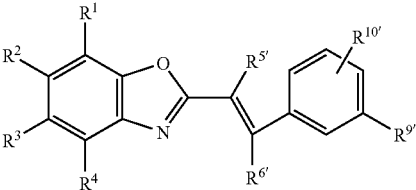

(I-c)

| Compound | R¹ | R² | R³ | R⁴ | R⁹' | R¹⁰' | R⁵' | R⁶' |
|---|---|---|---|---|---|---|---|---|
| I-c-131 | H | CH₃ | Cl | H | CF₃ | H | C₂H₅ | H |
| I-c-132 | H | CH₃ | Cl | H | CF₃ | H | C₃H₇-n | H |
| I-c-133 | H | F | CN | H | CF₃ | H | H | H |
| I-c-134 | H | F | CN | H | CF₃ | 4-F | H | H |
| I-c-135 | H | F | CN | H | CF₃ | H | CH₃ | H |
| I-c-136 | H | F | CN | H | CF₃ | 4-F | CH₃ | H |
| I-c-137 | H | F | CN | H | CF₃ | H | C₂H₅ | H |
| I-c-138 | H | F | CN | H | CF₃ | 4-F | C₂H₅ | H |
| I-c-139 | H | F | CN | H | CF₃ | H | C₃H₇-n | H |
| I-c-140 | H | F | CN | H | CF₃ | 4-F | C₃H₇-n | H |
| I-c-141 | H | Cl | CN | H | CF₃ | H | CH₃ | H |
| I-c-142 | H | Cl | CN | H | CF₃ | 4-F | CH₃ | H |
| I-c-143 | H | Cl | CN | H | CF₃ | H | C₂H₅ | H |
| I-c-144 | H | Cl | CN | H | CF₃ | 4-F | C₂H₅ | H |
| I-c-145 | H | Cl | CN | H | CF₃ | H | C₃H₇-n | H |
| I-c-146 | H | Cl | CN | H | CF₃ | 4-F | C₃H₇-n | H |
| I-c-147 | H | H | F | H | CN | H | CH₃ | H |
| I-c-148 | H | H | F | H | CN | H | C₂H₅ | H |
| I-c-149 | H | H | Cl | H | CN | H | C₃H₇-n | H |
| I-c-150 | H | H | Cl | H | CN | H | C₃H₇-i | H |
| I-c-151 | H | H | Cl | H | H | H | C₂H₅ | H |
| I-c-152 | H | H | Cl | H | H | H | C₃H₇-n | H |
| I-c-153 | H | H | Cl | H | CN | H | CH₃ | H |
| I-c-154 | H | H | Cl | H | CN | H | C₂H₅ | H |
| I-c-155 | H | H | Cl | H | CN | H | C₃H₇-n | H |
| I-c-156 | H | H | Cl | H | CH₃S | H | C₂H₅ | H |
| I-c-157 | H | H | Cl | H | CH₃SO | H | C₂H₅ | H |
| I-c-158 | H | H | Cl | H | CH₃SO₂ | H | C₃H₇-n | H |
| I-c-159 | H | H | Cl | H | NO₂ | H | C₂H₅ | H |
| I-c-160 | H | H | Cl | H | CN | 4-CN | C₂H₅ | H |
| I-c-161 | H | H | CF₃ | H | CN | H | C₂H₅ | H |
| I-c-162 | H | H | CF₃ | H | CN | 4-CN | C₃H₇-n | H |
| I-c-163 | H | H | CN | H | CN | H | C₂H₅ | H |
| I-c-164 | H | H | CN | H | CN | H | C₃H₇-n | H |
| I-c-165 | H | H | CN | H | CF₃O | H | C₂H₅ | H |
| I-c-166 | H | H | CN | H | CN | 4-CN | C₂H₅ | H |
| I-c-167 | H | F | F | H | CN | H | C₃H₇-n | H |
| I-c-168 | H | F | Cl | H | CN | H | C₂H₅ | H |
| I-c-169 | H | F | Cl | H | CN | 4-CN | C₂H₅ | H |
| I-c-170 | H | H | Cl | H | H | 4-CF₃ | C₂H₅ | H |
| I-c-171 | H | H | NO₂ | H | H | H | C₂H₅ | H |
| I-c-172 | H | H | Cl | H | CF₃ | 4-Cl | C₂H₅ | H |
| I-c-173 | H | H | Cl | H | CF₃ | 4-Cl | C₃H₇-n | H |
| I-c-174 | H | H | F | H | CF₃ | 4-Cl | C₂H₅ | H |
| I-c-175 | H | H | CF₃O | H | CF₃ | 4-Cl | C₂H₅ | H |
| I-c-176 | H | H | CF₃O | H | CF₃ | 4-Cl | C₃H₇-n | H |
| I-c-177 | H | H | Cl | H | CF₃O | H | C₂H₅ | H |
| I-c-178 | H | H | NO₂ | H | CF₃O | H | C₃H₇-n | H |
| I-c-179 | H | H | CF₃ | H | H | 4-Cl | C₂H₅ | H |
| I-c-180 | H | H | Cl | H | CN | H | C₂H₅ | H |
| I-c-181 | H | F | F | H | CN | 4-CN | C₂H₅ | H |
| I-c-182 | H | F | CN | H | CN | 4-CN | C₂H₅ | H |
| I-c-183 | H | H | F | H | CN | H | C₂H₅ | H |

TABLE 25

(I-d)

[Structure: benzoxazole with R1, R2, R3, R4 on benzene ring; 2-position connected to C(R5')(R7')-C(R6')H-phenyl(R9',R10')]

| Compound | R1 | R2 | R3 | R4 | R9' | R10' | R5' | R6' | R7' |
|---|---|---|---|---|---|---|---|---|---|
| I-d-1 | H | H | F | H | CF3 | H | H | H | H |
| I-d-2 | H | H | F | H | CF3 | H | H | C2H5 | H |
| I-d-3 | H | H | F | H | CF3 | H | CH3 | H | H |
| I-d-4 | H | H | F | H | CF3 | H | H | CH3 | H |
| I-d-5 | H | H | F | H | CF3 | H | CH3 | H | H |
| I-d-6 | H | NO2 | F | H | CF3 | H | C2H5 | H | H |
| I-d-7 | H | H | F | H | CF3 | H | C3H7-n | H | H |
| I-d-8 | H | F | F | H | CF3 | H | C3H7-i | H | H |
| I-d-9 | H | H | Cl | H | CF3 | H | H | H | H |
| I-d-10 | H | H | Cl | H | CF3 | H | C2H5 | H | H |
| I-d-11 | H | H | Cl | H | CF3 | 4-F | C2H5 | H | OH |
| I-d-12 | H | H | Cl | H | CF3 | H | C2H5 | H | OH |
| I-d-13 | H | H | Cl | H | CF3 | 4-F | C2H5 | H | F |
| I-d-14 | H | CN | Cl | H | CF3 | H | C2H5 | H | F |
| I-d-15 | H | H | Cl | H | CF3 | H | C2H5 | H | CH3SO2O |
| I-d-16 | H | H | Cl | H | CF3 | H | C2H5 | H | CH3C6H5SO2O |
| I-d-17 | H | H | Cl | H | CF3 | H | C3H7-n | H | H |
| I-d-18 | H | H | Cl | H | CF3 | H | CH3 | CH3 | H |
| I-d-19 | H | H | Cl | H | CF3 | H | C2H5 | CH3 | H |
| I-d-20 | H | H | Cl | H | CF3 | H | C3H7-n | CH3 | H |
| I-d-21 | H | Cl | Cl | H | CF3 | H | CH3 | C2H5 | H |
| I-d-22 | H | H | Cl | H | CF3 | H | C2H5 | C2H5 | H |
| I-d-23 | H | H | Cl | H | CF3 | 4-F | C3H7-n | C2H5 | H |
| I-d-24 | H | H | Br | H | CF3 | H | C2H5 | H | H |
| I-d-25 | H | H | I | H | CF3 | H | C2H5 | H | H |
| I-d-26 | H | H | NO2 | H | CF3 | H | C2H5 | H | H |
| I-d-27 | H | H | CH3 | H | CF3 | 4-F | CH3 | H | H |
| I-d-28 | H | H | CN | H | CF3 | H | C2H5 | H | H |
| I-d-29 | H | H | CF3 | H | CF3 | H | C2H5 | H | H |
| I-d-30 | H | H | CH3S | H | CF3 | H | C2H5 | H | H |
| I-d-31 | H | H | CH3SO | H | CF3 | H | C2H5 | H | H |
| I-d-32 | H | H | CH3SO2 | H | CF3 | H | C2H5 | H | H |
| I-d-33 | H | H | C2H5SO2 | H | CF3 | H | C2H5 | H | H |
| I-d-34 | H | H | CF3O | H | CF3 | H | C2H5 | H | H |
| I-d-35 | H | H | C2H5OCO | H | CF3 | H | C2H5 | H | H |
| I-d-36 | H | H | COOH | H | CF3 | H | C2H5 | H | H |
| I-d-37 | H | H | CH3CONH | H | CF3 | H | C2H5 | H | H |
| I-d-38 | H | H | CN | H | CF3 | H | C2H5 | CH3 | H |
| I-d-39 | H | H | CF3 | H | CF3 | H | C2H5 | CH3 | H |
| I-d-40 | H | H | CN | H | CF3 | H | C2H5 | C2H5 | H |
| I-d-41 | H | H | CF3 | H | CF3 | H | C2H5 | C2H5 | H |
| I-d-42 | H | H | CF3 | H | CF3 | H | C2H5 | C3H7-n | H |
| I-d-43 | H | F | F | H | CF3 | H | CH3 | CH3 | H |
| I-d-44 | H | F | F | H | CF3 | H | C2H5 | CH3 | H |
| I-d-45 | H | F | F | H | CF3 | H | C2H5 | H | H |
| I-d-46 | H | F | Cl | H | CF3 | H | C2H5 | H | H |
| I-d-47 | H | Cl | Cl | H | CF3 | H | C2H5 | H | H |
| I-d-48 | H | Cl | Cl | H | CF3 | H | C3H7-n | H | H |
| I-d-49 | H | CN | Cl | H | CF3 | H | C2H5 | H | H |
| I-d-50 | H | CN | F | H | CF3 | H | C3H7-n | H | H |
| I-d-51 | H | CN | CN | H | CF3 | H | C2H5 | H | H |
| I-d-52 | H | F | CF3 | H | CF3 | H | C2H5 | H | H |
| I-d-53 | H | NO2 | CF3 | H | CF3 | H | C3H7-n | H | H |
| I-d-54 | H | NO2 | Cl | H | CF3 | H | C3H7-n | H | H |
| I-d-55 | H | CH3 | Cl | H | CF3 | H | C2H5 | H | H |
| I-d-56 | H | F | CN | H | CF3 | H | C2H5 | H | H |
| I-d-57 | H | F | CN | H | CF3 | H | C3H7-n | H | H |
| I-d-58 | H | Cl | CN | H | CF3 | H | C2H5 | H | H |
| I-d-59 | H | H | Cl | H | CH3S | H | C2H5 | H | H |
| I-d-60 | H | H | Cl | H | CH3SO | H | C3H7-n | H | H |
| I-d-61 | H | H | Cl | H | CH3SO2 | H | C2H5 | H | H |
| I-d-62 | H | H | Cl | H | CN | 4-CN | C2H5 | H | H |
| I-d-63 | H | H | CF3 | H | CN | 4-CN | C2H5 | H | H |

TABLE 25-continued (I-d)

| Compound | R¹ | R² | R³ | R⁴ | R⁹' | R¹⁰' | R⁵' | R⁶' | R⁷' |
|---|---|---|---|---|---|---|---|---|---|
| I-d-64 | H | H | CN | H | CF₃O | H | C₂H₅ | H | H |
| I-d-65 | H | H | NO₂ | H | CF₃ | 4-Cl | C₂H₅ | H | H |

| Intermediate | Melting point (° C.) | ¹H-NMR (300 MHz), CDCl₃, δ (ppm) |
|---|---|---|
| 301 | 35 to 37 | 7.67(1H, d), 7.42-7.45(1H, m), 7.27-7.32(1H, m), 4.88-4.94(1H, m), 3.59-3.61(1H, d), 1.94-2.14(2H, m), 1.05(3H, t) |
| 302 | 119 to 120 | 7.87(1H, d), 7.58-7.61(1H, m), 7.48-7.51(1H, m), 3.24(2H, q), 1.30(3H, t) |
| 303 |  | 4.10-4.19(4H, m), 3.76(3H, s), 2.82-2.94(1H, m), 1.89-2.02(2H, m), 1.31-1.36(6H, m), 0.96-1.01(3H, m) |
| 304 | 98 to 100 | 11.55(1H, br), 7.80(1H, s), 7.46-7.64(4H, m), 2.55(2H, q), 1.23(3H, t) |

TABLE 27

| Compound | Melting point (° C.) | ¹H-NMR(300 MHz), CDCl₃, δ (ppm) |
|---|---|---|
| I-c-1 | 83-85 | 7.76-7.79(2H, m), 7.16(1H, s), 7.53-7.65(4H, m), 7.31-7.38(2H, m), 2.89(2H, q, J=7.3), 1.39(3H, t, J=7.3) |
| I-c-15 | 136-138 | 8.45(1H, d, J=1.7), 8.29-8.34(1H, m), 7.91(1H, s), 7.56-7.85(5H, m), 2.91(2H, q, J=7.6), 1.39(3H, t, J=7.6) |
| I-c-40 | 97-100 | 7.82(1H, s), 7.72(1H, s), 7.53-7.66(3H, m), 7.41-7.48(2H, m), 7.05-7.41(1H, m), 2.45(3H, d, J=1.5) |
| I-c-42 | 83-86 | 7.77(1H, s), 7.70(1H, s), 7.37-7.64(5H, m), 7.04-7.15(1H, m), 2.87(2H, q, J=7.6), 1.36(3H, t, J=7.6) |
| I-c-44 | 79-80 | 7.80(1H, s), 7.70(1H, s), 7.41-7.60(5H, m), 7.05-7.12(1H, m), 2.79-2.84(2H, m), 1.74-1.81(2H, m), 1.06(3H, t, J=7.3) |
| I-c-51 | 108-109 | 7.09-7.84(9H, m) |
| I-c-53 | 91-93 | 7.83(1H, s), 7.72(2H, d, J=2.0), 7.54-7.67(3H, m), 7.44-7.47(1H, m), 7.31-7.44(1H, m), 2.46(3H, d, J=1.5) |
| I-c-54 | 108-110 | 7.61-7.74(4H, m), 7.44-7.47(1H, m), 7.24-7.34(3H, m), 2.85(2H, q, J=7.6), 1.36(3H, t, J=7.6) |
| I-c-55 | 107-108 | 7.30-7.78(8H, m), 2.87(2H, q, J=7.6), 1.36(3H, t, J=7.6) |
| I-c-57 | 73-75 | 7.80(1H, s), 7.70-7.73(2H, m), 7.55-7.60(3H, m), 7.44-7.47(1H, m), 7.30-7.34(1H, m), 2.78-2.84(2H, m), 1.73-1.81(2H, m), 1.05(3H, t, J=7.6) |
| I-c-67 | 99-101 | 7.87(1H, d, J=1.7), 7.75(1H, s), 7.69(1H, s), 7.34-7.63(5H, m), 2.86(2H, q, J=7.6), 1.35(3H, t, J=7.6) |
| I-c-72 | 111-113 | 8.63(1H, d, J=2.2), 8.32(1H, dd, J=6.6, 2.2), 7.86(1H, s), 7.72(1H, s), 7.56-7.68(4H, m), 2.90(2H, q, J=7.6), 1.39(3H, t, J=7.6) |
| I-c-74 | 127-131 | 8.64(1H, d, J=2.5), 8.25-8.34(1H, m), 7.88(1H, s), 7.72(1H, s), 7.56-7.66(4H, m), 2.81-2.87(2H, m), 1.75-1.83(2H, m), 1.08(3H, t, J=7.3) |
| I-c-76 | 84-86 | 7.76(1H, s), 7.71(1H, s), 7.52-7.64(4H, m), 7.40-7.42(1H, m), 7.15-7.17(1H, m), 2.88(2H, q, J=7.3), 2.48(3H, s), 1.36(3H, t, J=7.6) |
| I-c-81 | 123-126 | 8.06(1H, t, J=1.0), 7.84(1H, s), 7.72(1H, t, J=0.7), 7.55-7.68(5H, m), 2.89(2H, q, J=7.6), 1.37(3H, t, J=7.6) |
| I-c-83 | 124-128 | 8.06-8.07(1H, m), 7.86(1H, s), 7.71(1H, s), 7.55-7.68(5H, m), 2.82-2.85(2H, m), 1.71-1.84(2H, m), 1.07(3H, t, J=7.5) |
| I-c-86 | 90-91 | 8.04(1H, s), 7.83(1H, s), 7.54-7.72(6H, m), 2.90(2H, q, J=7.6), 1.38(3H, t, J=7.6) |
| I-c-88 | 62-63 | 8.03(1H, s), 7.84(1H, s), 7.71(1H, s), 7.53-7.64(5H, m), 2.81-2.86(2H, m), 1.67-1.85(2H, m), 1.05(3H, t, J=7.5) |

TABLE 27-continued

| Compound | Melting point (°C.) | ¹H-NMR(300 MHz), CDCl₃, δ (ppm) |
|---|---|---|
| I-c-90 | 94-96 | 7.32-7.76(7H, m), 2.45(3H, s), 2.42-2.45(2H, m), 0.98(3H, t, J=7.6) |
| I-c-111 | 91-93 | 7.35-7.74(7H, m), 2.86(2H, q, J=7.6), 1.36(3H, t, J=7.6) |
| I-c-113 | 89-92 | 7.75(1H, s), 7.69(1H, s), 7.50-7.62(4H, m), 7.34-7.39(1H, m), 2.76-2.82(2H, m), 1.70-1.83(2H, m), 1.05(3H, t, J=7.3) |
| I-c-131 | 91-93 | 7.70-7.71(3H, m), 7.49-7.69(3H, m), 7.35(1H, d, J=0.5), 2.85(2H, q, J=7.6), 1.35(3H, t, J=7.6) |
| I-c-133 | 92-93 | 7.70-7.91(6H, m), 6.57-6.63(2H, m) |
| I-c-135 | 165-166 | 7.96(1H, d, J=5.9), 7.85(1H, s), 7.73(1H, s), 7.56-7.69(3H, m), 7.41-7.43(1H, m), 2.46(3H, d, J=1.5) |
| I-c-137 | 160-163 | 7.98(1H, d, J=5.6), 7.80(1H, s), 7.71(1H, s), 7.55-7.66(3H, m), 7.42(1H, d, J=8.1), 2.87(2H, q, J=7.6), 1.36(3H, t, J=7.6) |
| I-c-139 | 103-106 | 7.98(1H, d, J=5.6), 7.82(1H, s), 7.70(1H, s), 7.57-7.63(3H, m), 7.40-7.43(1H, m), 2.81-2.83(2H, m), 1.73-1.81(2H, m), 1.06(3H, t, J=7.6) |
| I-c-141 | 103-106 | 8.03(1H, s), 7.87(1H, s), 7.57-7.79(5H, m), 2.46(3H, d, J=1.0) |
| I-c-143 | 145-148 | 8.05(1H, s), 7.82(1H, s), 7.56-7.71(5H, m), 2.87(2H, q, J=7.6), 1.36(3H, t, J=7.6) |
| I-c-145 | 120-123 | 8.04(1H, s), 7.84(1H, s), 7.70(2H, d, J=0.5), 7.57-7.66(3H, m), 2.78-2.84(2H, m), 1.70-1.83(2H, m), 1.06(3H |
| I-c-151 | 93-95 | 7.78(1H, s), 7.71-7.72(1H, m), 7.25-7.49(7H, m), 2.90(2H, q, J=7.6), 1.35(3H, t, J=7.6) |
| I-d-10 | | 7.63-7.64(1H, m), 7.25-7.44(6H, m), 3.21-3.30(2H, m), 3.06-3.14(1H, m), 1.82-1.94(2H, m), 0.93(3H, t, J=7.6) |
| I-d-11 | 90-93 | 7.61-7.62(1H, m), 7.20-7.47(5H, m), 6.95-7.00(1H, m), 3.18-3.33(2H, m), 1.93-2.14(2H, m), 0.89(3H, t, J=7.3) |
| I-d-13 | | 7.71(1H, d, J=2.0), 7.32-7.46(4H, m), 7.01-7.08(1H, m), 3.35-3.59(2H, m), 2.10-2.26(2H, m), 0.98(3H, t, J=7.3) |
| I-d-56 | 76-77 | 7.90(1H, d, J=5.6), 7.27-7.45(5H, m), 3.21-3.32(2H, m), 3.12-3.16(1H, m), 1.88-1.94(2H, m), 0.95(3H, t, J=7.6) |

Example 1-3

Synthesis of Compound (I) wherein A is CHR⁵—Y, CR⁵=CR⁶, CR⁵R⁷—CHR⁶ or CHR⁵ in the formula (I))

(Synthesis of Compound (I-e))
(10) Synthesis of 1-(5-chlorobenzoxazol-2-yl)-1-(1-methyl-3-(trifluoromethyl)pyrazo-5-yloxy)propane (Compound (I-e-2))

In 30 ml of acetone was dissolved 0.56 g (2.0 mmol) of 1-(5-chlorobenzoxazol-2-yl)propyl bromide, and to the solution were added 0.41 g (2.5 mmol) of 3-trifluoromethyl-5-hydroxy-1-methyl-pyrazole and 0.42 g (3.1 mmol) of potassium carbonate and the mixture was stirred at 60° C. for 3 hours.

After cooling the mixture to room temperature, 30 ml of toluene was added to the resulting mixture, and the organic layer was washed with water and a saturated saline solution, and dried over anhydrous sodium sulfate.

The resulting extract was concentrated by an evaporator, and isolated by column chromatography (Wakogel C-300 available from Wako Junyaku Co., Ltd., eluted by n-hexane: ethyl acetate=20:1) to obtain 0.64 g (Yield was 89%) of the title compound 1-(5-chlorobenzoxazol-2-yl)-1-(1-methyl-3-(trifluoromethyl)pyrazo-5-yloxy)propane as a pale orangish oily product.

(11) Synthesis of 1-(5-cyano-6-fluorobenzoxazol-2-yl)-1-(5-trifluoromethylisoxazol-3-yloxy)propane (Compound (1-e-40))

In 0.30 ml of acetonitrile was dissolved 0.7 g (2.5 mmol) of 1-(5-cyano-6-fluorobenzoxazol-2-yl)-1-bromopropane, and to the solution were added 0.42 g (2.7 mmol) of 5-trifluoromethyl-2-hydroxyisoxazole and 0.51 g (3.7 mmol) of potassium carbonate and the mixture was stirred under reflux for 2 hours.

After cooling the mixture to room temperature, 30 ml of toluene was added to the resulting mixture, and the organic layer was washed with water and a saturated saline solution, and dried over anhydrous sodium sulfate.

The resulting extract was concentrated by an evaporator, and isolated by column chromatography (Wakogel C-300 available from Wako Junyaku Co., Ltd., eluted by n-hexane: ethyl acetate=20:1) to obtain 0.72 g (Yield was 82%) of the title compound 1-(5-cyano-6-fluorobenzoxazol-2-yl)-1-(5-trifluoromethylisoxazol-3-yloxy)propane as a pale yellowish oily product.

(12): Synthesis of 1-(5-chlorobenzoxazol-2-yl)-1-(4-methyl-2-methylthiopyrimidin-6-yloxy)propane ((I-e-64))

To 15 ml of DMF was dissolved 0.6 g of 1-(5-chlorobenzoxazol-2-yl)propan-1-ol and 0.11 g of sodium hydride (60%) was added to the solution.

After stirring the mixture at room temperature for 15 minutes, 0.4 g of 4-chloro-6-methyl-2-methylthiopyrimidine was added to the mixture.

After stirring at room temperature for 3 hours, the reaction mixture was poured into water and the mixture was neutralized by 1N aqueous hydrochloric acid.

To the mixture was added 30 ml of toluene, the organic layer was washed with water and a saturated saline solution, and dried over anhydrous sodium sulfate.

The resulting extract was, after concentration by an evaporator, isolated by column chromatography (Wakogel C-300 available from Wako Junyaku Co., Ltd., eluted by n-hexane: ethyl acetate=20:1) to obtain 0.56 g (an yield was 70%) of the title compound 1-(5-chlorobenzoxazol-2-yl)-1-(4-methyl-2-methylthiopyrimidin-6-yloxy)propane as yellowish oily product.

(Synthesis of Compoumd (I-f)
(13) Synthesis of 1-(5-chlorobenzoxazol-2-yl)-1-(4-methylimidazol-1-yl) propane (I-f-1))

In 15 ml of DMF was dissolved 0.4 g (1.5 mmol) of 1-(5-chlorobenzoxazol-2-yl)propyl bromide, and 0.07 g of sodium hydride (60%) was added to the solution. After stirring at room temperature for 15 minutes, 0.13 g (1.7 mmol) of 4-methyl-1,3-imidazole was added to the mixture.

After stirring at room temperature for 5 hours, the reaction mixture was poured into water, and the mixture was neutralized with 1N aqueous hydrochloric acid.

To the mixture was added 30 ml of ethyl ether, the organic layer was washed with water and a saturated saline solution, and dried over anhydrous sodium sulfate. The resulting extract was, after concentration by an evaporator, isolated by column chromatography (Wakogel C-300 available from Wako Junyaku Co., Ltd., eluted by n-hexane:ethyl acetate=20:1) to obtain 0.26 g (an yield was 55%) of the desired compound 1-(5-chlorobenzoxazol-2-yl)-1-(4-methylimidazol-1-yl)propane as yellowish oily product.

Reference Example 1

(1) Synthesis of 1-(5-chlorobenzoxazol-2-yl)propyl bromide

In 200 ml of xylene was dissolved 34.0 g (0.24 mol) of 2-amino-4-chlorophenol, and to the solution were added 54.4 g (0.24 mol) of 2-bromobutanoic acid chloride and 2.0 g (0.012 mol) of p-toluenesulfonic acid, and the resulting mixture was refluxed for 6 hours.

After cooling to room temperature, the organic layer was washed with 2N aqueous sodium hydroxide solution, water and a saturated saline solution, and dried over anhydrous sodium sulfate.

After removing toluene, the resulting residue was isolated by column chromatography (Wakogel C-300 available form Wako Junyaku Co., Ltd., eluted by n-hexane:ethyl acetate=9:1) to obtain 56.8 g (an yield was 90%) of the desired compound oily product.

Reference Example 2

(1) Synthesis of 2-propionyl(5-chlorobenzoxazole)

In 100 ml of dichloromethane was dissolved 9.6 g (75.6 mmol) of oxalyl chloride, and the solution was stirred at –78° C.

To the solution was gradually added dropwise a mixed solution of dichloromethane (26.4 ml) and DMSO (7.1 ml), and the resulting mixture was stirred for 10 minutes.

Further, a dichloromethane (50 ml) solution containing 8 g (38.7 mmol) of 1-(5-chlorobenzoxazol-2-yl)propanol was gradually added dropwise to the mixture, and the resulting mixture was stirred at –78° C. for 15 minutes.

Then, the mixture was stirred at –45° C. for one hour, and 40 ml of triethylamine was gradually added dropwise to the mixture and the resulting mixture was stirred at 0° C. for 20 minutes. After completion of stirring, 120 ml of a saturated aqueous ammonium chloride solution was added to the mixture, and the organic layer was extracted with ethyl acetate.

The resulting extract was dried over anhydrous sodium sulfate, and after concentration by an evaporator, the residue was isolated by column chromatography (Wakogel C-300 available from Wako Junyaku Co., Ltd., eluted by n-hexane:ethyl acetate=10:1) to obtain 2.9 g (an yield was 37%) of the desired compound 2-propionyl(5-chlorobenzoxazole) as orange crystal. $^1$H-NMR (300 MHz), CDCl$_3$, δ (ppm)

7.87 (1H, s), 7.48 to 7.61 (2H, m), 3.20 to 3.28 (2H, m), 1.30 (3H, t)

According to the method mentioned in the above (1), other Compounds (I) and intermediate in the tables were synthesized.

Compounds (I) synthesized as mentioned above were shown in Tables 28 and 29, and their physical properties are shown in Tables 28 to 30.

Also, (W-1-1) to (W-26-1) shown at the column of W in Tables 28 and 29 are as shown by the following formulae.

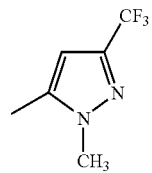 (w-1-1)

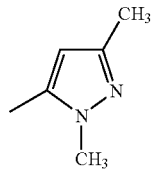 (w-1-2)

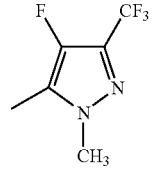 (w-1-3)

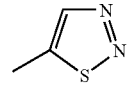 (w-5-1)

 (w-6-1)

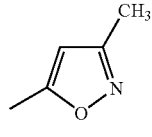 (w-6-2)

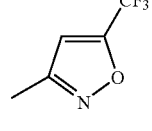 (w-7-1)

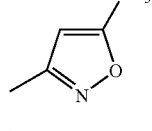 (w-7-2)

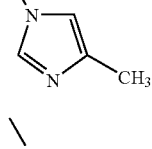 (w-8-1)

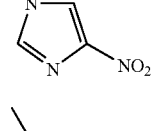 (w-8-2)

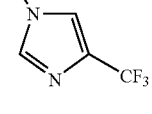 (w-8-3)

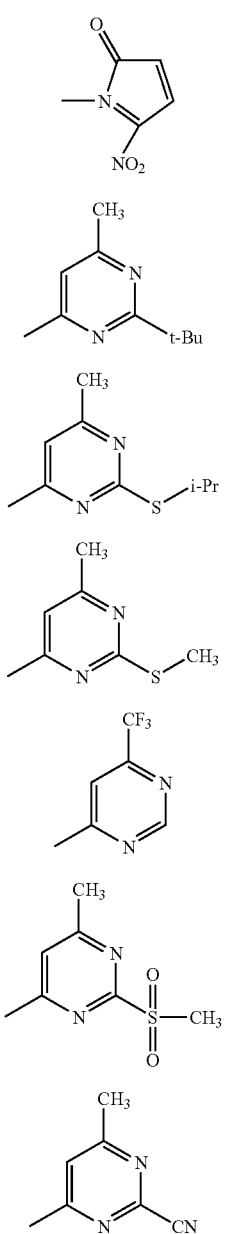

(w-9-1)

(w-17-1)

(w-17-2)

(w-17-3)

(w-17-4)

(w-17-5)

(w-17-6)

TABLE 28

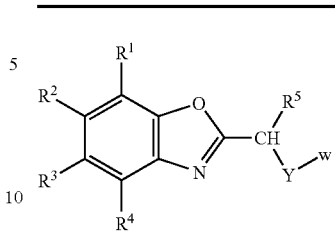

(I-e)

| Compound | R¹ | R² | R³ | R⁴ | R⁵ | Y | w | Physical properties |
|---|---|---|---|---|---|---|---|---|
| I-e-1 | H | H | Cl | H | CH₃ | O | w-1-1 | |
| I-e-2 | H | H | Cl | H | C₂H₅ | O | w-1-1 | See Table 30 |

TABLE 28-continued (I-e)

| Compound | R¹ | R² | R³ | R⁴ | R⁵ | Y | w | Physical properties |
|---|---|---|---|---|---|---|---|---|
| I-e-3 | H | H | Cl | H | n-C₃H₇ | O | w-1-1 | |
| I-e-4 | H | H | Cl | H | n-C₄H₉ | O | w-1-1 | |
| I-e-5 | H | H | F | H | C₂H₅ | O | w-1-1 | |
| I-e-6 | H | F | F | H | n-C₃H₇ | O | w-1-1 | |
| I-e-7 | H | Cl | CN | H | n-C₃H₇ | O | w-1-1 | |
| I-e-8 | H | H | NO₂ | H | C₂H₅ | O | w-1-1 | |
| I-e-9 | H | H | CN | H | C₂H₅ | O | w-1-1 | |
| I-e-10 | H | F | CN | H | C₂H₅ | O | w-1-1 | m.p. 102-103° C. |
| I-e-11 | H | Cl | CN | H | C₂H₅ | O | w-1-1 | m.p. 100-102° C. |
| I-e-12 | H | H | Cl | H | C₂H₅ | S | w-1-1 | See Table 30 |
| I-e-13 | H | H | Cl | H | n-C₃H₇ | S | w-1-1 | |
| I-e-14 | H | F | CN | H | C₂H₅ | O | w-1-2 | m.p. 82-84° C. |
| I-e-15 | H | F | F | H | n-C₃H₇ | O | w-1-2 | |
| I-e-16 | H | H | Cl | H | C₂H₅ | O | w-1-3 | |
| I-e-17 | H | H | Cl | H | n-C₃H₇ | O | w-1-3 | |
| I-e-18 | H | F | F | H | C₂H₅ | O | w-1-3 | |
| I-e-19 | H | F | F | H | n-C₃H₇ | O | w-1-3 | |
| I-e-20 | H | H | Cl | H | C₂H₅ | S | w-5-1 | m.p. 138-141 |
| I-e-21 | H | H | Cl | H | n-C₃H₇ | S | w-5-1 | |
| I-e-22 | H | F | F | H | C₂H₅ | O | w-6-1 | |
| I-e-23 | H | F | F | H | n-C₃H₇ | O | w-6-1 | |
| I-e-24 | H | H | Cl | H | C₂H₅ | O | w-6-1 | |
| I-e-25 | H | H | Cl | H | n-C₃H₇ | O | w-6-1 | |
| I-e-26 | H | H | Cl | H | C₂H₅ | S | w-6-1 | |
| I-e-27 | H | H | Cl | H | n-C₃H₇ | S | w-6-1 | |
| I-e-28 | H | F | CN | H | C₂H₅ | O | w-6-1 | See Table 30 |
| I-e-29 | H | F | CN | H | n-C₃H₇ | O | w-6-1 | |
| I-e-30 | H | H | Cl | H | C₂H₅ | O | w-6-2 | |
| I-e-31 | H | H | Cl | H | n-C₃H₇ | O | w-6-2 | |
| I-e-32 | H | F | F | H | C₂H₅ | O | w-6-2 | |
| I-e-33 | H | F | F | H | n-C₃H₇ | O | w-6-2 | |
| I-e-34 | H | H | Cl | H | C₂H₅ | O | w-7-1 | |
| I-e-35 | H | H | Cl | H | n-C₃H₇ | O | w-7-1 | |
| I-e-36 | H | H | Cl | H | C₂H₅ | S | w-7-1 | |
| I-e-37 | H | H | Cl | H | n-C₃H₇ | S | w-7-1 | |
| I-e-38 | H | Cl | CN | H | C₂H₅ | O | w-7-1 | |
| I-e-39 | H | Cl | CN | H | n-C₃H₇ | O | w-7-1 | |
| I-e-40 | H | F | CN | H | C₂H₅ | O | w-7-1 | See Table 30 |
| I-e-41 | H | F | CN | H | n-C₃H₇ | O | w-7-1 | |
| I-e-42 | H | H | Cl | H | C₂H₅ | O | w-7-2 | |
| I-e-43 | H | H | Cl | H | n-C₃H₇ | O | w-7-2 | |
| I-e-44 | H | F | F | H | C₂H₅ | O | w-7-2 | |
| I-e-45 | H | F | F | H | n-C₃H₇ | O | w-7-2 | |
| I-e-46 | H | H | Cl | H | C₂H₅ | O | w-8-2 | |
| I-e-47 | H | H | Cl | H | n-C₃H₇ | O | w-8-2 | |
| I-e-48 | H | F | F | H | C₂H₅ | O | w-8-2 | |
| I-e-49 | H | F | F | H | n-C₃H₇ | O | w-8-2 | |
| I-e-50 | H | H | Cl | H | C₂H₅ | O | w-8-2 | m.p. 146-148° C. |
| I-e-51 | H | H | Cl | H | n-C₃H₇ | O | w-8-2 | |
| I-e-52 | H | H | Cl | H | CH₃ | O | w-17-1 | |
| I-e-53 | H | H | Cl | H | C₂H₅ | O | w-17-1 | See Table 30 |
| I-e-54 | H | H | Cl | H | CH₃ | O | w-17-2 | |
| I-e-55 | H | H | Cl | H | C₂H₅ | O | w-17-2 | See Table 30 |
| I-e-56 | H | H | F | H | C₂H₅ | O | w-17-2 | |
| I-e-57 | H | F | F | H | C₂H₅ | O | w-17-2 | |
| I-e-58 | H | H | NO₂ | H | C₂H₅ | O | w-17-2 | |
| I-e-59 | H | H | CN | H | C₂H₅ | O | w-17-2 | |
| I-e-60 | Cl | H | H | H | C₂H₅ | O | w-17-2 | |
| I-e-61 | H | Cl | H | H | C₂H₅ | O | w-17-2 | |

TABLE 28-continued (I-e)

| Compound | $R^1$ | $R^2$ | $R^3$ | $R^4$ | $R^5$ | Y | w | Physical properties |
|---|---|---|---|---|---|---|---|---|
| I-e-62 | H | H | Cl | H | $C_2H_5$ | NH | w-17-2 | |
| I-e-63 | H | H | Cl | H | $C_2H_5$ | S | w-17-2 | |
| I-e-64 | H | H | Cl | H | $C_2H_5$ | O | w-17-3 | See Table 30 |
| I-e-65 | H | F | CN | H | n-$C_3H_7$ | O | w-17-3 | See Table 30 |
| I-e-66 | H | H | Cl | H | $C_2H_5$ | O | w-17-4 | See Table 30 |
| I-e-67 | H | H | Cl | H | n-$C_3H_7$ | O | w-17-4 | |
| I-e-68 | H | H | CN | H | n-$C_3H_7$ | O | w-17-5 | See Table 30 |
| I-e-69 | H | F | F | H | n-$C_3H_7$ | O | w-17-5 | |
| I-e-70 | H | H | CN | H | n-$C_3H_7$ | O | w-17-6 | See Table 30 |
| I-e-71 | H | F | F | H | n-$C_3H_7$ | O | w-17-6 | |

TABLE 29

(I-f)

| Compound | $R^1$ | $R^2$ | $R^3$ | $R^4$ | $R^5$ | w | Physical properties |
|---|---|---|---|---|---|---|---|
| I-f-1 | H | H | Cl | H | $C_2H_5$ | w-8-1 | See Table 30 |
| I-f-2 | H | H | Cl | H | n-$C_3H_7$ | w-8-1 | |
| I-f-3 | H | H | Cl | H | $C_2H_5$ | w-8-2 | See Table 30 |
| I-f-4 | H | H | Cl | H | n-$C_3H_7$ | w-8-2 | |
| I-f-5 | H | H | Cl | H | $C_2H_5$ | w-8-2 | m.p. 110-112° C. |
| I-f-6 | H | H | Cl | H | n-$C_3H_7$ | w-8-2 | |
| I-f-7 | H | H | Cl | H | $C_2H_5$ | w-9-1 | m.p. 178-179° C. |
| I-f-8 | H | H | Cl | H | n-$C_3H_7$ | w-9-1 | |

TABLE 30

| Compound | $^1$H-NMR(300 MHz), CDCl$_3$, δ (ppm) |
|---|---|
| I-e-2 | 7.74(1H, s), 7.22 to 7.49(2H, m), 6.41(1H, s), 6.17(1H, t), 2.38(3H, s), 2.22 to 2.35(2H, m), 1.11(3H, t) |
| I-e-12 | 7.65(1H, s), 7.43 to 7.14(4H, m), 4.12 to 4.11(1H, m), 3.72(3H, s), 2.25 to 2.04(2H, m), 1.28 to 0.98(3H, m) |
| I-e-28 | 8.04(1H, d), 7.46(1H, d), 5.65(1H, s), 5.57(1H, t), 2.32 to 2.41(2H, m), 1.14(3H, t) |
| I-e-40 | 8.00(1H, d), 7.43(1H, d), 6.45(1H, s), 5.84(1H, t), 2.24 to 2.33(2H, m), 1.09(3H, t) |
| I-e-53 | 7.66(1H, d), 7.26 to 7.42(2H, m), 5.86(1H, s), 6.12(1H, t), 2.41(1H, s), 2.20 to 2.34(2H, m), 1.16(9H, s), 1.09(3H, t) |
| I-e-55 | 7.68(1H, s), 7.28 to 7.43(2H, d), 6.40(1H, s), 5.24(1H, t), 3.66 to 3.73(1H, m), 2.37(3H, s), 2.17 to 2.25(2H, m), 1.37(3H, m), 1.07 to 1.11(6H, m) |
| I-e-64 | 7.68(1H, s), 7.26 to 7.44(2H, m), 6.41(1H, s), 6.17(1H, t), 3.76(3H, s), 2.35(3H, s), 2.18 to 2.25(2H, m), 1.08(3H, t) |
| I-e-65 | 8.03(1H, s), 7.59 to 7.70(2H, m), 6.41(1H, s), 6.25 to 6.41(1H, m), 2.38(3H, s), 2.34(3H, s), 2.11 to 2.22(2H, m), 1.52 to 1.59(2H, m), 0.98(3H, t) |
| I-e-66 | 8.82(1H, s), 7.69(1H, s), 7.25 to 7.46(3H, m), 6.33(1H, t), 2.24 to 2.32(2H, m), 1.11(3H, t) |
| I-e-68 | 8.02(1H, s), 7.62 to 7.69(2H, m), 6.92(1H, s), 6.36(1H, t), 3.17(3H, s ), 2.59(3H, s), 2.18 to 2.28(2H, m), 1.50 to 1.58(2H, m), 1.02(3H, t) |
| I-e-70 | 8.03(1H, s), 7.63 to 7.70(2H, m), 6.93(1H, s), 6.37(1H, t), 2.53(3H, s), 2.18 to 2.25(2H, m), 1.50 to 1.57(2H, m), 1.02(3H, t) |
| I-f-1 | 7.26 to 7.72(4H, m), 5.22(1H, t), 2.26 to 2.45(2H, m), 2.22(3H, s), 1.02(3H, t) |
| I-f-2 | 8.00(1H, d), 7.26 to 7.72(3H, m), 5.38(1H, t), 2.51 to 2.58(2H, m), 2.22(3H, s), 1.06(3H, t) |

Example 2

Preparation of Preparations (1) Preparation of Granule 5 parts by weight of Compound 1-a-1 was uniformly mixed with 35 parts by weight of bentonite, 57 parts by weight of talc, 1 part by weight of sodium decylbenzenesulfonate and 2 parts by weight of sodium lignosulfonate, and then, the mixture was kneaded with addition of a small amount of water, followed by subjected to granulation and drying, to obtain a granule.

(2) Preparation of Wettable Powder 10 parts by weight of Compound 1-a-1 was uniformly mixed with 70 parts by weight of kaolin clay, 18 parts by weight of white carbon, 1.5 parts by weight of sodium dodecylbenzene-sulfonate and 0.5 part by weight of sodium β-naphthalene sulfonate-formalin condensate, and then, the mixture was pulverized by air mill to obtain a wettable powder.

(3). Preparation of Emulsion

To the mixture of 20 parts by weight of Compound 1-a-1 and 70 parts by weight of xylene was added 10 parts by weight of Sorpol 3005X (trade name, produced by Toho Kagaku Kogyo), and the mixture was uniformly mixed and dissolved to obtain an emulsion.

(4) Preparation of Dust 5 parts by weight of Compound 1-a-1, 50 parts by weight of talc and 45 parts by weight of kaolin clay were uniformly mixed to obtain a dust.

Example 3

Herbicidal Activity Test (1) Herbicidal Test for Paddy Field

Wagner pots, each having an area of 1/5000 are, were packed with Ube soil (alluvial soil) and planted with seeds or tubers of young rice plant, barnyard grass, bulrush, *Cyperus serotinus* Rottb., arrowhead and *monochoria*. Then, the pots were filled with water to a depth of 3 cm.

Each wettable powder of the desired Compounds (I) shown in Tables 1 to 21, 24, 25, 28 and 29 prepared in accordance with Example 2 was diluted with water containing a surfactant (0.05%) and subjected to dropwise addition treatment by using pipet so that an effective concentration of the compound (I) in each herbicide became 500 g/ha at 1.5 leaf stage of barnyard grass.

These plants were controlled in a glass house at an average temperature of 25° C. for 3 weeks, and then herbicidal effects thereof were investigated.

The herbicidal effects are evaluated according to the following 6 ranks as compared with non-treated district. (0: normal development, 1: Less damaged, 2: Slightly damaged, 3: Moderately damaged, 4: Severely damaged, 5: All killed). Incidentally, "-" in the column means not investigated.

The degrees of these effects are shown in Table 31.

TABLE 31

| Compound | Effects | | | | | |
|---|---|---|---|---|---|---|
| | Young rice plant | Barnyard-grass | Bulrush | Cyperus serotinus Rottb. | Arrowhead | Monochoria |
| I-a-1 | 3 | 4 | 2 | 2 | 1 | — |
| I-a-2 | 2 | 4 | 3 | — | 1 | — |
| I-a-3 | 2 | 3 | 0 | 0 | 0 | — |
| I-a-4 | 0 | 0 | 0 | 0 | 0 | — |
| I-a-6 | 3 | 4 | — | 2 | 0 | — |
| I-a-7 | 0 | 1 | 0 | 0 | 0 | — |
| I-a-13 | 2 | 2 | 0 | 0 | 1 | — |
| I-a-18 | 1 | 3 | 0 | 0 | 0 | — |
| I-c-1 | 3 | 3 | 3 | 3 | — | — |
| I-c-42 | 3 | 5 | 5 | — | — | — |
| I-c-54 | 3 | 5 | 3 | 3 | — | — |
| I-c-76 | 3 | 4 | 3 | — | — | — |
| I-c-81 | 3 | 5 | 5 | 4 | — | — |
| I-c-86 | 3 | 5 | 4 | 3 | — | — |
| I-c-111 | 3 | 5 | 4 | 1 | — | — |
| I-c-137 | 1 | 4 | 4 | 2 | — | — |
| I-c-139 | 2 | 4 | 3 | 1 | — | — |
| I-c-143 | 2 | 5 | 5 | — | — | — |
| I-c-145 | 2 | 4 | 3 | — | — | — |

TABLE 31-continued

| Compound | Effects | | | | | |
|---|---|---|---|---|---|---|
| | Young rice plant | Barnyard-grass | Bulrush | Cyperus serotinus Rottb. | Arrowhead | Monochoria |
| 1-e-10 | 1 | 5 | — | — | — | 4 |
| 1-e-11 | 0 | 4 | — | — | — | 4 |
| 1-e-12 | 0 | — | — | — | — | 5 |
| 1-e-28 | 0 | 5 | — | — | — | 5 |
| 1-e-64 | 0 | — | — | — | — | 4 |
| 1-e-66 | 0 | 2 | — | — | — | 5 |
| 1-e-70 | 0 | — | — | — | — | 3 |
| I-f-9 | 0 | — | — | — | — | 5 |

(2) Soil Treatment Test for Upland Field

Wagner pots, each having an area of 1/5000 are, were packed with Ube soil (alluvial soil), and then each seed of corn, soybean, cotton, wheat, solgum, sugar beat, Large crabgrass, barnyard grass, green foxtail, blackgrass, annual bluegrass, common lambsquarters, livid amaranth, velvetleaf, morning glory, common Cocklebur (*Xanthium strumarium*) and sicklepod (*Cassia obtusifolia*) were planted and covered with soil.

Each wettable powder of the desired compounds (I) shown in Tables 1 to 21, 24, 25, 28 and 29 prepared in accordance with Example 2 was diluted with water containing a surfactant (0.05%) and uniformly sprayed on the surface of each soil so that an effective concentration of the compound (I) in each herbicide became 500 g/ha.

These plants were controlled in a glass house at an average temperature of 25° C. for 3 weeks, and then herbicidal effects thereof were investigated.

The herbicidal effects were evaluated according to the evaluation method described in the above (1).

The degree of these effects is shown in Table 32.

TABLE 32

| Compound | Effects | | | | | | | | |
|---|---|---|---|---|---|---|---|---|---|
| | Corn | Soybean | Sotton | Wheat | Solgum | Sugar beat | Large crabgrass | Barnyardgrass | Green foxtail |
| I-a-1 | 0 | — | — | 1 | 2 | 5 | 5 | 4 | 5 |
| I-a-2 | 2 | — | — | 1 | 1 | 5 | 5 | 4 | 5 |
| I-a-3 | 1 | 3 | — | 1 | 1 | 5 | 5 | 4 | 5 |
| I-a-4 | 0 | — | — | — | 0 | 0 | 0 | 3 | 1 |
| I-a-6 | 0 | — | 1 | 1 | 0 | 5 | 5 | 5 | 5 |
| I-a-7 | 0 | 2 | 0 | 0 | 0 | 5 | 5 | 4 | 5 |
| I-a-13 | 1 | — | — | 1 | 0 | 5 | 5 | 4 | 5 |
| I-c-1 | 1 | — | — | 0 | 1 | — | 5 | 5 | 5 |
| I-c-15 | 1 | — | — | 1 | 1 | 2 | 5 | 4 | 5 |
| I-c-40 | 0 | — | — | 0 | 2 | 1 | 5 | 5 | 5 |
| I-c-42 | 1 | — | — | 0 | 5 | 5 | 5 | 5 | 5 |
| I-c-44 | 2 | — | — | 2 | 3 | 5 | 5 | 5 | 5 |
| I-c-53 | 1 | — | — | 1 | 0 | 5 | 5 | 5 | 5 |
| I-c-54 | 1 | 5 | 3 | 1 | 2 | 5 | 5 | 5 | 5 |
| I-c-55 | 1 | 4 | — | 0 | 1 | 5 | 5 | 5 | 5 |
| I-c-57 | 2 | — | — | 2 | 2 | — | 5 | 5 | 5 |
| I-c-67 | 2 | — | — | 1 | 5 | 5 | 5 | 5 | 5 |
| I-c-72 | 2 | 5 | — | 2 | 3 | 5 | 5 | 5 | 5 |
| I-c-74 | 2 | — | — | 1 | 2 | 5 | 5 | 5 | 5 |
| I-c-76 | 1 | — | — | 0 | 3 | 0 | 5 | 4 | 5 |
| I-c-81 | 2 | 3 | — | 3 | 2 | 5 | 5 | 5 | 5 |
| I-c-83 | 2 | — | — | 1 | 1 | 5 | 5 | 4 | 5 |
| I-c-86 | 1 | 0 | — | 0 | 1 | 5 | 5 | 5 | 5 |
| I-c-88 | 3 | 5 | — | 2 | 4 | 5 | 5 | 5 | 5 |
| I-c-111 | 2 | 5 | — | 5 | 3 | 5 | 5 | 5 | 5 |

TABLE 32-continued

| | | | | | | | | | |
|---|---|---|---|---|---|---|---|---|---|
| I-c-113 | 2 | — | — | 2 | 2 | 5 | 5 | 5 | 5 |
| I-c-131 | 1 | 1 | — | 1 | 3 | 5 | 5 | 5 | 5 |
| I-c-135 | 1 | 2 | — | 1 | 1 | 5 | 5 | 4 | 5 |
| I-c-137 | 2 | 3 | — | 1 | 2 | 5 | 5 | 5 | 5 |
| I-c-139 | 2 | 5 | — | 2 | 3 | 5 | 5 | 5 | 5 |
| I-c-141 | 0 | — | — | 0 | 0 | 5 | 5 | 4 | 5 |
| I-c-143 | 1 | 3 | — | 1 | 3 | 5 | 5 | 4 | 5 |
| I-c-145 | 0 | 0 | — | 1 | 1 | 5 | 5 | 4 | 5 |
| I-d-13 | 0 | — | 0 | 0 | 0 | 5 | 5 | 2 | 5 |
| 1-e-2 | 0 | 0 | — | 0 | — | — | 3 | — | 3 |
| 1-e-10 | 1 | 2 | — | 0 | — | — | 5 | 4 | 5 |
| 1-e-11 | 0 | — | — | 0 | — | — | 5 | 4 | 5 |
| 1-e-12 | 0 | 0 | — | 0 | — | — | 5 | 3 | 2 |
| 1-e-28 | 0 | 1 | — | 0 | — | — | 5 | 4 | 5 |
| 1-e-40 | 1 | 2 | — | 0 | — | — | 5 | 5 | 5 |
| 1-e-65 | 0 | 0 | — | 0 | — | — | 4 | — | 4 |
| 1-e-70 | 0 | 0 | — | 0 | — | — | 2 | — | — |

| | Effects | | | | | | | |
|---|---|---|---|---|---|---|---|---|
| Compound | Blackgrass | Annual bluegrass | Common lambsquarters | Livid amaranth | Velvetleaf | Morning glory | Common Cocklebur | Sicklepod |
| I-a-1 | 4 | 5 | 5 | 5 | 3 | 4 | 5 | 3 |
| I-a-2 | 5 | 5 | 5 | 5 | 5 | 5 | 3 | 3 |
| I-a-3 | 4 | 5 | 5 | 5 | 3 | 3 | 2 | 5 |
| I-a-4 | 0 | 0 | 0 | — | 1 | 1 | — | 0 |
| I-a-6 | 5 | 5 | 5 | 5 | 2 | 5 | 0 | 1 |
| I-a-7 | 4 | 5 | 5 | 5 | 0 | 1 | 0 | 3 |
| I-a-13 | 4 | 5 | 5 | 5 | 5 | 4 | 3 | — |
| I-c-1 | 5 | 5 | 5 | 5 | — | 1 | — | — |
| I-c-15 | 5 | 5 | 5 | 5 | 2 | 2 | — | — |
| I-c-40 | 4 | 5 | 5 | 5 | — | 3 | — | — |
| I-c-42 | 5 | 5 | 5 | 5 | 5 | 3 | — | — |
| I-c-44 | 5 | 5 | 5 | 5 | 3 | 2 | — | — |
| I-c-53 | 5 | 5 | 5 | 5 | 1 | 2 | — | — |
| I-c-54 | 5 | 5 | 5 | 5 | 5 | 5 | — | — |
| I-c-55 | 5 | 5 | 5 | 5 | 5 | 5 | — | — |
| I-c-57 | 5 | 5 | 5 | 5 | 5 | 3 | — | — |
| I-c-67 | 5 | 5 | 5 | 5 | 5 | 4 | — | — |
| I-c-72 | 5 | 5 | 5 | 5 | 5 | 4 | — | — |
| I-c-74 | 4 | 5 | 5 | 5 | 5 | 5 | — | — |
| I-c-76 | 5 | 5 | 5 | 5 | 5 | 1 | — | — |
| I-c-81 | 5 | 5 | 5 | 5 | 5 | 5 | — | — |
| I-c-83 | 5 | 5 | 5 | 5 | 5 | 5 | — | — |
| I-c-86 | 5 | 5 | 5 | 5 | 5 | 5 | — | — |
| I-c-88 | 5 | 5 | 5 | 5 | 5 | 5 | — | — |
| I-c-111 | 5 | 5 | 5 | 5 | 5 | 4 | — | — |
| I-c-113 | 5 | 5 | 5 | 5 | 5 | 4 | — | — |
| I-c-131 | 5 | 5 | 5 | 5 | 5 | 5 | — | — |
| I-c-135 | 5 | 5 | 5 | 5 | 5 | 4 | — | — |
| I-c-137 | 5 | 5 | 5 | 5 | 5 | 5 | — | — |
| I-c-139 | 5 | 5 | 5 | 5 | 5 | 5 | — | — |
| I-c-141 | 4 | 5 | 5 | 5 | 5 | 5 | — | — |
| I-c-143 | 4 | 5 | 5 | 5 | 5 | 5 | — | — |
| I-c-145 | 5 | 5 | 5 | 5 | 5 | 5 | — | — |
| I-d-13 | 4 | 5 | 5 | 5 | 5 | 1 | — | — |
| 1-e-2 | — | 3 | 2 | 5 | — | — | — | — |
| 1-e-10 | — | 5 | 5 | 5 | — | — | — | — |
| 1-e-11 | — | 5 | 5 | 5 | — | — | — | — |
| 1-e-12 | — | 4 | 3 | 4 | — | — | — | — |
| 1-e-28 | — | 5 | 5 | 5 | — | — | — | — |
| 1-e-40 | — | 5 | 5 | 5 | — | — | — | — |
| 1-e-65 | — | — | 2 | 5 | — | — | — | — |
| 1-e-70 | — | — | 3 | 5 | — | — | — | — |

(3) Foliar Spread Test for Upland Field

Wagner pots, each having an area of 1/5000 are, were packed with volcanic ash soil and then each seed of corn, soybean, cotton, wheat, solgum, sugar beat, Large crabgrass, barnyardgrjass, green foxtail, blackgrass, annual bluegrass, common lambsquarters, livid amaranth, velvetleaf, morning glory, *Xanthium pensylvanicum* and *Cassia obtusifolia* was planted, covered with soil and grown in a glass house at an average temperature of 25° C. for about 2 weeks.

Each wettable powder of the desired compounds (I) shown in Tables 1 to 21, 24, 25, 28 and 29 prepared in accordance with Example 2 was diluted to 500 ppm with water containing a surfactant (0.5%) and then uniformly sprayed on the above respective plants.

After these plants were controlled in a glass house at an average temperature of 25° C. for 3 weeks, the herbicidal effects thereof were investigated.

The herbicidal effects were evaluated according to the evaluation method described in the above (1).

The degree of these effects is shown in Table 33.

TABLE 33

| | Effects | | | | | | | | |
|---|---|---|---|---|---|---|---|---|---|
| Compound | Corn | Soybean | Sotton | Wheat | Solgum | Sugar beat | Large crabgrass | Barnyardgrass | Green foxtail |
| I-a-1 | 2 | 5 | 4 | 2 | 2 | 4 | 4 | 3 | 5 |
| I-a-2 | 2 | 3 | 4 | 2 | 2 | 4 | 4 | 3 | 5 |
| I-a-3 | 1 | 3 | 4 | 1 | 1 | 4 | 2 | 1 | 3 |
| I-a-4 | 1 | 2 | 2 | 1 | 1 | 4 | 1 | 0 | 1 |
| I-a-6 | 3 | 5 | 3 | 3 | 3 | 5 | 5 | 5 | 5 |
| I-a-7 | 1 | 3 | 3 | 2 | 2 | 5 | 3 | 1 | 3 |
| I-a-13 | 2 | 3 | 5 | 2 | 2 | 4 | 3 | 2 | 5 |
| I-a-18 | 1 | 3 | 4 | 1 | 1 | 4 | 2 | 1 | 5 |
| I-c-1 | 2 | 5 | 2 | 1 | 1 | 3 | 3 | 1 | 3 |
| I-c-15 | 2 | 5 | 3 | 2 | 2 | 4 | 4 | 3 | 4 |
| I-c-40 | 2 | 4 | 1 | 1 | 1 | 4 | 3 | 1 | 2 |
| I-c-42 | 3 | 5 | 3 | 2 | 2 | 4 | 4 | 2 | 4 |
| I-c-44 | 2 | 5 | 3 | 2 | 2 | 3 | 4 | 2 | 4 |
| I-c-53 | 3 | 4 | 3 | 1 | 1 | 5 | 4 | 1 | 5 |
| I-c-54 | 3 | 4 | 3 | 2 | 3 | 5 | 4 | 2 | 4 |
| I-c-55 | 3 | 5 | 4 | 3 | 3 | 5 | 4 | 4 | 5 |
| I-c-57 | 2 | 5 | 4 | 2 | 2 | 3 | 4 | 3 | 5 |
| I-c-67 | 3 | 5 | 5 | 2 | 3 | 4 | 4 | 3 | 4 |
| I-c-72 | 3 | 5 | 4 | 2 | 3 | 4 | 4 | 3 | 4 |
| I-c-74 | 2 | 5 | 5 | 2 | 2 | 4 | 4 | 2 | 5 |
| I-c-76 | 2 | 5 | 3 | 2 | 2 | 4 | 4 | 2 | 4 |
| I-c-81 | 3 | 5 | 4 | 2 | 3 | 4 | 4 | 3 | 4 |
| I-c-83 | 3 | 4 | 5 | 2 | 3 | 4 | 4 | 2 | 5 |
| I-c-86 | 3 | 5 | 4 | 2 | 2 | 4 | 4 | 2 | 4 |
| I-c-88 | 4 | 5 | 5 | 2 | 3 | 5 | 4 | 2 | 5 |
| I-c-111 | 3 | 5 | 4 | 3 | 4 | 4 | 4 | 3 | 4 |
| I-c-113 | 2 | 5 | 5 | 2 | 3 | 5 | 4 | 3 | 5 |
| I-c-131 | 3 | 5 | 5 | 2 | 2 | 4 | 4 | 3 | 4 |
| I-c-135 | 2 | 4 | 4 | 2 | 3 | 5 | 4 | 3 | 5 |
| I-c-137 | 3 | 5 | 4 | 2 | 2 | 4 | 4 | 3 | 4 |
| I-c-139 | 2 | 5 | 4 | 2 | 2 | 4 | 4 | 3 | 4 |
| I-c-141 | 2 | 3 | 5 | 1 | 1 | 5 | 3 | 1 | 5 |
| I-c-145 | 2 | 5 | 4 | 2 | 2 | 3 | 3 | 2 | 5 |
| I-d-13 | 2 | 5 | 5 | 1 | 1 | 5 | 2 | 1 | 2 |
| 1-e-2 | 1 | — | — | 1 | — | — | — | — | 2 |
| 1-e-10 | — | — | — | 1 | — | — | 5 | — | 5 |
| 1-e-11 | — | — | — | 1 | — | — | — | — | — |
| 1-e-28 | 2 | — | — | 2 | — | — | 4 | — | 4 |
| 1-e-40 | — | — | — | 2 | — | — | 4 | — | 4 |

| | Effects | | | | | | |
|---|---|---|---|---|---|---|---|
| Compound | Blackgrass | Annual bluegrass | Common lambsquarters | Livid amaranth | Velvetleaf | Morning glory | Common Cocklebur | Sicklepod |
| I-a-1 | 2 | 4 | 5 | 5 | 4 | 5 | 4 | 5 |
| I-a-2 | 3 | 4 | 5 | 5 | 4 | 5 | 4 | 4 |
| I-a-3 | 1 | 4 | 5 | 5 | 4 | 5 | 4 | 4 |
| I-a-4 | 0 | 1 | 5 | 5 | 3 | 5 | 3 | 4 |
| I-a-6 | 5 | 5 | 5 | 5 | 5 | 5 | 5 | 5 |
| I-a-7 | 1 | 3 | 4 | 5 | 3 | 3 | 4 | 3 |
| I-a-13 | 3 | 4 | 5 | 5 | 4 | 5 | 4 | 5 |
| I-a-18 | 1 | 2 | 4 | 5 | 4 | 5 | 4 | 5 |
| I-c-1 | 1 | 1 | 3 | 4 | 2 | 5 | — | — |
| I-c-15 | 3 | 4 | 5 | 5 | 3 | 5 | — | — |
| I-c-40 | 2 | 2 | 4 | 4 | 1 | 3 | — | — |
| I-c-42 | 3 | 3 | 5 | 5 | 3 | 4 | — | — |
| I-c-44 | 3 | 4 | 5 | 5 | 2 | 5 | — | — |
| I-c-53 | 4 | 4 | 5 | 5 | 3 | 5 | — | — |
| I-c-54 | 4 | 4 | 5 | 5 | 3 | 3 | — | — |
| I-c-55 | 4 | 4 | 5 | 4 | 4 | 5 | — | — |
| I-c-57 | 3 | 4 | 5 | 4 | 3 | 5 | — | — |
| I-c-67 | 4 | 4 | 5 | 5 | 4 | 5 | — | — |
| I-c-72 | 3 | 4 | 5 | 5 | 3 | 5 | — | — |
| I-c-74 | 2 | 4 | 5 | 5 | 4 | 5 | — | — |
| I-c-76 | 2 | 2 | 4 | 5 | 3 | 5 | — | — |
| I-c-81 | 3 | 4 | 5 | 5 | 3 | 5 | — | — |
| I-c-83 | 4 | 4 | 5 | 5 | 4 | 5 | — | — |
| I-c-86 | 3 | 4 | 5 | 5 | 3 | 5 | — | — |
| I-c-88 | 5 | 4 | 5 | 5 | 4 | 5 | — | — |

TABLE 33-continued

| | | | | | | | | |
|---|---|---|---|---|---|---|---|---|
| I-c-111 | 4 | 4 | 5 | 5 | 3 | 5 | — | — |
| I-c-113 | 4 | 4 | 5 | 5 | 4 | 5 | — | — |
| I-c-131 | 4 | 4 | 5 | 5 | 4 | 5 | — | — |
| I-c-135 | 5 | 5 | 5 | 5 | 4 | 5 | — | — |
| I-c-137 | 3 | 4 | 5 | 5 | 4 | 5 | — | — |
| I-c-139 | 4 | 4 | 5 | 5 | 4 | 5 | — | — |
| I-c-141 | 1 | 3 | 5 | 5 | 4 | 5 | — | — |
| I-c-145 | 2 | 3 | 5 | 5 | 3 | 5 | — | — |
| I-d-13 | 1 | 1 | 5 | 5 | 4 | 5 | — | — |
| 1-e-2 | — | — | 3 | 4 | — | — | — | — |
| 1-e-10 | — | — | 5 | 5 | — | — | — | — |
| 1-e-11 | — | — | 5 | 5 | — | — | — | — |
| 1-e-28 | — | — | 5 | 5 | — | — | — | — |
| 1-e-40 | — | — | 5 | 5 | — | — | — | — |

UTILIZABILITY IN INDUSTRY

The herbicide containing the benzoxazole compound of the present invention as an effective ingredient has an excellent herbicidal effect.

The invention claimed is:
1. A compound represented by the formula (I-c) or the formula (I-d), the formula (I-c) being as follows:

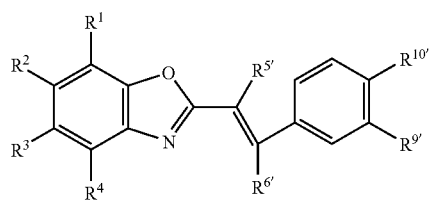

(I-c)

wherein $R^1$ to $R^4$ may be the same or different from each other, and each represent a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, $R^{12}S(O)_n$, an alkoxycarbonyl group having 1 to 4 carbon atoms, or a carbonyl group, where $R^{12}$ represents an alkyl group having 1 to 6 carbon atoms, and n is an integer of 0 to 2, provided that all of $R^1$ to $R^4$ are not simultaneously hydrogen atoms, $R^{5'}$ represents an alkyl group having 1 to 6 carbon atoms, $R^{6'}$ represents a hydrogen atom, a hydroxyl group, a halogen atom or an alkyl group having 1 to 4 carbon atoms, $R^{9'}$ represents a cyano group, a haloalkyl group having 1 to 4 carbon atoms, a haloalkoxy group having 1 to 4 carbon atoms, a nitro group or $R^{12}S(O)_n$, where $R^{12}$ and n have the same meanings as defined above, $R^{10'}$ represents a hydrogen atom, a halogen atom, a haloalkyl group having 1 to 4 carbon atoms or a cyano group; and the formula (I-d) being as follows:

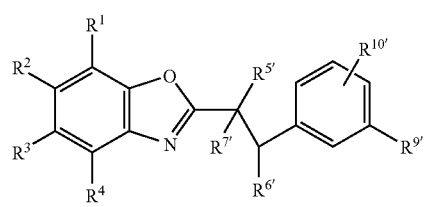

(I-d)

wherein $R^1$ to $R^4$, $R^{5'}$, $R^{6'}$, $R^{9'}$ and $R^{10'}$ have the same meanings as defined above, and
$R^{7'}$ represents a hydrogen atom, a hydroxyl group, a halogen atom or a substituted sulfonyloxy group.

2. The compound of claim 1, wherein $R^1$ represents a hydrogen atom, $R^4$ represents a hydrogen atom, and $R^{6'}$ represents a hydrogen atom.

3. The compound of claim 1, wherein $R^1$ represents a hydrogen atom, $R^4$ represents a hydrogen atom, $R^{6'}$ represents a hydrogen atom, and $R^{7'}$ represents a hydrogen atom.

4. A herbicide containing the compound represented by the formula (I-c) or the formula (I-d) as follows:

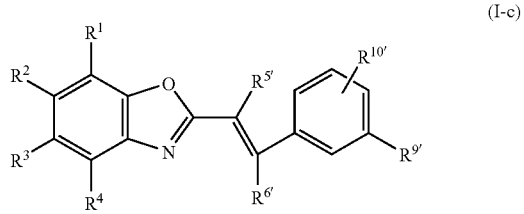

(I-c)

wherein $R^1$ to $R^4$ may be the same or different from each other, and each represent a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, $R^{12}S(O)_n$, an alkoxycarbonyl group having 1 to 4 carbon atoms, or a carbonyl group, where $R^{12}$ represents an alkyl group having 1 to 6 carbon atoms, and n is an integer of 0 to 2, provided that all of $R^1$ to $R^4$ are not simultaneously hydrogen atoms, $R^{5'}$ represents an alkyl group having 1 to 6 carbon atoms, $R^{6'}$ represents a hydrogen atom, a hydroxyl group, a halogen atom or an alkyl group having 1 to 4 carbon atoms, $R^{9'}$ represents a hydrogen atom, a cyano group, a haloalkyl group having 1 to 4 carbon atoms, a haloalkoxy group having 1 to 4 carbon atoms, a nitro group or $R^{12}S(O)_n$, where $R^{12}$ and n have the same meanings as defined above, $R^{10'}$ represents a hydrogen atom, a halogen atom, a haloalkyl group having 1 to 4 carbon atoms or a cyano group; and the formula (I-d) being as follows:

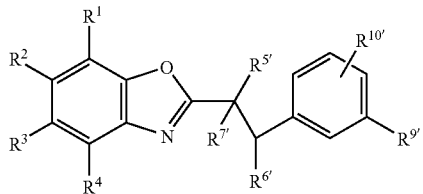

(I-d)

wherein $R^1$ to $R^4$, $R^{5'}$, $R^{6'}$, $R^{9'}$ and $R^{10'}$ have the same meanings as defined above, and $R^{7'}$ represents a hydrogen atom, a hydroxyl group, a halogen atom or a substituted sulfonyloxy group; and a herbicidally acceptable carrier.

5. A process for producing a compound (I-c) represented by the following formula (I-c):

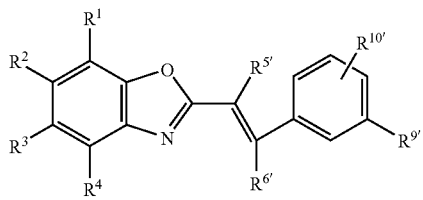

(I-c)

wherein $R^1$ to $R^4$ may be the same or different from each other, and each represent a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, $R^{12}S(O)_n$, an alkoxycarbonyl group having 1 to 4 carbon atoms, or a carbonyl group, where $R^{12}$ represents an alkyl group having 1 to 6 carbon atoms, and n is an integer of 0 to 2, provided that all of $R^1$ to $R^4$ are not simultaneously hydrogen atoms, $R^{5'}$ represents an alkyl group having 1 to 6 carbon atoms, $R^{6'}$ represents a hydrogen atom, a hydroxyl group, a halogen atom or an alkyl group having 1 to 4 carbon atoms, $R^{9'}$ represents a hydrogen atom, a cyano group, a haloalkyl group having 1 to 4 carbon atoms, a haloalkoxy group having 1 to 4 carbon atoms, a nitro group or $R^{12}S(O)_n$, where $R^{12}$ and n have the same meanings as defined above, $R^{10'}$ represents a hydrogen atom, a halogen atom, a haloalkyl group having 1 to 4 carbon atoms or a cyano group, or a compound (I-d) represented by the following formula (I-d):

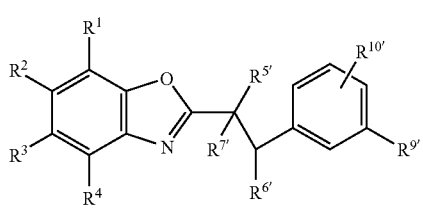

(I-d)

wherein $R^1$ to $R^4$, $R^{5'}$, $R^{6'}$, $R^{9'}$ and $R^{10'}$ have the same meanings as defined above, and $R^{7'}$ represents a hydrogen atom, a hydroxyl group, a halogen atom or a substituted sulfonyloxy group, which comprises reacting, in the presence of a base or an acid catalyst in a solvent, a compound (XII) represented by the following formula(XII):

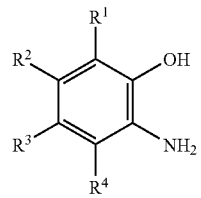

(XII)

wherein $R^1$ to $R^4$ have the same meanings as defined above, with a compound (XV-a) represented by the following formula (XV-a):

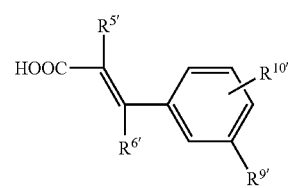

(XV-a)

wherein $R^{5'}$, $R^{6'}$, $R^{9'}$ and $R^{10'}$ have the same meanings as defined above, or a compound (XV-b) represented by the following formula (XV-b):

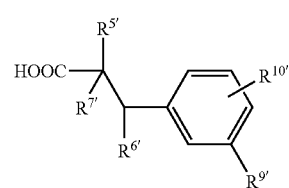

(XV-b)

wherein $R^{5'}$, $R^{6'}$, $R^{7'}$, $R^{9'}$ and $R^{10'}$ have the same meanings as defined above.

6. A process for producing a compound (I-c) which comprises dehydrating a compound represented by the following formula (I-d'):

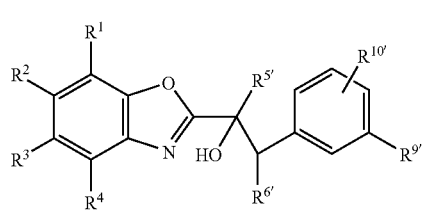

(I-d')

wherein $R^1$ to $R^4$ may be the same or different from each other, and each represent a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, $R^{12}S(O)_n$, an alkoxycarbonyl group having 1 to 4 atoms, or a carbonyl group, where $R^{12}$ represents an alkyl group having 1 to 6 carbon atoms, n is an integer of 0 to 2, provided ha all of $R^1$ to $R^4$ are not simultaneously hydrogen atoms, $R^{5'}$ represents an alkyl group having 1 to 6 carbon atoms, $R^{6'}$ represents a hydrogen atom, a hydroxyl group, a halogen atom or an alkyl group having 1 to 4 carbon atoms, $R^{9'}$ represents a hydrogen atom, a cyano group, a haloalkyl group having 1 to 4 carbon atoms, a haloalkoxy group having 1 to 4 carbon atoms, a nitro group or $R^{12}S(O)_n$, where $R^{12}$ and n have the same meanings as defined above, and $R^{10'}$ represents a hydrogen atom, a halogen atom, a haloalkyl group having 1 to 4 carbon atoms or a cyano group.

7. A process for producing a compound (I-c) which comprises reacting a compound represented by the following formula (XVI):

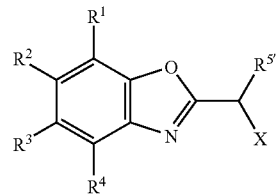

(XVI)

wherein $R^1$ to $R^4$ may be the same or different from each other, and each represent a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, $R^{12}S(O)_n$, an alkoxycarbonyl group having 1 to 4 carbon atoms, or a carbonyl group, where $R^{12}$ represents an alkyl group having 1 to 6 carbon atoms, and n is an integer of 0 to 2, provided that all of $R^1$ to $R^4$ are not simultaneously hydrogen atoms, $R^{5'}$ represents an alkyl group having 1 to 6 carbon atoms, and X represents a halogen atom, with triphenylphosphine in a solvent to form a phosphonium salt, and further reacting a compound (XVII) represented by the following formula (XVII):

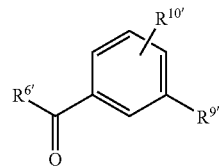

(XVII)

wherein $R^{6'}$ represents a hydrogen atom, a hydroxyl group, a halogen atom or an alkyl group having 1 to 4 carbon atoms, $R^{9'}$ represents a hydrogen atom, a cyano group, a haloalkyl group having 1 to 4 carbon atoms, a haloalkoxy group having 1 to 4 carbon atoms, a nitro group or $R^{12}S(O)_n$, where $R^{12}$ and n have the same meanings as defined above, $R^{10'}$ represents a hydrogen atom, a halogen atom, a haloalkyl group having 1 to 4 carbon atoms or a cyano group.

* * * * *